United States Patent
Cardozo et al.

(10) Patent No.: US 7,550,473 B2
(45) Date of Patent: Jun. 23, 2009

(54) PYRIMIDINE DERIVATIVES USEFUL AS INHIBITORS OF PKC-THETA

(75) Inventors: Mario G. Cardozo, San Francisco, CA (US); Derek Cogan, Sandy Hook, CT (US); Charles Lawrence Cywin, Bethel, CT (US); George Dahmann, Attenweiler (DE); Darren DiSalvo, New Milford, CT (US); John David Ginn, New Milford, CT (US); Anthony S. Prokopowicz, III, Beekman, NY (US); Denice M. Spero, West Redding, CT (US); Erick Richard Roush Young, Danbury, CT (US)

(73) Assignees: Boehringer Ingelheim Pharmaceuticals, Inc., Ridgefield, CT (US); Boehringer Ingelheim Pharma GmbH & Co. KG, Ingelheim (DE)

( * ) Notice: Subject to any disclaimer, the term of this patent is extended or adjusted under 35 U.S.C. 154(b) by 278 days.

(21) Appl. No.: 10/933,635

(22) Filed: Sep. 3, 2004

(65) Prior Publication Data

US 2005/0124640 A1 Jun. 9, 2005

Related U.S. Application Data

(63) Continuation-in-part of application No. 10/766,079, filed on Jan. 27, 2004.

(60) Provisional application No. 60/443,700, filed on Jan. 30, 2003.

(51) Int. Cl.
C07D 239/42 (2006.01)
A61K 31/505 (2006.01)

(52) U.S. Cl. .................... 514/275; 544/323

(58) Field of Classification Search ................ 544/323; 514/275
See application file for complete search history.

(56) References Cited

U.S. PATENT DOCUMENTS

| 6,432,963 B1 | 8/2002 | Hisamichi et al. |
| 7,173,028 B2 * | 2/2007 | Dahmann et al. ........ 514/235.8 |
| 2003/0171359 A1 | 9/2003 | Dahmann et al. |
| 2004/0029902 A1 | 2/2004 | Singh et al. |
| 2005/0038243 A1 | 2/2005 | Singh et al. |

FOREIGN PATENT DOCUMENTS

| EP | 1054004 A1 | 11/2000 |
| WO | WO 97/19065 | 5/1997 |
| WO | WO 00/75113 A1 | 12/2000 |
| WO | WO 01/00213 A1 | 1/2001 |
| WO | 0164656 A1 | 9/2001 |
| WO | 02064096 A2 | 8/2002 |
| WO | WO 02/096887 A1 | 12/2002 |
| WO | WO 02/096888 A1 | 12/2002 |
| WO | 03032997 A1 | 4/2003 |
| WO | WO 03/106451 A1 | 12/2003 |
| WO | 2004067516 A1 | 8/2004 |

OTHER PUBLICATIONS

Ulrich, Chapter 4: Crystallization, Kirk-Othmer Encylopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Casanova et al., PubMed Abstract (Rev Neurol 28(9):909-15) May 1999.*
International Search Report, Form PCT/ISA/210 for corresponding PCT/US2004/002240.

* cited by examiner

Primary Examiner—Deepak Rao
(74) Attorney, Agent, or Firm—Michael P. Morris; Mary-Ellen M. Devlin; Philip I. Datlow

(57) ABSTRACT

Disclosed are novel compounds of formula (I):

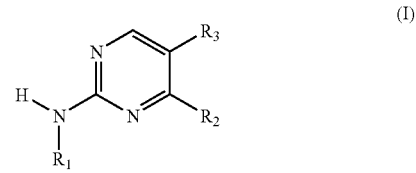

wherein $R_1$, $R_2$ and $R_3$ are as defined herein, which are useful as inhibitors of PKC-theta and are thus useful for treating a variety of diseases and disorders that are mediated or sustained through the activity of PKC-theta, including immunological disorders and type II diabetes. This invention also relates to pharmaceutical compositions comprising these compounds, methods of using these compounds in the treatment of various diseases and disorders, processes for preparing these compounds and intermediates useful in these processes.

13 Claims, No Drawings

PYRIMIDINE DERIVATIVES USEFUL AS INHIBITORS OF PKC-THETA

RELATED APPLICATIONS

This application is a continuation-in-part of U.S. Nonprovisional application Ser. No. 10/766,079, filed Jan. 27, 2004, which claims benefit to U.S. Provisional Application No. 60/443,700, filed Jan. 30, 2003, and said applications are herein incorporated by reference in their entirety.

FIELD OF THE INVENTION

This invention relates to substituted pyrimidine derivatives which are useful as inhibitors of PKC-theta and are thus useful for treating a variety of diseases and disorders that are mediated or sustained through the activity of PKC-theta, including immunological disorders and type II diabetes. This invention also relates to pharmaceutical compositions comprising these compounds, methods of using these compounds in the treatment of various diseases and disorders, processes for preparing these compounds and intermediates useful in these processes.

BACKGROUND OF THE INVENTION

The protein kinase C family is a group of serine/threonine kinases that is comprised of twelve related isoenzymes. These kinases are expressed in a wide range of tissues and cell types. Its members are encoded by different genes and are sub-classified according to their requirements for activation. The classical PKC enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG.

PKC-theta is a member of the nPKC sub-family. It has a restricted expression pattern, found predominantly in T cells and skeletal muscle. Upon T cell activation, a supramolecular activation complex (SMAC) forms at the site of contact between the T cell and antigen presenting cell (APC). PKC-theta is the only PKC isoform found to localize at the SMAC (C. Monks et al., *Nature*, 1997, 385, 83), placing it in proximity with other signaling enzymes that mediate T cell activation processes. In another study (G. Baier-Bitterlich et al., *Mol. Cell. Biol.*, 1996, 16, 842) the role of PKC-theta in the activation of AP-1, a transcription factor important in the activation of the IL-2 gene, was confirmed. In unstimulated T cells, constitutively active PKC-theta stimulated AP-1 activity while in cells with dominant negative PKC-theta, AP-1 activity was not induced upon activation by PMA. Other studies showed that PKC-theta, via activation of IκB kinase beta, mediates activation of NF-κB induced by T cell receptor/CD28 co-stimulation (N. Coudronniere et al., *Proc. Nat. Acad. Sci. U.S.*, 2000, 97, 3394; X. Lin et al., *Moll. Cell. Biol.*, 2000, 20, 2933). Proliferation of peripheral T cells from PKC-theta knockout mice, in response to T cell receptor (TCR)/CD28 stimulation was greatly diminished compared to T cells from wild type mice. In addition, the amount of IL-2 released from the T cells was also greatly reduced (Z. Sun et al., *Nature*, 2000, 404, 402). Otherwise, the PKC-theta knockout mice seemed normal and were fertile.

The studies cited above and other studies confirm the critical role of PKC-theta in T cell activation and subsequent release of cytokines such as IL-2 and T cell proliferation (A. Altman et al., *Immunology Today*, 2000, 21, 567). Thus an inhibitor of PKC-theta would be of therapeutic benefit in treating immunological disorders and other diseases mediated by the inappropriate activation of T cells.

It has been well established that T cells play an important role in regulating the immune response (Powrie and Coffman, *Immunology Today*, 1993, 14, 270). Indeed, activation of T cells is often the initiating event in immunological disorders. Following activation of the TCR, there is an influx of calcium that is required for T cell activation. Upon activation, T cells produce cytokines, including as IL-2, leading to T cell proliferation, differentiation, and effector function. Clinical studies with inhibitors of IL-2 have shown that interference with T cell activation and proliferation effectively suppresses immune response in vivo (Waldmann, *Immunology Today*, 1993, 14, 264). Accordingly, agents that inhibit T lymphocyte activation and subsequent cytokine production are therapeutically useful for selectively suppressing the immune response in a patient in need of such immunosuppression and therefore are useful in treating immunological disorders such as autoimmune and inflammatory diseases.

In addition, PKC theta activation has been shown to be associated with insulin resistance in skeletal muscle (M. E. Griffen et al., *Diabetes*, 1999, 48, 1270). Therefore inhibitors of PKC-theta may also be useful for treating type II diabetes.

Dahmann et al, U.S. application Ser. No. 10/271,763, filed Oct. 16, 2002, (now U.S. Patent Application Publication No. 2003/0171359 A1) discloses pyrimidine derivatives as inhibitors of various protein kinases such as SRC kinase, PLK kinase and particularly cyclin-dependent kinases (CDKs) and Aurora B. WO 00/75113 and U.S. Pat. No. 6,432,963 describe pyrimidine carboxamides as inhibitors of Syk tyrosine kinase. WO 01/00213 discloses heteroaryl substituted pyrimidines as SRC kinase inhibitors. WO 97/19065 describes substituted 2-anilinopyrimidine compounds as inhibitors of certain protein kinases. WO 02/096887 and WO 02/096888 both disclose 2-anilinopyrimidine derivatives as inhibitors of cyclin-dependent kinases. WO 03/106451 discloses certain substituted diaminopyrimidine compounds as inhibitors of PKC-theta.

There is a continuing need in the art for compounds that are potent and selective inhibitors of PKC-theta.

BRIEF SUMMARY OF THE INVENTION

In a general aspect, the present invention is directed to the compounds of the following formula (I):

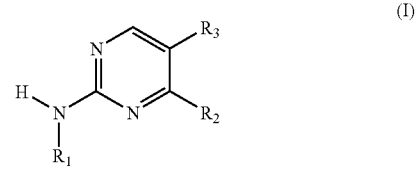

wherein $R_1$, $R_2$ and $R_3$ are as defined herein, as well as the tautomers, pharmaceutically acceptable salts, solvates, and amino-protected derivatives thereof. It has been found that the compounds of formula (I) have valuable pharmacological properties, particularly an inhibiting activity on PKC-theta. Many of the compounds of the invention are not only potent inhibitors of PKC-theta but are also selective for the inhibition of PKC-theta as compared to one or more other protein kinases.

In another aspect, the present invention is directed to a method of inhibiting PKC-theta activity in a patient comprising administering to the patient a compound of the present invention as described above.

In another aspect, the present invention is directed to a method of treating a disease or disorder associated with the activation of T cells comprising administering to a patient in need of such treatment a compound of the present invention as described above.

In another aspect, the present invention is directed to a method of treating an immunological disorder comprising administering to a patient in need of such treatment a compound of the present invention as described above. Examples of such immunological disorders that may be treated include, for example, inflammatory diseases, autoimmune diseases, organ and bone marrow transplant rejection and other disorders associated with T cell mediated immune response, including acute or chronic inflammation, allergies, contact dermatitis, psoriasis, rheumatoid arthritis, multiple sclerosis, type I diabetes, inflammatory bowel disease, Guillain-Barre syndrome, Crohn's disease, ulcerative colitis, graft versus host disease (and other forms of organ or bone marrow transplant rejection) and lupus erythematosus.

In another aspect, the present invention is directed to a method of treating type II diabetes comprising administering to a patient in need of such treatment a compound of the present invention as described above.

In yet additional aspects, the present invention is directed to pharmaceutical compositions comprising the above-mentioned compounds, processes for preparing the above-mentioned compounds and intermediates used in these processes.

DETAILED DESCRIPTION OF THE INVENTION

Definition of Terms and Conventions Used

Terms not specifically defined herein should be given the meanings that would be given to them by one of skill in the art in light of the disclosure and the context. As used in the present specification and claims, however, unless specified to the contrary, the following terms have the meaning indicated and the following conventions are adhered to.

A. Chemical Nomenclature, Terms, and Conventions

In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

All alkyl groups shall be understood as being branched or unbranched unless otherwise specified. Other more specific definitions are as follows:

The term "halogen" as used in the present specification shall be understood to mean bromine, chlorine, fluorine or iodine.

The term "heteroaryl" refers to a stable 5 or 6 membered, monocyclic aromatic heterocycle radical, wherein the heterocycle radical is optionally fused to either an aryl, e.g. benzene, or to a second 5 or 6 membered, monocyclic aromatic heterocycle to form in each case a bicyclic heteroaryl group. Each heterocycle consists of carbon atoms and from 1 to 3 heteroatoms chosen from nitrogen, oxygen and sulfur. The heterocycle may be attached by any atom of the cycle, which results in the creation of a stable structure. Example "heteroaryl" radicals include, pyridyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl.

The term "aryl" shall be understood to mean a 6-10 membered monocyclic or bicyclic aromatic carbocycle, and includes, for example, phenyl and naphthyl; other terms comprising "aryl" will have the same definition for the aryl component, and examples of these moieties include: arylalkyl, aryloxy or arylthio.

The term "oxo" refers to a double-bonded oxygen group (=O).

The phrases "wherein each of the $C_{1-6}$alkyl groups", "wherein each of the $C_{1-8}$alkyl groups" or "wherein each of the aryl groups" or similar language in a definition is intended to refer to the indicated groups when either alone or as part of another chemical group if such combined groups are provided for in a definition. For example, the language "wherein each of the $C_{1-6}$alkyl groups" refers to $C_{1-6}$alkyl groups as well as $C_{1-6}$alkyl groups when attached to other groups, e.g., the $C_{1-6}$alkyl portion of a $C_{1-6}$alkyloxy or aryl-$C_{1-6}$alkyl group, if such groups are provided for in a definition.

The term "amino protected derivatives" shall be understood to mean compounds of formula (I) wherein one or more of the amine groups are protected by suitable amino protecting groups. Amino protecting groups that may be used include, for example, alkoxycarbonyl groups, such as tert-butyloxycarbonyl (Boc) and ethoxycarbonyl, Mannich bases, Schiff bases and amino acids. As would be understood by a person skilled in the art, such amino protected compounds may be useful as intermediates in the preparation of other compounds of formula (I), e.g., as described in the synthetic processes below, and/or may themselves be useful as prodrugs that can be administered to a patient to be converted in vivo into a PKC-theta inhibitor having the resulting pharmacologic and therapeutic effects expected from the inhibition of PKC-theta in a patient.

The term "pharmaceutically acceptable salts" include those derived from pharmaceutically acceptable inorganic and organic acids and bases. Examples of suitable acids include hydrochloric, hydrobromic, carbonic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_{1-4}$ alkyl$)_4^+$ salts.

The term "solvate" means a physical association of a compound with one or more solvent molecules or a complex of variable stoichiometry formed by a solute (for example, a compound of Formula (I)) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The term "compounds of the invention" and equivalent expressions are meant to embrace compounds of Formula (I) as herein described, including the tautomers, pharmaceutically acceptable salts, solvates, and amino-protected derivatives thereof, where the context so permits. In general, the compounds of the invention and the formulas designating the compounds of the invention are understood to only include the stable compounds thereof and exclude unstable compounds, even if an unstable compound might be considered to be literally embraced by the compound formula.

The term "stable compound" means a compound that is sufficiently robust to survive isolation to a useful degree of purity from a reaction mixture, and formulation into an efficacious therapeutic agent. For example, a compound which would have a "dangling valency" is not a compound contemplated by the invention.

Specific compounds of the present invention may be identified in the present specification by chemical name and/or chemical structure. In the event of any conflict between the chemical name and chemical structure, the chemical structure will control.

B. Isomer Terms and Conventions

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

C. Pharmaceutical Administration Terms and Conventions

The term "patient" includes both human and non-human mammals.

The term "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the state of the art, and this disclosure.

The phrase "disease or disorder associated with the activation of T cells" and similar expressions mean that the activation of T cells is a contributing factor to either the origin or continuation of the disease or disorder in the patient.

EMBODIMENTS OF THE INVENTION

In its broadest generic aspect, the invention provides novel compounds of the formula (I) below:

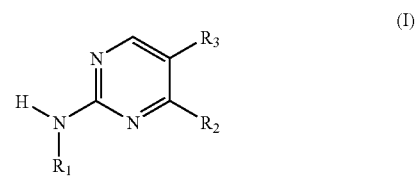

wherein:
$R_1$ is $C_{1-8}$alkyl, $C_{3-7}$cycloalkyl, $C_{3-7}$cycloalkyl-$C_{1-8}$alkyl, naphthyl, quinolinyl, aryl-$C_{1-8}$alkyl, or heteroaryl-$C_{1-8}$alkyl, wherein in each of the $C_{1-8}$alkyl groups a methylene group may optionally be replaced by —NHC(O)— or —C(O)NH—, and wherein each of the $C_{1-8}$alkyl groups is optionally substituted by an oxo group or one or more $C_{1-3}$alkyl groups wherein two alkyl substituents on the same carbon atom of a $C_{1-8}$alkyl group may optionally be combined to form a $C_{2-5}$ alkylene bridge, and wherein the aryl group is optionally substituted on adjacent carbon atoms by a $C_{3-6}$alkylene bridge group wherein a methylene group is optionally replaced by an oxygen, —S—, —S(O)—, —SO_2— or —N(R_6)—;

or R₁ has the following structure:

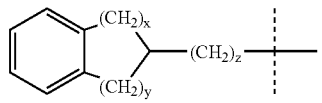

wherein x and y are independently 0, 1, 2, 3 or 4, provided that x+y is 2 to 4, z is 0, 1 or 2, and one or two CH₂ groups in the ring may optionally be replaced by —O—, —S—, —S(O)—, —SO₂— or —N(R₆);

wherein each R₁ group is optionally substituted by one or more of the following groups: $C_{1-6}$alkyl, $C_{3-6}$cycloalkyl, halogen, nitro, hydroxy, $C_{1-6}$alkyloxy, $C_{1-6}$alkylthio, aryl, aryl$C_{1-6}$alkyl, aryloxy, arylthio, aminosulfonyl, or amino optionally substituted by one or two $C_{1-6}$alkyl groups, wherein each aryl group is optionally substituted by one or more $C_{1-6}$alkyl, halogen, nitro, hydroxy or amino optionally substituted by one or two $C_{1-6}$alkyl groups, and wherein in each of the $C_{1-6}$alkyl groups a methylene group may optionally be replaced by —NHC(O)— or —C(O)NH—, and wherein each of the $C_{1-6}$alkyl groups is optionally substituted by one or more halogens;

R₂ is selected from the following groups:

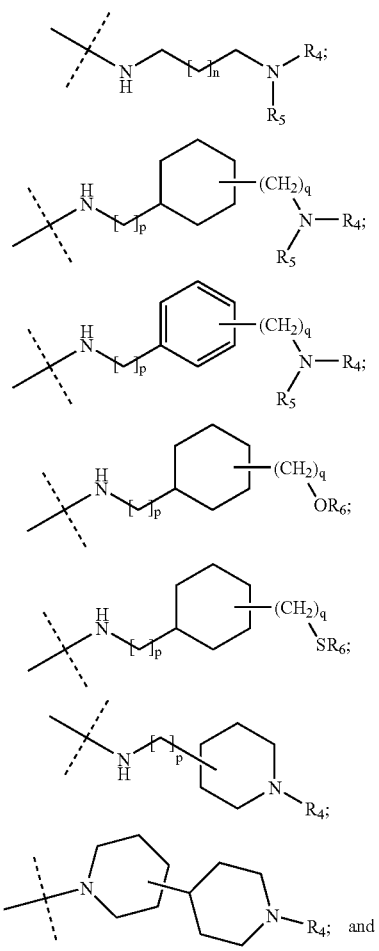

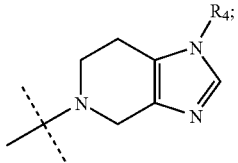

wherein:
n is an integer from 3 to 8;
p is an integer from 1 to 3;
q is an integer from 0 to 3;
R₄ and R₅ are each independently selected from hydrogen, $C_{1-6}$alkyl, aryl$C_{1-6}$alkyl, or amidino, wherein each aryl group is optionally substituted by one or more $C_{1-6}$alkyl, halogen, nitro, hydroxy or amino optionally substituted by one or two $C_{1-6}$alkyl groups, and wherein each of the $C_{1-6}$alkyl groups is optionally substituted by one or more halogens, and wherein the amidino is optionally substituted by one to three $C_{1-6}$alkyl;
R₆ is hydrogen or $C_{1-6}$alkyl;
wherein each R₂ group is optionally substituted by one or more $C_{1-6}$alkyl, $C_{1-6}$alkoxy, CN, —OH, —NH₂ or halogen;
R₃ is halogen, cyano, nitro, $C_{1-6}$alkyl, $C_{1-6}$alkyloxycarbonyl or aminocarbonyl, wherein each of the $C_{1-6}$alkyl groups is optionally substituted by one or more halogens;
or a tautomer, pharmaceutically acceptable salt, solvate, or amino-protected derivative thereof,
with the proviso that the specific compounds of U.S. application Ser. No. 10/271,763 are excluded.

The phrase "specific compounds of U.S. application Ser. No. 10/271,763" means all the individual compounds that are specifically identified by name or structure in the disclosure of U.S. application Ser. No. 10/271,763, filed Oct. 16, 2002, herein incorporated by reference in its entirety. This includes, but is not limited to, the following compounds:
2-(2-naphthylamino)-4-(1,4,6,7-tetrahydro-imidazo[4,5-c] pyridin-5-yl)-5-trifluoromethyl-pyrimidine;
2-(benzylamino)-4-(4-aminomethyl-cyclohexylmethylamino)-5-nitro-pyrimidine;
2-(benzylamino)-4-(4-aminomethyl-cyclohexylmethylamino)-5-trifluoromethyl-pyrimidine; and
2-(2-chlorobenzylamino)-4-(4-aminomethyl-cyclohexylmethylamino)-5-nitro-pyrimidine.

All the specific compounds of U.S. application Ser. No. 10/271,763, including the four compounds listed above, are excluded from the present invention.

In another embodiment of the invention, there are provided compounds of the formula (I) as described above, and wherein:
R₁ is aryl-$C_{1-4}$alkyl or heteroaryl-$C_{1-4}$alkyl, wherein in each of the $C_{1-4}$alkyl groups a methylene group may optionally be replaced by —NHC(O)— or —C(O)NH—, and wherein each of the $C_{1-4}$alkyl groups is optionally substituted by an oxo group or one or more $C_{1-3}$alkyl groups wherein two alkyl substituents on the same carbon atom of a $C_{1-4}$alkyl group may optionally be combined to form a $C_{2-5}$ alkylene bridge, and wherein the aryl group is optionally substituted on adjacent carbon atoms by a $C_{3-6}$alkylene bridge group wherein a methylene group is optionally replaced by an oxygen, sulfur or —N(R₆)—;

or $R_1$ has the following structure:

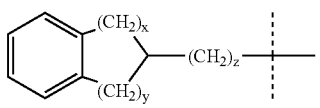

wherein x and y are independently 0, 1, 2 or 3, provided that x+y is 2 to 3, and z is 0 or 1;
wherein "heteroaryl" is defined as pyridyl, furyl, thienyl, pyrrolyl, imidazolyl, or indolyl;
wherein each $R_1$ group is optionally substituted by one or more of the following groups: $C_{1-6}$alkyl, Cl, Br, F, nitro, hydroxy, $CF_3$, —$OCF_3$, —$OCF_2H$, —$SCF_3$, $C_{1-4}$alkyloxy, $C_{1-4}$alkylthio, phenyl, benzyl, phenyloxy, phenylthio, aminosulfonyl, or amino optionally substituted by one or two $C_{1-3}$alkyl groups;
$R_2$ is selected from the following groups:

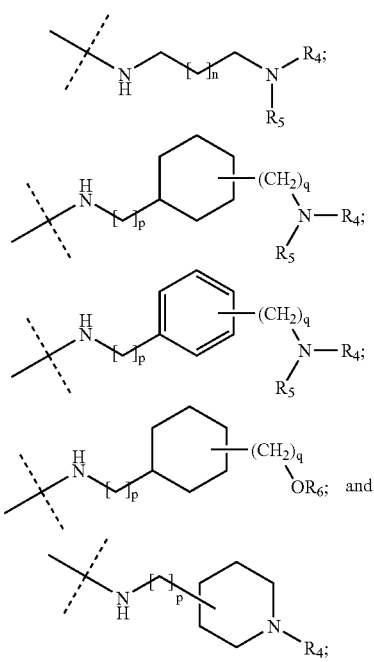

wherein:
n is an integer from 5 to 7;
p is an integer from 1 to 2;
q is an integer from 1 to 2;
$R_4$ and $R_5$ are each independently selected from hydrogen, $C_{1-6}$alkyl, aryl$C_{1-6}$alkyl, or amidino;
$R_6$ is hydrogen;
$R_3$ is Br, Cl, F, cyano or nitro;
or a tautomer, pharmaceutically acceptable salt, solvate, or amino-protected derivative thereof;

In another embodiment of the invention, there are provided compounds of the formula (I) as described above, and wherein:
$R_1$ is phenyl-$C_{1-4}$alkyl or naphthyl$C_{1-2}$alkyl,
wherein each $R_1$ group is optionally substituted by one or more of the following groups: methyl, Cl, Br, F, nitro, hydroxy, $CF_3$, —$OCF_3$, —$SCF_3$, $C_{1-4}$alkyloxy or $C_{1-4}$alkylthio;

$R_2$ is selected from the following groups:

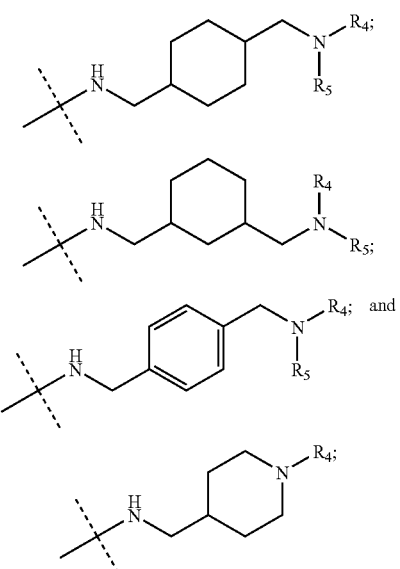

wherein:
$R_4$ and $R_5$ are each independently selected from hydrogen, $C_{1-3}$ alkyl, or amidino;
$R_3$ is Br, Cl, cyano or nitro;
or a tautomer, pharmaceutically acceptable salt, solvate, or amino-protected derivative thereof;

In another embodiment of the invention, there are provided compounds of the formula (I) as described above, and wherein:
$R_1$ is phenyl$CH_2$—
wherein the phenyl group is optionally substituted by one or more of the following groups: methyl, Cl, Br, F, nitro, hydroxy, $CF_3$, —$OCF_3$, —$SCF_3$, $C_{1-4}$alkyloxy or $C_{1-4}$alkylthio;
$R_2$ is selected from the following groups:

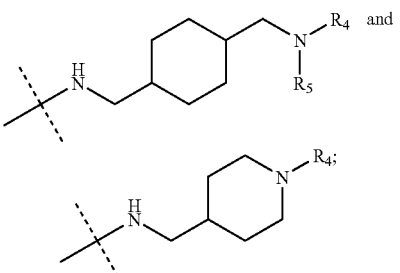

$R_3$ is nitro;
$R_4$ and $R_5$ are each independently selected from hydrogen, methyl, or amidino;
or a tautomer, pharmaceutically acceptable salt, solvate, or amino-protected derivative thereof.

In another embodiment of the invention, there are provided compounds of the formula (I) selected from the group below:

| | |
|---|---|
| ethyl 4-({[4-(aminomethyl)cyclohexyl]methyl}amino)-2-[(2-chlorobenzyl)amino]pyrimidine-5-carboxylate | m/z 432.30 (M + H)+ |

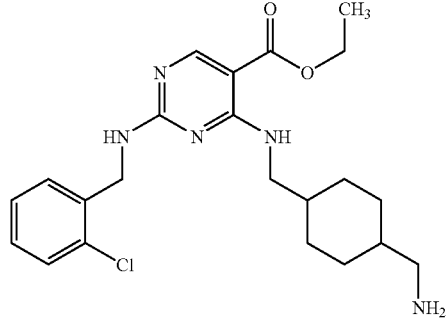

| | |
|---|---|
| $N^4$-{[4-(aminomethyl)cyclohexyl]methyl}-5-nitro-$N^2$-[(2R)-1,2,3,4-tetrahydronaphthalen-2-yl]pyrimidine-2,4-diamine | m/z 411.5 (M + H)+ |

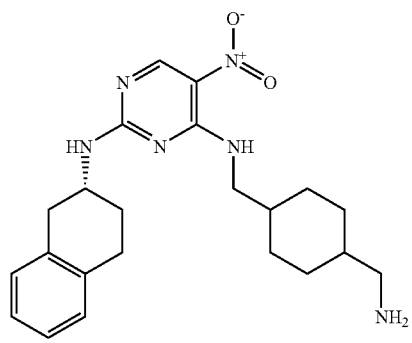

| | |
|---|---|
| $N^4$-{[4-(aminomethyl)cyclohexyl]methyl}-5-nitro-$N^2$-[(2S)-1,2,3,4-tetrahydronaphthalen-2-yl]pyrimidine-2,4-diamine | m/z 411.4 (M + H)+ |

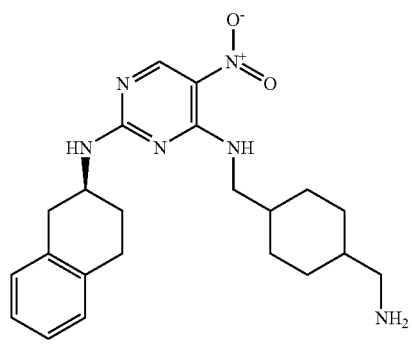

| | |
|---|---|
| $N^4$-{[4-(aminomethyl)cyclohexyl]methyl}-5-nitro-$N^2$-[(1R)-1,2,3,4-tetrahydronaphthalen-1-yl]pyrimidine-2,4-diamine | m/z 411.4 (M + H)+ |

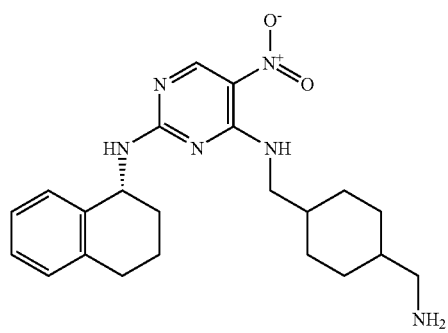

-continued

| | |
|---|---|
| $N^4$-{[4-(aminomethyl)cyclohexyl]methyl}-5-nitro-$N^2$-[(1S)-1,2,3,4-tetrahydronaphthalen-1-yl]pyrimidine-2,4-diamine | m/z 411.5 (M + H)+ |

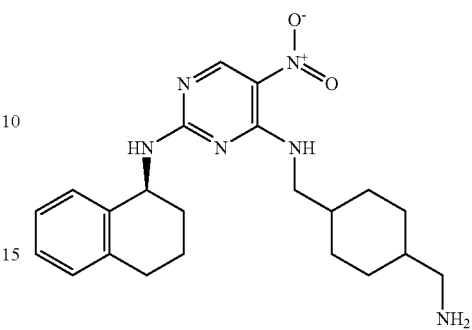

| | |
|---|---|
| $N^4$-{[4-(aminomethyl)cyclohexyl]methyl}-$N^2$-[2-(4-chlorophenyl)ethyl]-5-nitropyrimidine-2,4-diamine | m/z 419.4 (M + H)+ |

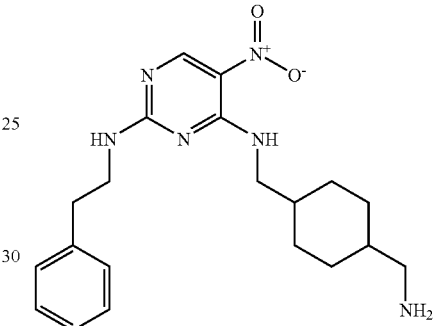

| | |
|---|---|
| $N^4$-{[4-(aminomethyl)cyclohexyl]methyl}-$N^2$-[2-(2-methylphenyl)ethyl]-5-nitropyrimidine-2,4-diamine | m/z 399.5 (M + H)+ |

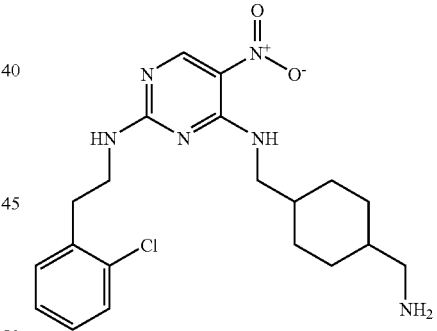

| | |
|---|---|
| $N^4$-{[4-(aminomethyl)cyclohexyl]methyl}-$N^2$-[2-(3-methylphenyl)ethyl]-5-nitropyrimidine-2,4-diamine | m/z 399.5 (M + H)+ |

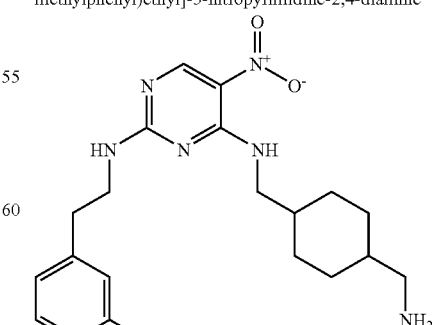

-continued

| | |
|---|---|
| N⁴-{[4-(aminomethyl)cyclohexyl]methyl}-N²-[2-(4-methylphenyl)ethyl]-5-nitropyrimidine-2,4-diamine 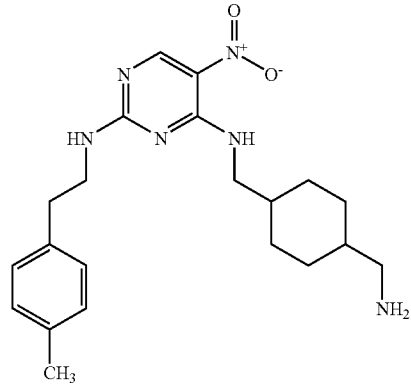 | m/z 399.4 (M + H)⁺ |
| N⁴-{[4-(aminomethyl)cyclohexyl]methyl}-N²-[2-(2-fluorophenyl)ethyl]-5-nitropyrimidine-2,4-diamine 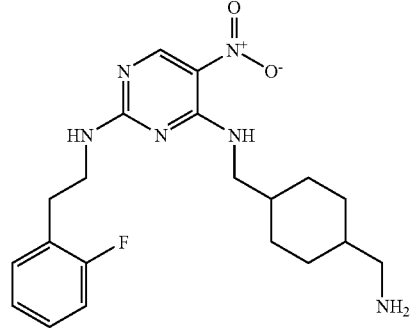 | m/z 403.4 (M + H)⁺ |
| N⁴-{[4-(aminomethyl)cyclohexyl]methyl}-N²-[2-(3-fluorophenyl)ethyl]-5-nitropyrimidine-2,4-diamine 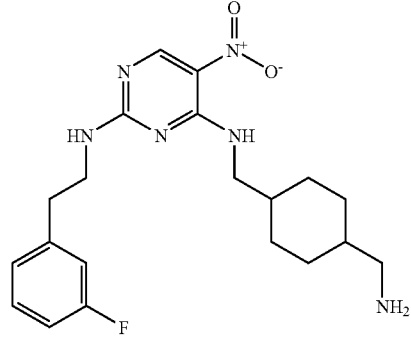 | m/z 403.5 (M + H)⁺ |
| N⁴-{[4-(aminomethyl)cyclohexyl]methyl}-N²-[2-(4-fluorophenyl)ethyl]-5-nitropyrimidine-2,4-diamine 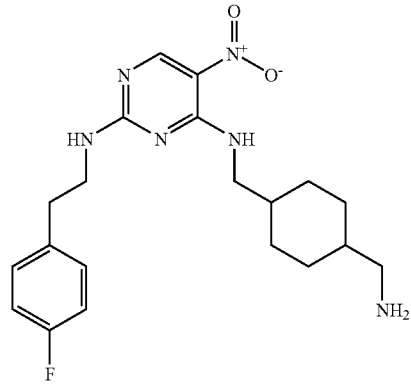 | m/z 403.4 (M + H)⁺ |

-continued

| | |
|---|---|
| N²-(2-aminobenzyl)-N⁴-{[4-(aminomethyl)cyclohexyl]methyl}-5-nitropyrimidine-2,4-diamine 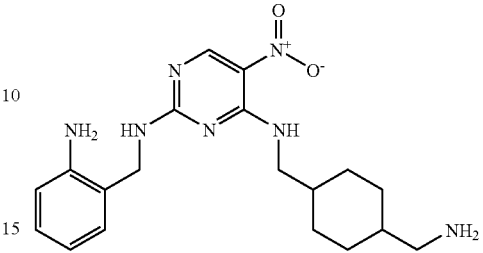 | m/z 386.4 (M + H)⁺ |
| N⁴-{[4-(aminomethyl)cyclohexyl]methyl}-N²-(3,5-dimethoxybenzyl)-5-nitropyrimidine-2,4-diamine 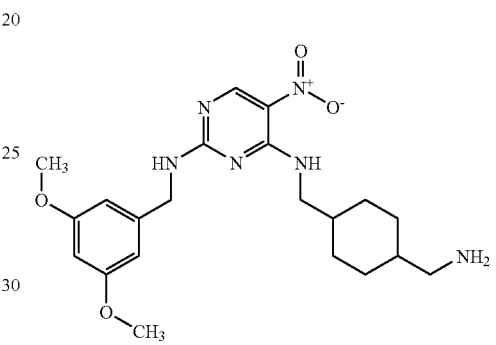 | m/z 431.4 (M + H)⁺ |
| N⁴-{[4-(aminomethyl)cyclohexyl]methyl}-N²-[3,5-bis(trifluoromethyl)benzyl]-5-nitropyrimidine-2,4-diamine 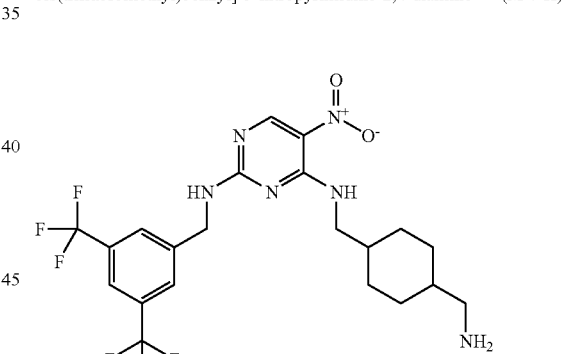 | m/z 507.3 (M + H)⁺ |
| {3-[({2-[(2-chlorobenzyl)amino]-5-nitropynmidin-4-yl}amino)methyl]phenyl}methane amine 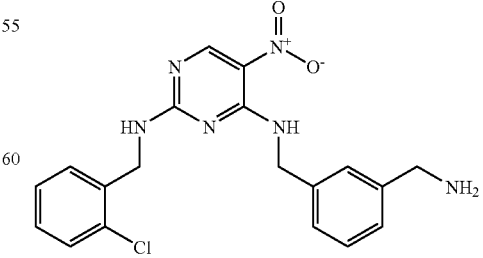 | m/z 399.3 (M + H)⁺ |

| | |
|---|---|
| 2-({[4-({[4-(aminomethyl)cyclohexyl]methyl}amino)-5-nitropyrimidin-2-yl]amino}methyl)phenol | m/z 387.3 (M + H)+ |

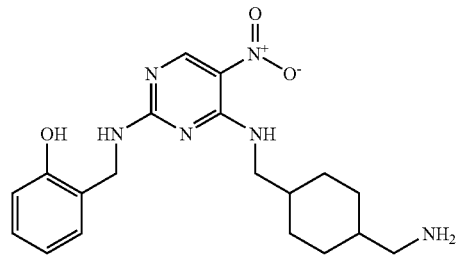

| | |
|---|---|
| N²-(5-amino-2-chlorobenzyl)-N⁴-{[4-(aminomethyl)cyclohexyl]methyl}-5-nitropyrimidine-2,4-diamine | m/z 420.3 (M + H)+ |

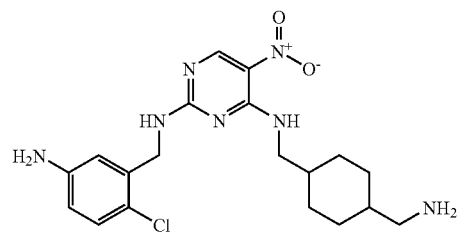

| | |
|---|---|
| 4-({[4-(aminomethyl)cyclohexyl]methyl}amino)-2-[(2-chlorobenzyl)amino]pyrimidine-5-carboxamide | m/z 403.40 (M + H)+ |

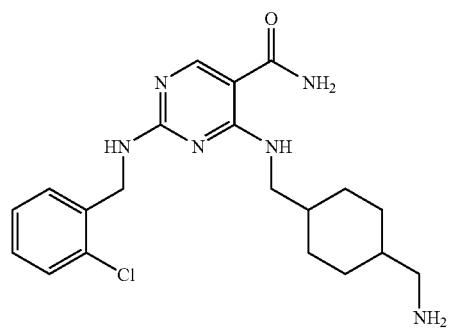

| | |
|---|---|
| N⁴-{[4-(aminomethyl)cyclohexyl]methyl}-N²-(2-chlorobenzyl)-5-fluoropyrimidine-2,4-diamine | m/z 378.40 (M + H)+ |

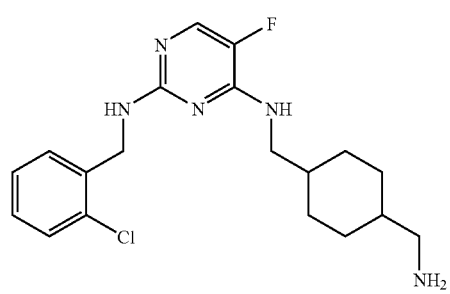

| | |
|---|---|
| 3-({[4-({[4-(aminomethyl)cyclohexyl]methyl}amino)-5-nitropyrimidin-2-yl]amino}methyl)-N-[2-(2-methylphenyl)ethyl]benzamide | m/z 532.4 (M + H)+ |

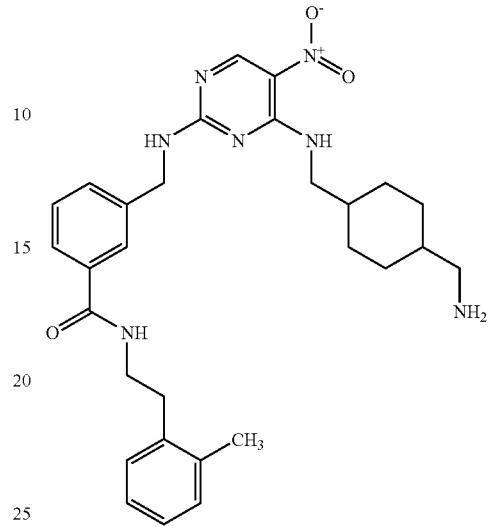

| | |
|---|---|
| (1S,2R)-2-({[4-({[4-(aminomethyl)cyclohexyl]methyl}amino)-5-nitropyrimidin-2-yl]amino}methyl)cyclohexanol | m/z 393.4 (M + H)+ |

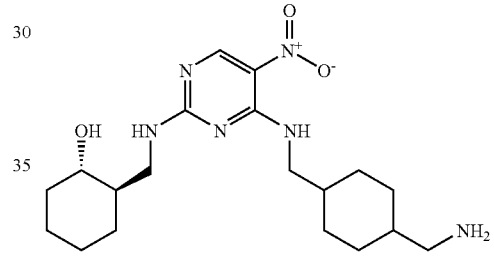

| | |
|---|---|
| (1R,2R)-2-({[4-({[4-(aminomethyl)cyclohexyl]methyl}amino)-5-nitropyrimidin-2-yl]amino}methyl)cyclohexanol | m/z 393.4 (M + H)+ |

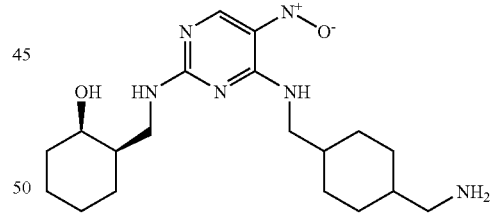

| | |
|---|---|
| methyl 4-({[4-(aminomethyl)cyclohexyl]methyl}amino)-2-[(2-chlorobenzyl)amino]pyrimidine-5-carboxylate | m/z 418.40 (M + H)+ |

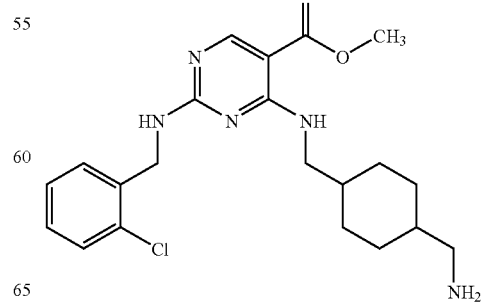

| | |
|---|---|
| 4-{[4-({[4-(aminomethyl)cyclohexyl]methyl}amino)-5-nitropyrimidin-2-yl]amino}-N-[2-(2-methylphenyl)ethyl]butanamide | m/z 484.5 (M + H)+ |

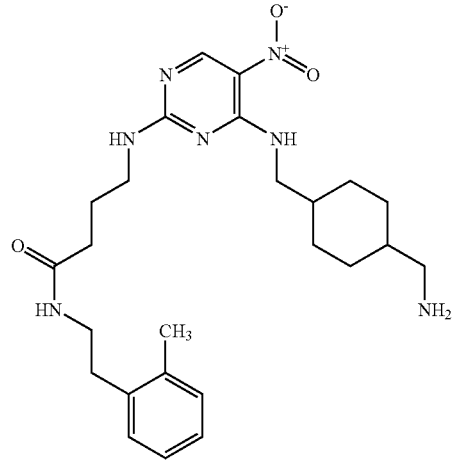

| | |
|---|---|
| 5-{[4-({[4-(aminomethyl)cyclohexyl]methyl}amino)-5-nitropyrimidin-2-yl]amino}-N-[2-(2-methylphenyl)ethyl]pentanamide | m/z 498.4 (M + H)+ |

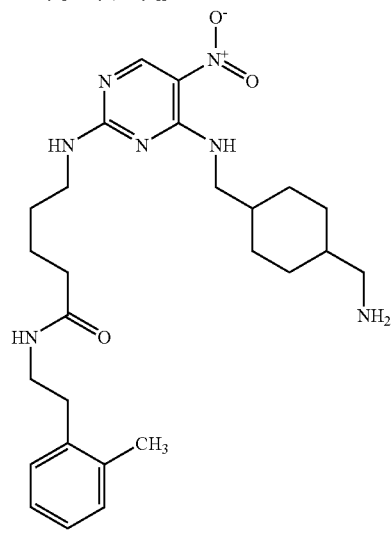

| | |
|---|---|
| 6-{[4-({[4-(aminomethyl)cyclohexyl]methyl}amino)-5-nitropyrimidin-2-yl]amino}-N-[2-(2-methylphenyl)ethyl]hexanamide | m/z 512.5 (M + H)+ |

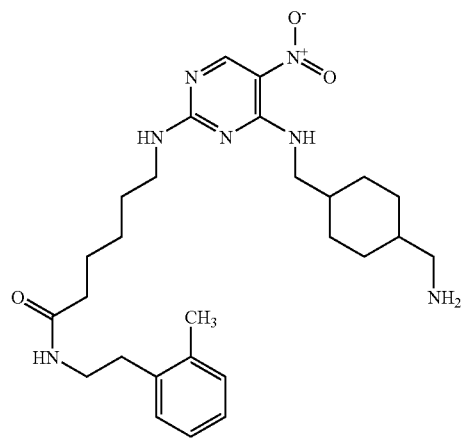

| | |
|---|---|
| (1R,3R)-3-({[4-({[4-(aminomethyl)cyclohexyl]methyl}amino)-5-nitropyrimidin-2-yl]amino}methyl)-4,4-dimethylcyclohexanol | m/z 421.5 (M + H)+ |

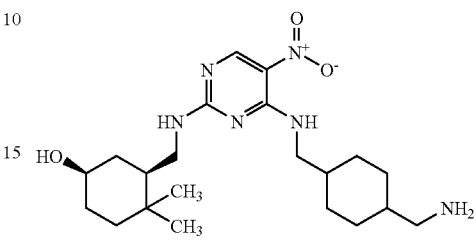

| | |
|---|---|
| $N^4$-({4-cis-[(dimethylamino)methyl]cyclohexyl}methyl)-$N^2$-(1-naphthylmethyl)-5-nitropyrimidine-2,4-diamine | m/z 449.11 (M + H)+ |

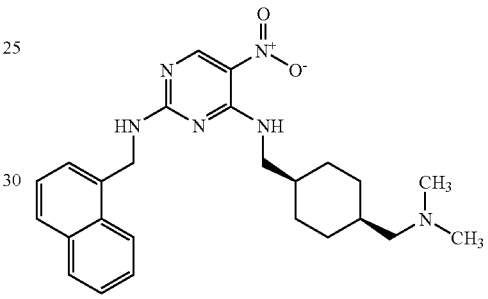

| | |
|---|---|
| $N^2$-[2-(methylthio)benzyl]-5-nitro-$N^4$-(piperidin-4-ylmethyl)pyrimidine-2,4-diamine | m/z 389.16 (M + H)+ |

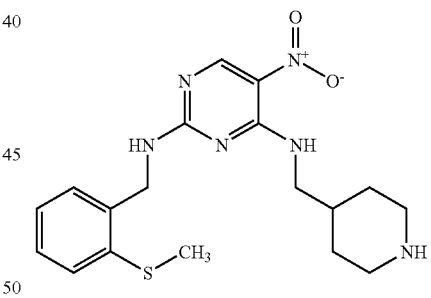

| | |
|---|---|
| 5-nitro-$N^4$-(piperidin-4-ylmethyl)-$N^2$-{2-[(trifluoromethyl)thio]benzyl}pyrimidine-2,4-diamine | m/z 443.11 (M + H)+ |

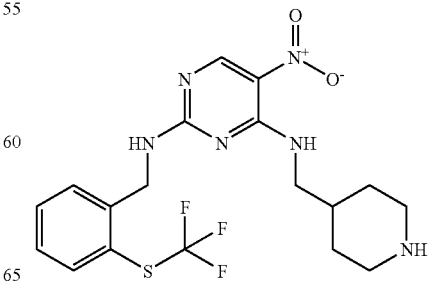

| | |
|---|---|
| $N^2$-(1-naphthylmethyl)-5-nitro-$N^4$-(piperidin-4-ylmethyl)pyrimidine-2,4-diamine 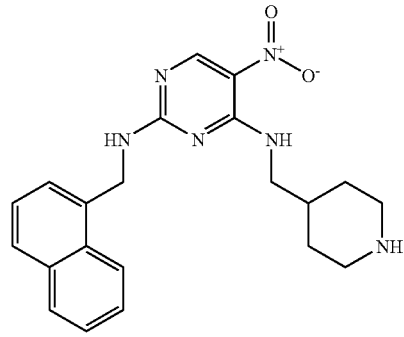 | m/z 393.23 (M + H)+ |
| $N^4$-({4-[(dimethylamino)methyl]cyclohexyl}methyl)-$N^2$-[2-(methylthio)benzyl]-5-nitropyrimidine-2,4-diamine 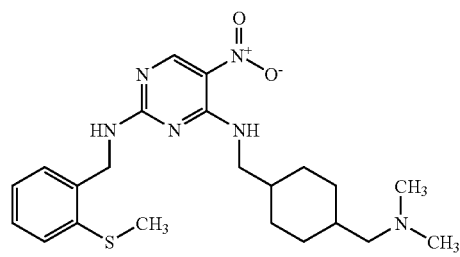 | m/z 445.5 (M + H)+ |
| $N^4$-({4-[(dimethylamino)methyl]cyclohexyl}methyl)-5-nitro-$N^2$-{2-[(trifluoromethyl)thio]benzyl}pyrimidine-2,4-diamine 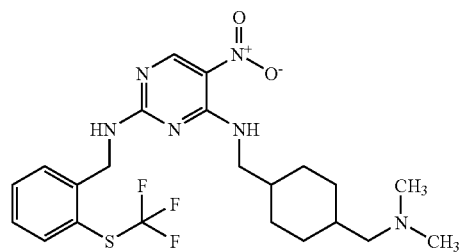 | m/z 499.5 (M + H)+ |
| $N^4$-({4-[(dimethylamino)methyl]cyclohexyl}methyl)-$N^2$-(1-naphthylmethyl)-5-nitropyrimidine-2,4-diamine 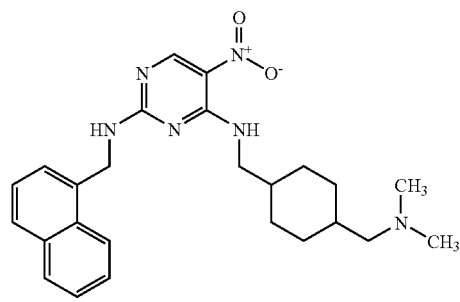 | m/z 449.34 (M + H)+ |
| $N^4$-{4-[(dimethylamino)methyl]benzyl}-$N^2$-[2-(methylthio)benzyl]-5-nitropyrimidine-2,4-diamine 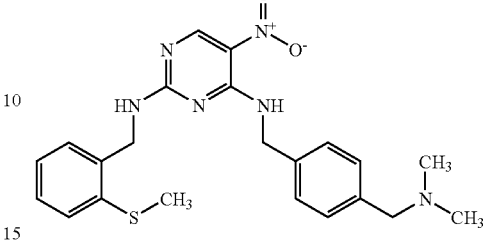 | m/z 439.24 (M + H)+ |
| $N^4$-{4-[(dimethylamino)methyl]benzyl}-5-nitro-$N^2$-{2-[(trifluoromethyl)thio]benzyl}pyrimidine-2,4-diamine 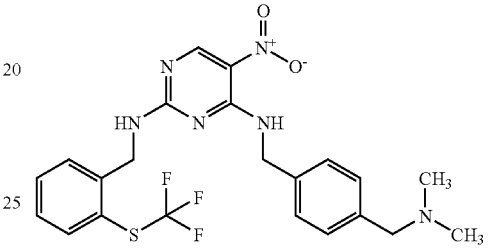 | m/z 493.20 (M + H)+ |
| $N^4$-{4-[(dimethylamino)methyl]benzyl}-$N^2$-(1-naphthylmethyl)-5-nitropyrimidine-2,4-diamine 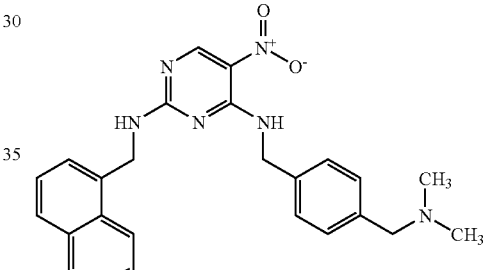 | m/z 443.28 (M + H)+ |
| $N^4$-[(1-methylpiperidin-4-yl)methyl]-$N^2$-[2-(methylthio)benzyl]-5-nitropyrimidine-2,4-diamine 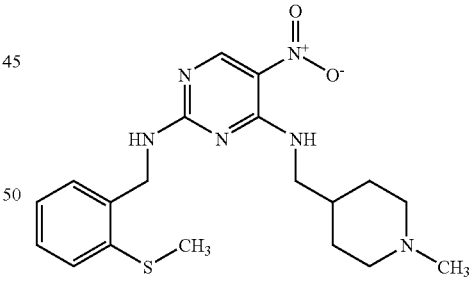 | m/z 403.26 (M + H)+ |
| $N^4$-[(1-methylpiperidin-4-yl)methyl]-5-nitro-$N^2$-{2-[(trifluoromethyl)thio]benzyl}pyrimidine-2,4-diamine 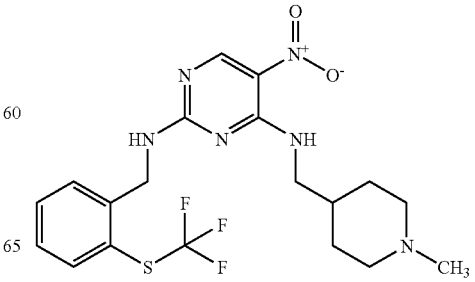 | m/z 457.24 (M + H)+ |

N⁴-[(1-methylpiperidin-4-yl)methyl]-N²-(1-naphthylmethyl)-5-nitropynmidine-2,4-diamine    m/z 407.38 (M + H)⁺

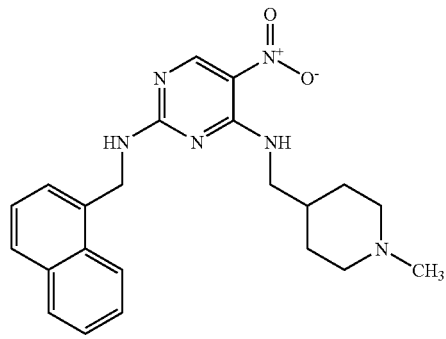

N²-(2-chlorobenzyl)-N⁴-[(1-methylpiperidin-4-yl)methyl]-5-nitropynmidine-2,4-diamine    m/z 391.2 (M + H)⁺

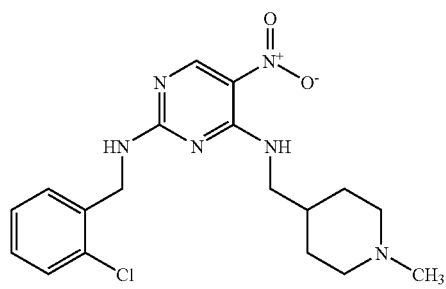

N²-(2-methoxybenzyl)-N⁴-[(1-methylpiperidin-4-yl)methyl]-5-nitropyrimidine-2,4-diamine    m/z 387.5 (M + H)⁺

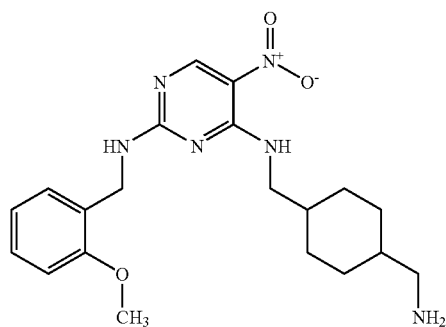

N⁴-{[4-(aminomethyl)cyclohexyl]methyl}-N²-(2-methoxybenzyl)-5-nitropyrimidine-2,4-diamine    m/z 401.6 (M + H)⁺

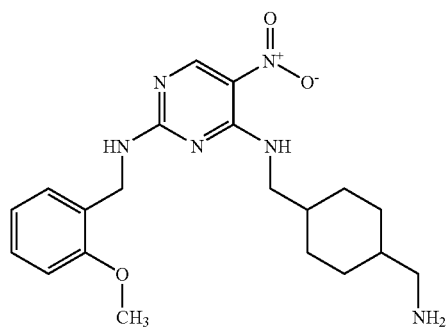

N⁴-{[4-(aminomethyl)cyclohexyl]methyl}-5-nitro-N²-[2-(trifluoromethyl)benzyl]pyrimidine-2,4-diamine    m/z 439.6 (M + H)⁺

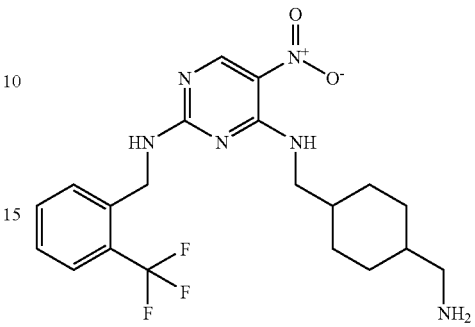

N⁴-{[4-(aminomethyl)cyclohexyl]methyl}-N²-(2,4-dichlorobenzyl)-5-nitropyrimidine-2,4-diamine    m/z 439.1 (M + H)⁺

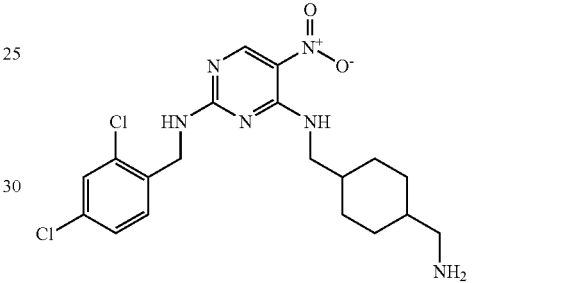

N⁴-{[4-(aminomethyl)cyclohexyl]methyl}-N²-(3-methoxybenzyl)-5-nitropyrimidine-2,4-diamine    m/z 401.6 (M + H)⁺

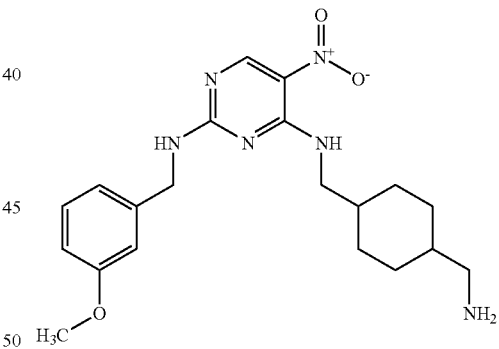

N⁴-{[4-(aminomethyl)cyclohexyl]methyl}-N²-[4-fluoro-2-(trifluoromethyl)benzyl]-5-nitropyrimidine-2,4-diamine    m/z 457.7 (M + H)⁺

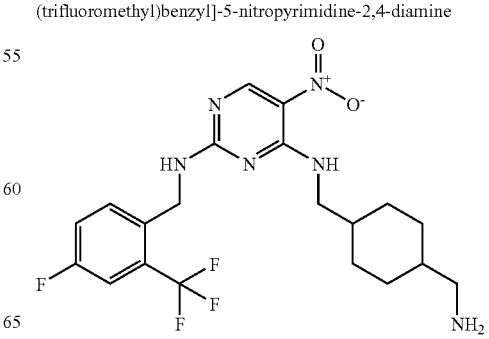

-continued

N⁴-{[4-(aminomethyl)cyclohexyl]methyl}-N²-(3-methylbenzyl)-5-nitropyrimidine-2,4-diamine    m/z 385.6 (M + H)⁺

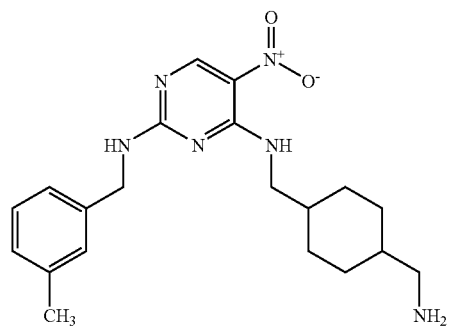

N⁴-{[4-(aminomethyl)cyclohexyl]methyl}-5-nitro-N²-(pyridin-2-ylmethyl)pyrimidine-2,4-diamine    m/z 372.5 (M + H)⁺

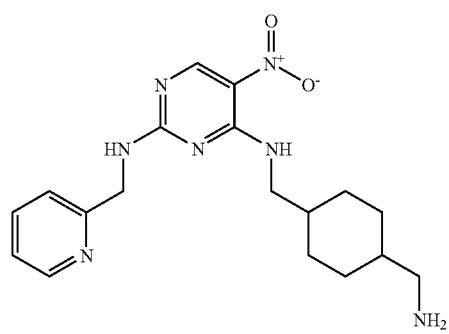

N⁴-{[4-(aminomethyl)cyclohexyl]methyl}-N²-(3-chlorobenzyl)-5-nitropyrimidine-2,4-diamine    m/z 403.2 (M − H)⁺

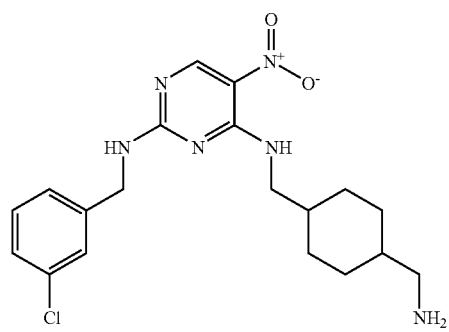

N⁴-{[4-(aminomethyl)cyclohexyl]methyl}-N²-(4-chlorobenzyl)-5-nitropyrimidine-2,4-diamine    m/z 403.2 (M − H)⁺

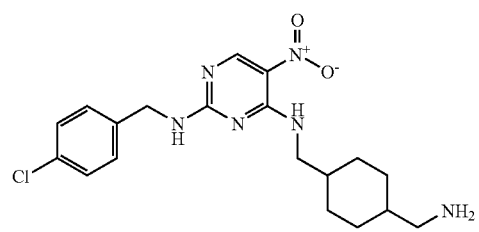

N⁴-{[4-(aminomethyl)cyclohexyl]methyl}-N²-(4-bromobenzyl)-5-nitropyrimidine-2,4-diamine    m/z 449.1 (M − H)⁺

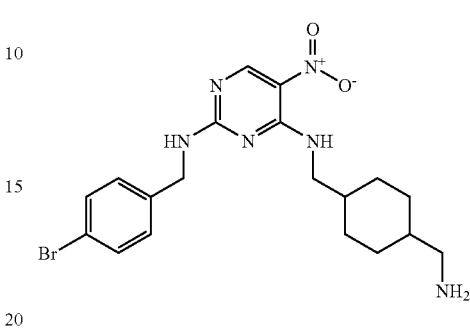

N⁴-{[4-(aminomethyl)cyclohexyl]methyl}-N²-(2,4-dimethoxybenzyl)-5-nitropyrimidine-2,4-diamine    m/z 431.4 (M + H)⁺

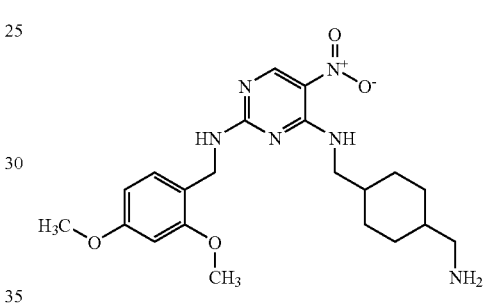

N⁴-{[4-(aminomethyl)cyclohexyl]methyl}-N²-[2-chloro-5-(trifluoromethyl)benzyl]-5-nitropyrimidine-2,4-diamine    m/z 471.2 (M − H)⁺

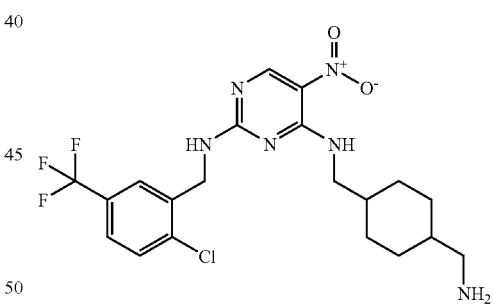

N⁴-{[4-(aminomethyl)cyclohexyl]methyl}-N²-(2,5-dichlorobenzyl)-5-nitropyrimidine-2,4-diamine    m/z 437.2 (M − H)⁺

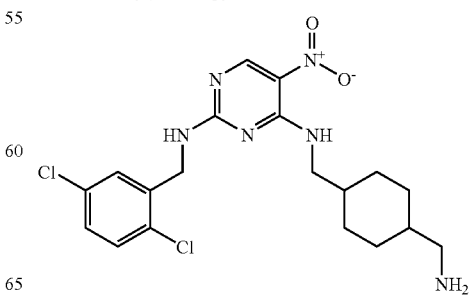

-continued

N[4]-{[4-(aminomethyl)cyclohexyl]methyl}-5-nitro-N[2]-[2-(trifluoromethoxy)benzyl]pyrimidine-2,4-diamine    m/z 455.5 (M + H)+

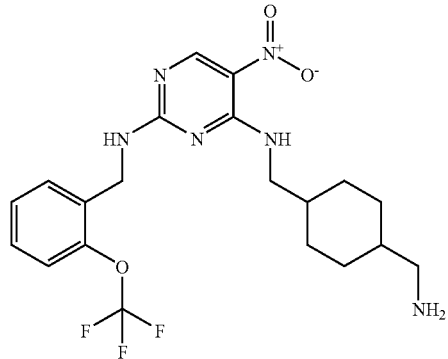

N[4]-{[4-(aminomethyl)cyclohexyl]methyl}-N[2]-(2-chloro-6-methylbenzyl)-5-nitropyrimidine-2,4-diamine    m/z 417.2 (M − H)+

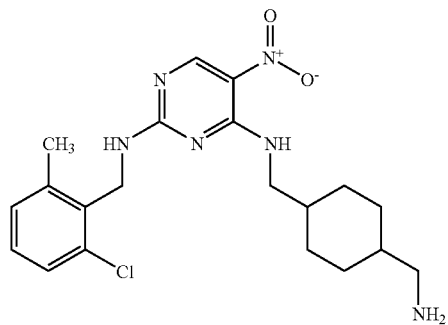

N[4]-{[4-(aminomethyl)cyclohexyl]methyl}-N[2]-(2,3-dichlorobenzyl)-5-nitropyrimidine-2,4-diamine    m/z 437.1 (M − H)+

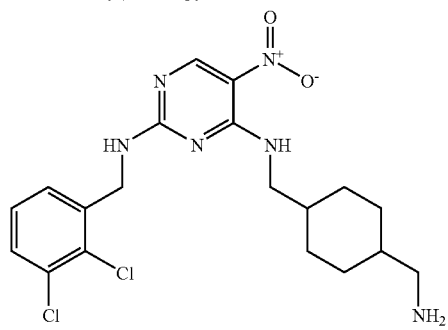

N[4]-{[4-(aminomethyl)cyclohexyl]methyl}-N[2]-(2-furylmethyl)-5-nitropyrimidine-2,4-diamine    m/z 361.2 (M + H)+

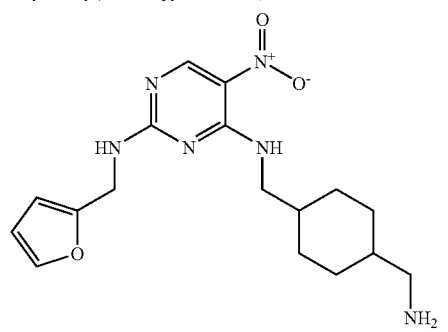

-continued

N[4]-{[4-(aminomethyl)cyclohexyl]methyl}-5-nitro-N[2]-(thien-2-ylmethyl)pyrimidine-2,4-diamine    m/z 377.3 (M + H)+

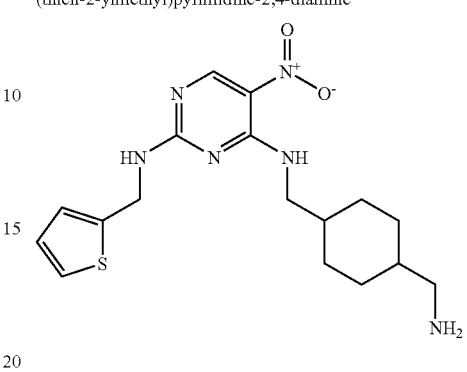

N[4]-{[4-(aminomethyl)cyclohexyl]methyl}-N[2]-(2-chlorobenzyl)-5-methylpyrimidine-2,4-diamine    m/z 374 (M + H)+

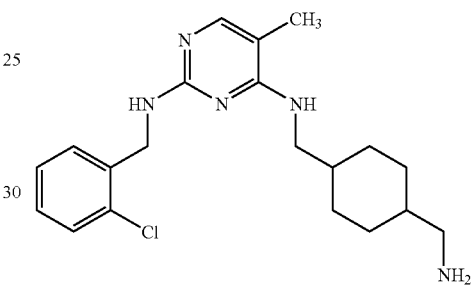

N[4]-(6-aminohexyl)-N[2]-(2-chlorobenzyl)-5-nitropyrimidine-2,4-diamine    m/z 378 (M + H)+

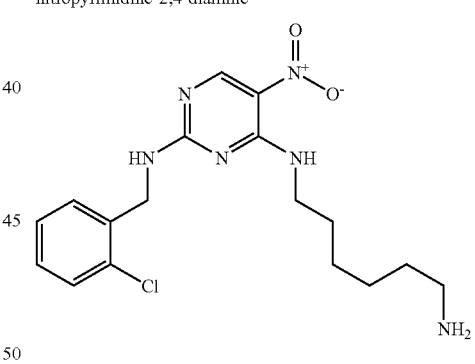

N-[4-(aminomethyl)benzyl]-N[2]-(2-chlorobenzyl)-5-nitropyrimidine-2,4-diamine    m/z 397 (M − H)+

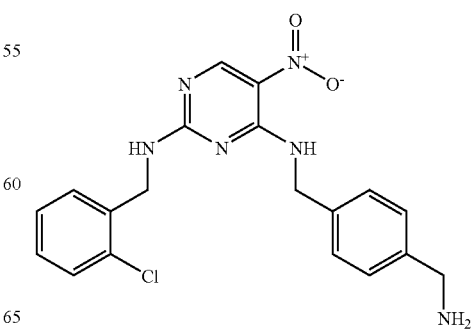

-continued $N^4$-(7-aminoheptyl)-$N^2$-(2-chlorobenzyl)-5-nitropyrimidine-2,4-diamine    m/z 393 (M + H)⁺

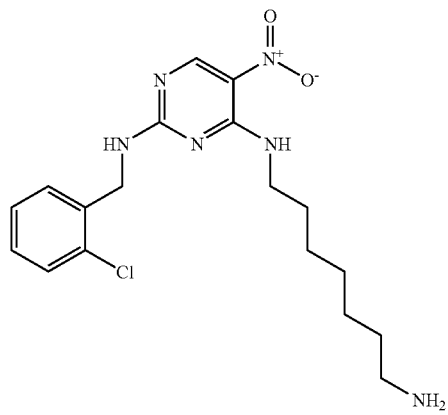

$N^4$-{[3-(aminomethyl)cyclohexyl]methyl}-$N^2$-(2-chlorobenzyl)-5-nitropyrimidine-2,4-diamine    m/z 404 (M + H)⁺

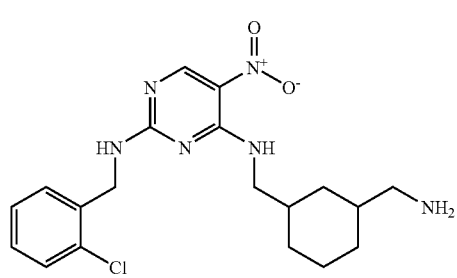

$N^4$-{[4-(aminomethyl)cyclohexyl]methyl}-$N^2$-(1-methyl-1-phenylethyl)-5-nitropyrimidine-2,4-diamine    m/z 399.08 (M + H)⁺

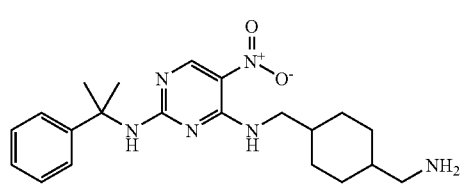

4-(4,4'-bipiperidin-1-yl)-N-(2-chlorobenzyl)-5-nitropyrimidin-2-amine    m/z 431 (M + H)⁺

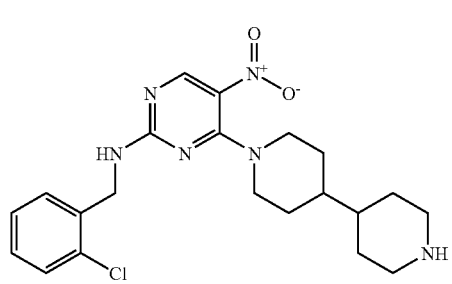

-continued $N^2$-(2-chlorobenzyl)-$N^4$-({4-[(dimethylamino)methyl]cyclohexyl}methyl)-5-nitropyri    m/z 431 (M − H)⁺

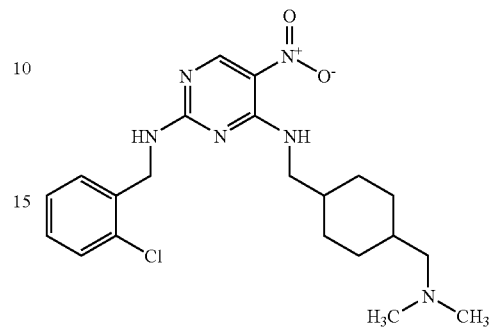

$N^4$-{[4-(aminomethyl)cyclohexyl]methyl}-$N^2$-(2,5-difluorobenzyl)-5-nitropyrimidine-2,4-diamine    m/z 407.5 (M + H)⁺

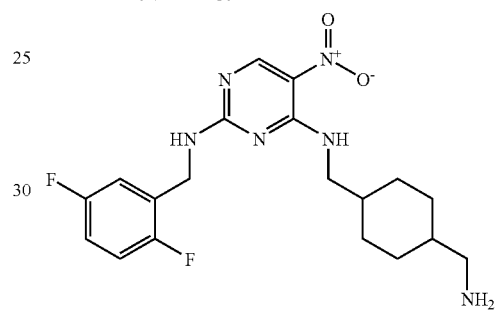

$N^4$-{[4-(aminomethyl)cyclohexyl]methyl}-$N^2$-[4-(difluoromethoxy)benzyl]-5-nitropyrimidine-2,4-diamine    m/z 437.6 (M + H)⁺

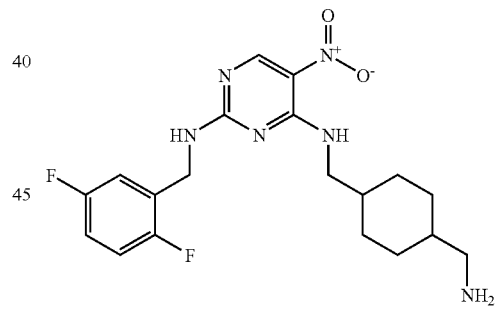

$N^4$-{[4-(aminomethyl)cyclohexyl]methyl}-$N^2$-(2-ethoxybenzyl)-5-nitropyrimidine-2,4-diamine    m/z 415.4 (M + H)⁺

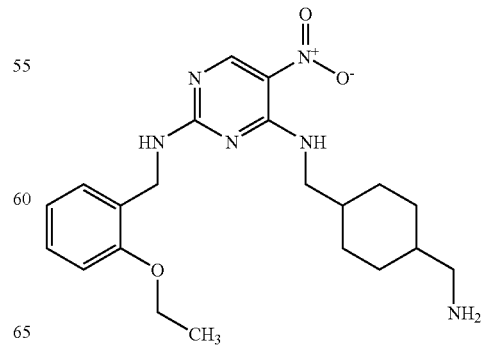

-continued

N⁴-{[4-(aminomethyl)cyclohexyl]methyl}-5-nitro-N²-[(1S)-1-phenylethyl]pyrimidine-2,4-diamine    m/z 385.5 (M + H)⁺

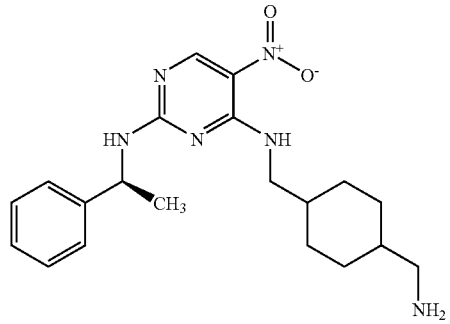

N⁴-{[4-(aminomethyl)cyclohexyl]methyl}-N²-(2-methylbenzyl)-5-nitropyrimidine-2,4-diamine    m/z 385.4 (M + H)⁺

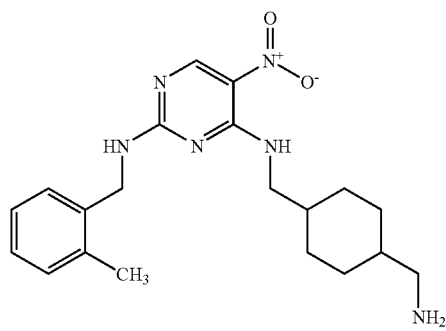

N⁴-{[4-(aminomethyl)cyclohexyl]methyl}-N²-(2-fluorobenzyl)-5-nitropyrimidine-2,4-diamine    m/z 389.3 (M + H)⁺

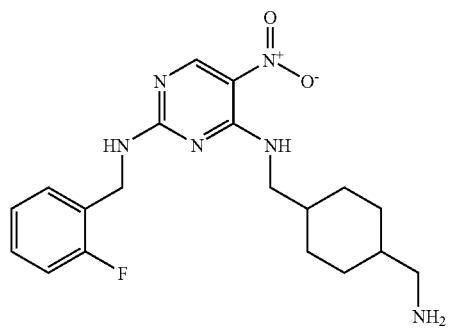

N⁴-{[4-(aminomethyl)cyclohexyl]methyl}-N²-(3-chloro-2-fluorobenzyl)-5-nitropyrimidine-2,4-diamine    m/z 423.2 (M + H)⁺

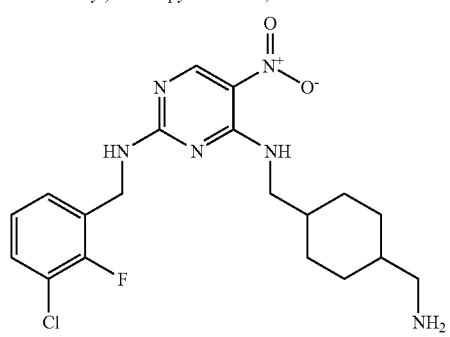

-continued

N⁴-{[4-(aminomethyl)cyclohexyl]methyl}-5-nitro-N²-(4-pentylbenzyl)pyrimidine-2,4-diamine    m/z 441.6 (M + H)⁺

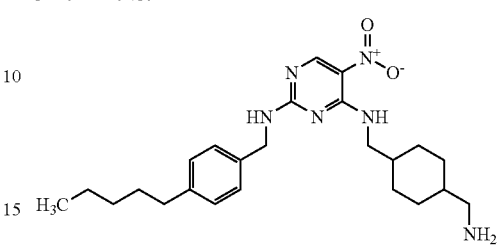

N⁴-{[4-(aminomethyl)cyclohexyl]methyl}-N²-(4-butoxybenzyl)-5-nitropyrimidine-2,4-diamine    m/z 443.4 (M + H)⁺

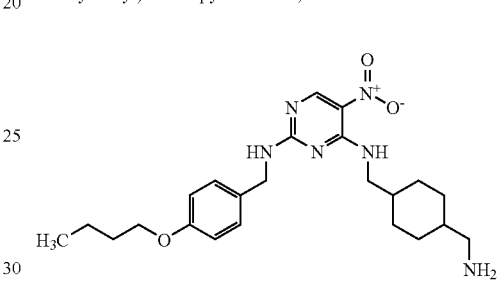

N⁴-{[4-(aminomethyl)cyclohexyl]methyl}-N²-(2,3-dimethoxybenzyl)-5-nitropynmidine-2,4-diamine    m/z 431.6 (M + H)⁺

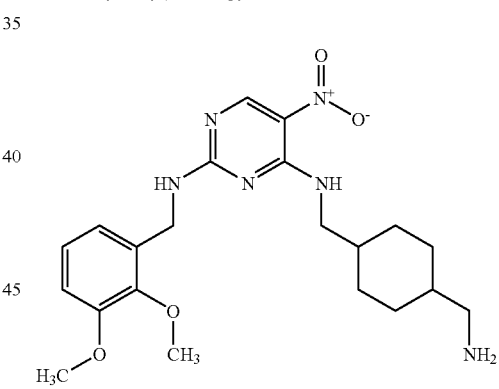

N⁴-{[4-(aminomethyl)cyclohexyl]methyl}-N²-(2,5-dimethoxybenzyl)-5-nitropyrimidine-2,4-diamine    m/z 431.5 (M + H)⁺

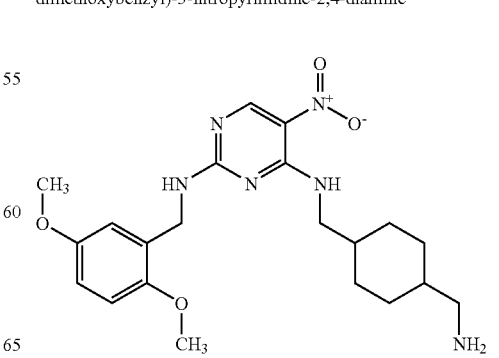

| | |
|---|---|
| N²-(2-chlorobenzyl)-N⁴-[7-(dimethylamino)heptyl]-5-nitropyrimidine-2,4-diamine | m/z 421 (M + H)⁺ |

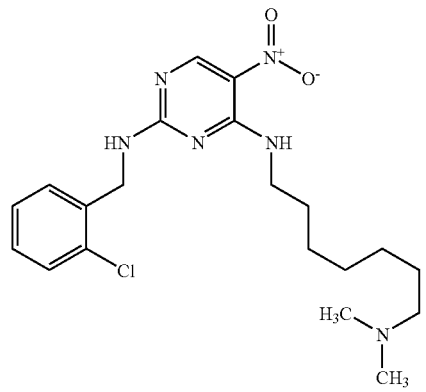

| | |
|---|---|
| N⁴-{[4-(aminomethyl)cyclohexyl]methyl}-N²-(1,1'-biphenyl-2-ylmethyl)-5-nitropyrimidine-2,4-diamine | m/z 447.10 (M + H)⁺ |

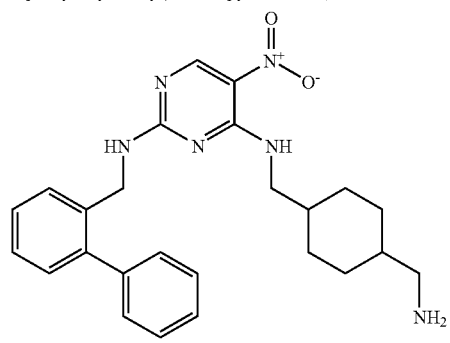

| | |
|---|---|
| N⁴-{[4-(aminomethyl)cyclohexyl]methyl}-N²-(4-fluorobenzyl)-5-nitropyrimidine-2,4-diamine | m/z 389.06 (M + H)⁺ |

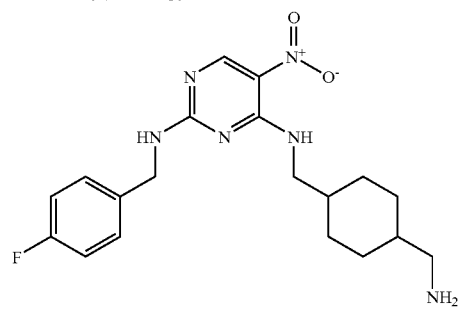

| | |
|---|---|
| N⁴-{[4-(aminomethyl)cyclohexyl]methyl}-N²-(2,4-difluorobenzyl)-5-nitropyrimidine-2,4-diamine | m/z 407.06 (M + H)⁺ |

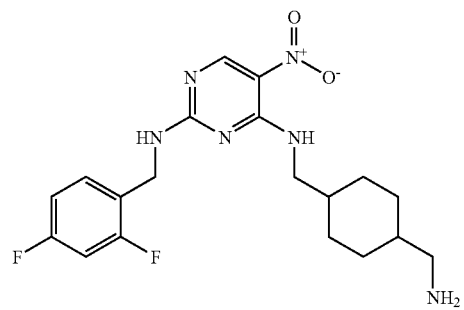

| | |
|---|---|
| N⁴-{[4-(aminomethyl)cyclohexyl]methyl}-N²-(3-fluoro-4-methylbenzyl)-5-nitropyrimidine-2,4-diamine | m/z 403.10 (M + H)⁺ |

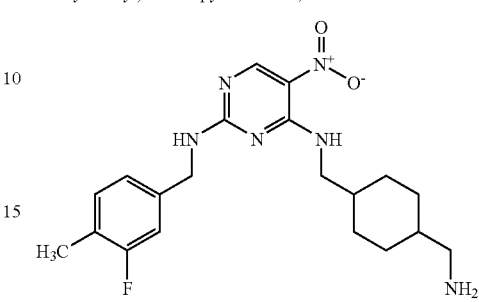

| | |
|---|---|
| N⁴-{[4-(aminomethyl)cyclohexyl]methyl}-N²-(2,3-difluorobenzyl)-5-nitropyrimidine-2,4-diamine | m/z 407.02 (M + H)⁺ |

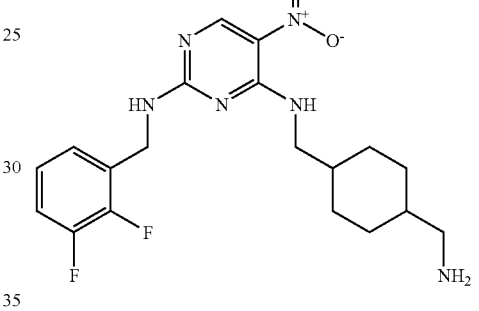

| | |
|---|---|
| N⁴-{[4-(aminomethyl)cyclohexyl]methyl}-5-bromo-N²-(2-chlorobenzyl)pyrimidine-2,4-diamine | m/z 439.90 (M + H)⁺ |

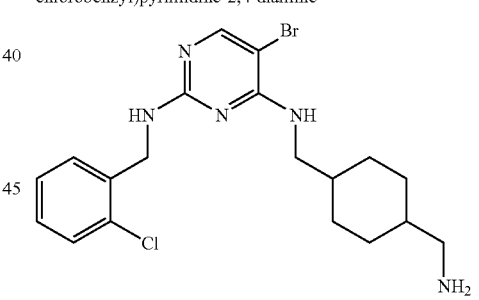

| | |
|---|---|
| N⁴-{[4-(aminomethyl)cyclohexyl]methyl}-N²-(2,6-dimethoxybenzyl)-5-nitropyrimidine-2,4-diamine | m/z 431.3 (M + H)⁺ |

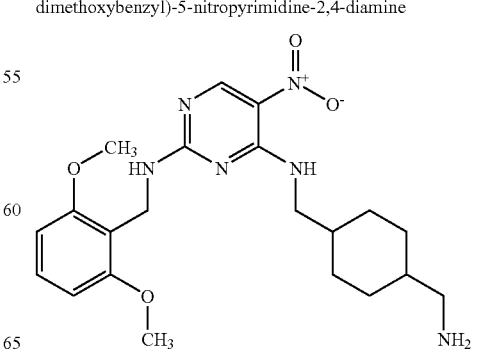

N⁴-{[4-(aminomethyl)cyclohexyl]methyl}-N²-(2,6-difluorobenzyl)-5-nitropyrimidine-2,4-diamine    m/z 407.3 (M + H)⁺

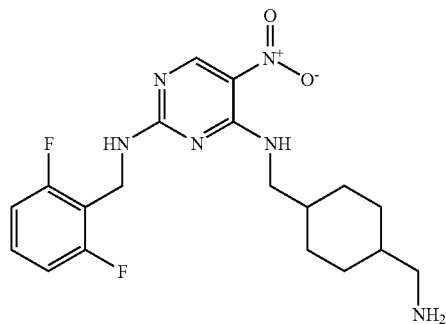

N⁴-{[4-(aminomethyl)cyclohexyl]methyl}-N²-[2-fluoro-3-(trifluoromethyl)benzyl]-5-nitropyrimidine-2,4-diamine    m/z 457.3 (M + H)⁺

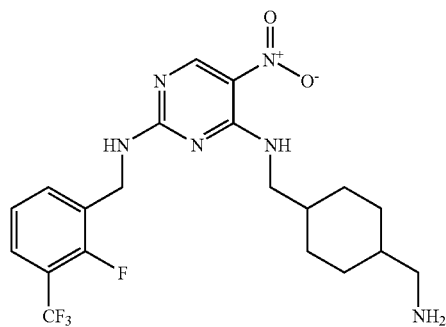

N⁴-{[4-(aminomethyl)cyclohexyl]methyl}-N²-(4-chloro-2-fluorobenzyl)-5-nitropyrimidine-2,4-diamine    m/z 423.2 (M + H)⁺

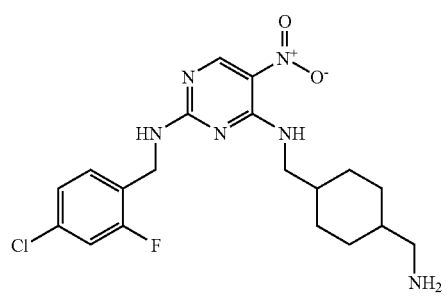

N⁴-{[4-(aminomethyl)cyclohexyl]methyl}-5-nitro-N²-(1-phenylcyclopropyl)pyrimidine-2,4-diamine    m/z 397.04 (M + H)⁺

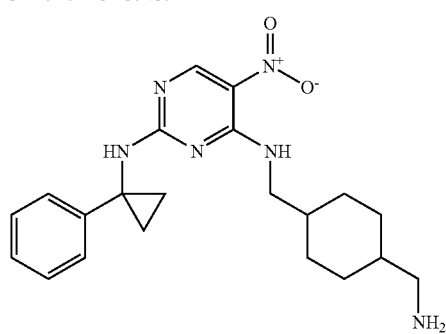

N⁴-{[4-(aminomethyl)cyclohexyl]methyl}-N²-[1-(2-chlorophenyl)-1-methylethyl]-5-nitropyrimidine-2,4-diamine    m/z 433.04 (M + H)⁺

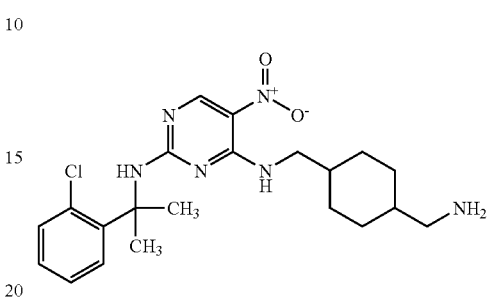

N⁴-{[4-(aminomethyl)cyclohexyl]methyl}-N²-(2,3-dihydro-1-benzofuran-5-ylmethyl)-5-nitropyrimidine-2,4-diamine    m/z 413.4 (M + H)⁺

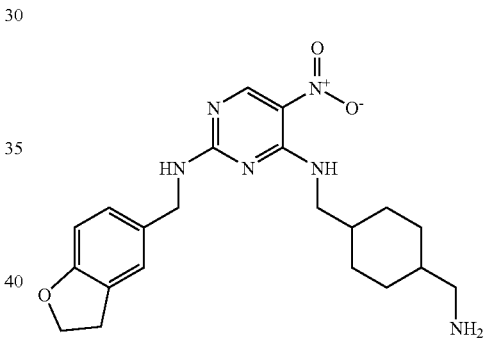

N⁴-{[4-(aminomethyl)cyclohexyl]methyl}-N²-[(1,5-dimethyl-1H-pyrrol-2-yl)methyl]-5-nitropyrimidine-2,4-diamine    m/z 388.4 (M + H)⁺

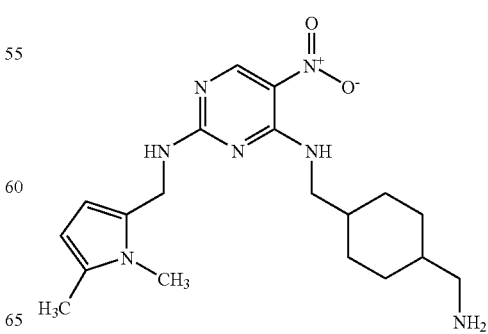

-continued

| | |
|---|---|
| $N^4$-{[4-(aminomethyl)cyclohexyl]methyl}-$N^2$-(2-bromobenzyl)-5-nitronyrimidine-2,4-diamine | m/z 450.9 (M + H)$^+$ |

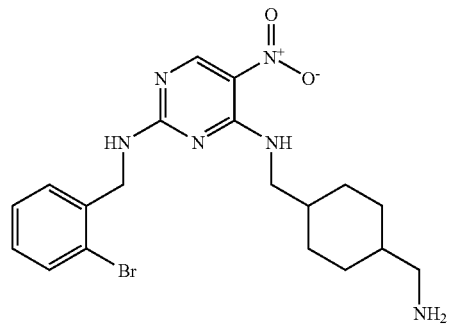

| | |
|---|---|
| $N^4$-{[4-(aminomethyl)cyclohexyl]methyl}-$N^2$-(2,3-dimethylbenzyl)-5-nitropyrimidine-2,4-diamine | m/z 399.14 (M + H)$^+$ |

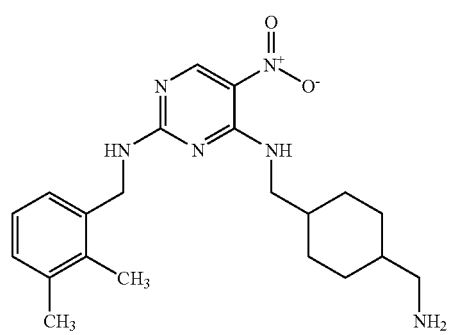

-continued

| | |
|---|---|
| $N^4$-{[4-(aminomethyl)cyclohexyl]methyl}-$N^2$-(2,4-dimethylbenzyl)-5-nitropyrimidine-2,4-diamine | m/z 399.18 (M + H)$^+$ |

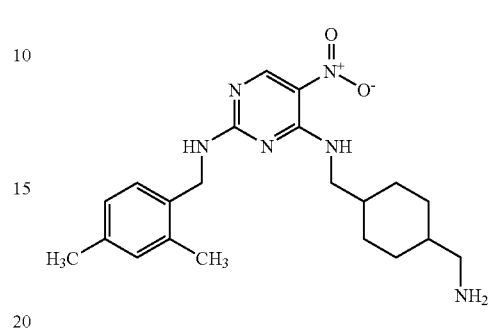

| | |
|---|---|
| $N^4$-{[4-(aminomethyl)cyclohexyl]methyl}-$N^2$-(2,5-dimethylbenzyl)-5-nitropyrimidine-2,4-diamine | m/z 399.13 (M + H)$^+$ |

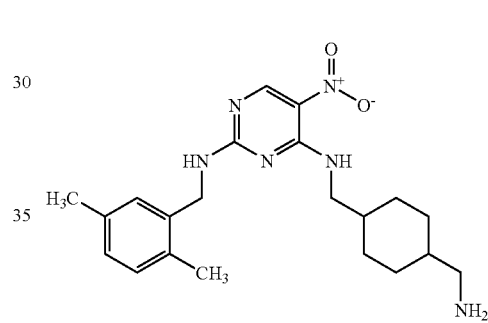

| | |
|---|---|
| $N^4$-{[4-(aminomethyl)cyclohexyl]methyl}-$N^2$-[2-fluoro-5-(trifluoromethyl)benzyl]-5-nitropyrimidine-2,4-diamine | m/z 457.17 (M + H)$^+$ |

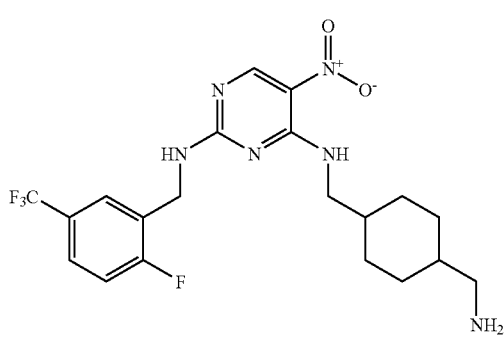

N$^4$-{[4-(aminomethyl)cyclohexyl]methyl}-N$^2$-[2-(methylthio)benzyl]-5-nitropyrimidine-2,4-diamine m/z 417.02 (M + H)$^+$

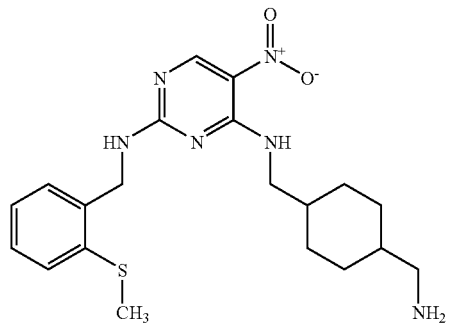

N$^4$-{[4-(aminomethyl)cyclohexyl]methyl}-5-nitro-N$^2$-{2-[(trifluoromethyl)thio]benzyl}pyrimidine-2,4-diamine m/z 470.96 (M + H)$^+$

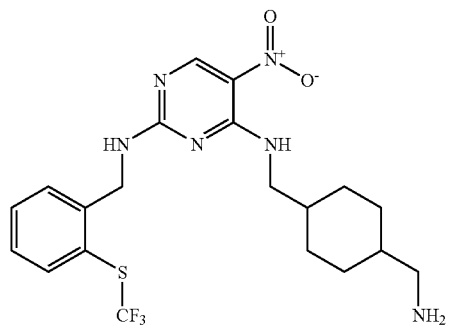

N$^4$-{[4-(aminomethyl)cyclohexyl]methyl}-N$^2$-(3-fluorobenzyl)-5-nitropyrimidine-2,4-diamine m/z 389.05 (M + H)$^+$

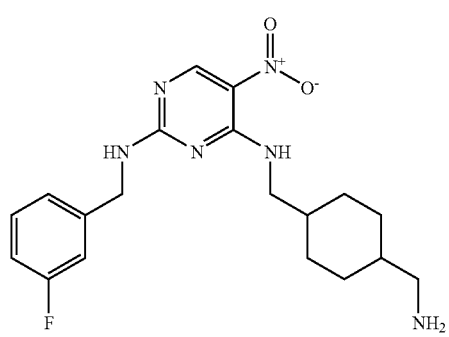

N$^4$-{[4-(aminomethyl)cyclohexyl]methyl}-N$^2$-(6-chloro-2-fluoro-3-methylbenzyl)-5-nitropyrimidine-2,4-diamine m/z 436.98 (M + H)$^+$

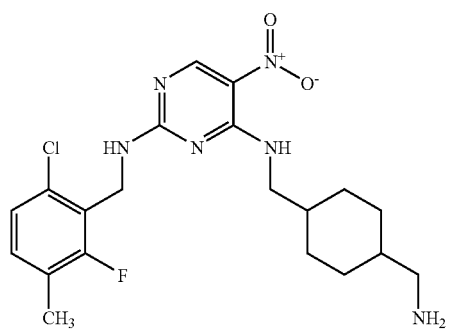

| | |
|---|---|
| $N^4$-{[4-(aminomethyl)cyclohexyl]methyl}-$N^2$-(2-chloro-6-fluoro-3-methylbenzyl)-5-nitropyrimidine-2,4-diamine | m/z 436.99 (M + H)⁺ |

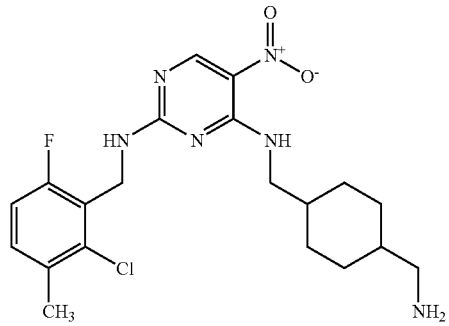

| | |
|---|---|
| $N^4$-{[4-(aminomethyl)cyclohexyl]methyl}-$N^2$-2-naphthyl-5-nitropyrimidine-2,4-diamine | m/z 407.2 (M + H)⁺ |

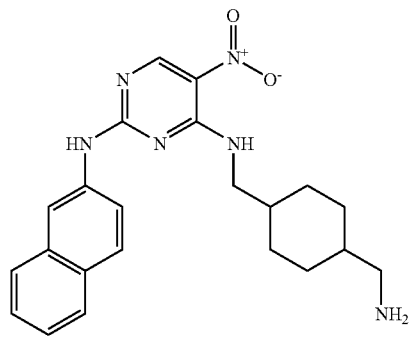

| | |
|---|---|
| $N^4$-{[4-(aminomethyl)cyclohexyl]methyl}-$N^2$-(1-naphthylmethyl)-5-nitropyrimidine-2,4-diamine | m/z 421.11 (M + H)⁺ |

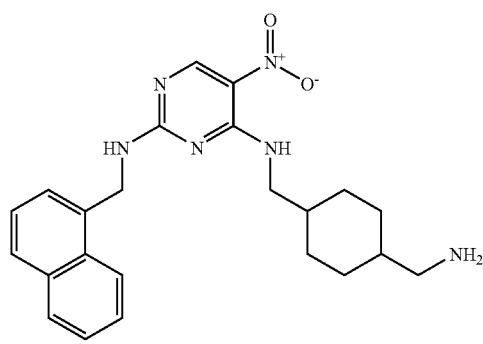

| | |
|---|---|
| $N^4$-{[4-(aminomethyl)cyclohexyl]methyl}-$N^2$-[2-fluoro-4-(trifluoromethyl)benzyl]-5-nitropyrimidine-2,4-diamine | m/z 457.5 (M + H)⁺ |

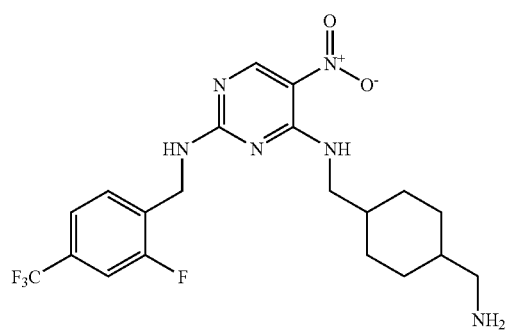

| | |
|---|---|
| N⁴-{[4-(aminomethyl)cyclohexyl]methyl}-N²-(4-chloro-2-methylbenzyl)-5-nitropyrimidine-2,4-diamine | m/z 419.4 (M + H)⁺ |

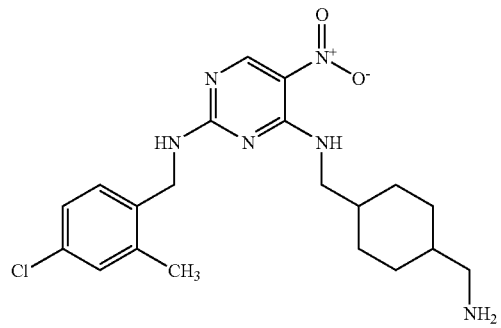

| | |
|---|---|
| N⁴-{[4-(aminomethyl)cyclohexyl]methyl}-N²-(5-chloro-2-methylbenzyl)-5-nitropyrimidine-2,4-diamine | m/z 419.3 (M + H)⁺⁾ |

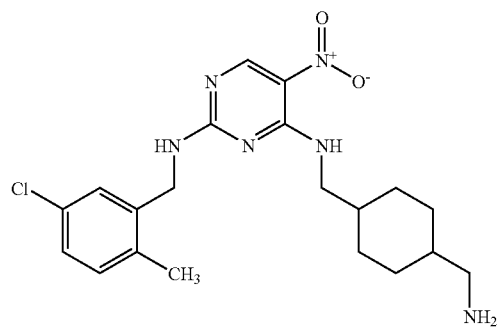

| | |
|---|---|
| N⁴-{[4-(aminomethyl)cyclohexyl]methyl}-N²-(3-chloro-2-methylbenzyl)-5-nitropyrimidine-2,4-diamine | m/z 419.3 (M + H)⁺ |

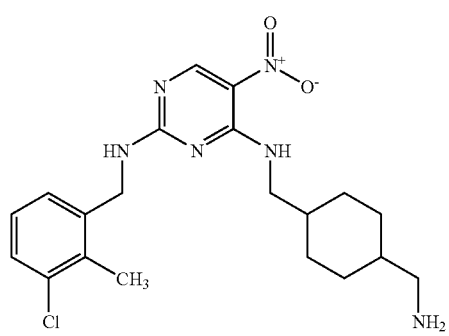

| | |
|---|---|
| N⁴-{[4-(aminomethyl)cyclohexyl]methyl}-N²-[5-fluoro-2-(trifluoromethyl)benzyl]-5-nitropyrimidine-2,4-diamine | m/z 457.12 (M + H)⁺ |

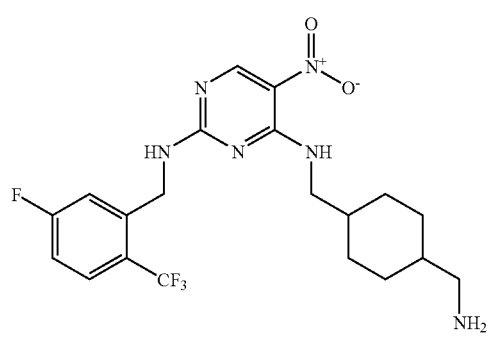

| | |
|---|---|
| $N^4$-{[4-(aminomethyl)cyclohexyl]methyl}-$N^2$-(5-chloro-2-fluorobenzyl)-5-nitropyrimidine-2,4-diamine | m/z 423.01 (M + H)$^+$ |

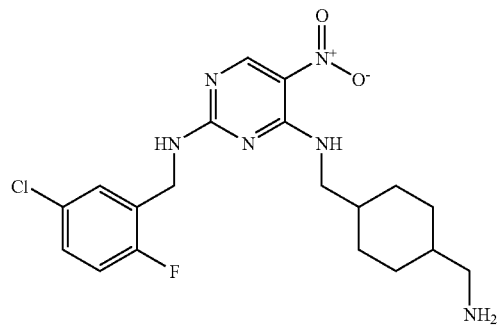

| | |
|---|---|
| $N^4$-{[4-(aminomethyl)cyclohexyl]methyl}-$N^2$-(2,3-difluoro-4-methylbenzyl)-5-nitropyrimidine-2,4-diamine | m/z 421.15 (M + H)$^+$ |

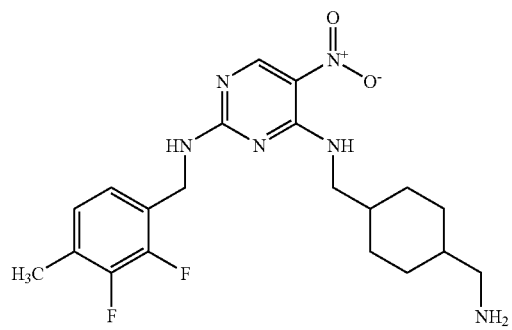

| | |
|---|---|
| $N^4$-{[4-(aminomethyl)cyclohexyl]methyl}-$N^2$-(5-fluoro-2-methylbenzyl)-5-nitropyrimidine-2,4-diamine | m/z 403.10 (M + H)$^+$ |

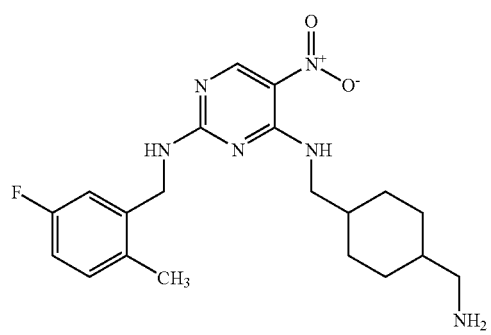

| | |
|---|---|
| $N^4$-{[4-(aminomethyl)cyclohexyl]methyl}-$N^2$-1-naphthyl-5-nitropyrimidine-2,4-diamine | m/z 407.0 (M + H)$^+$ |

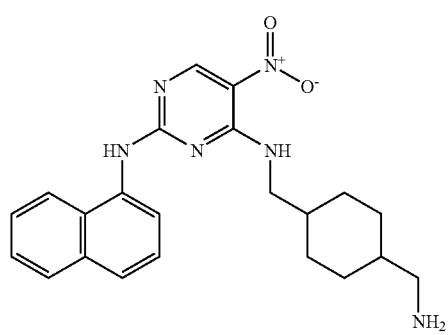

| | |
|---|---|
| {4-trans-[({2-[(2-chlorobenzyl)amino]-5-nitropyrimidin-4-yl}amino)methyl]cyclohexyl}methanol | m/z 406.05 (M + H)+ |
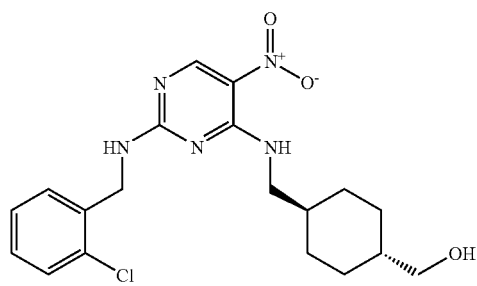
| | |
|---|---|
| N4-{[4-(aminomethyl)cyclohexyl]methyl}-5-bromo-N2-(2,5-dichlorobenzyl)pyrimidine-2,4-diamine | m/z 474.0 (M + H)+ |
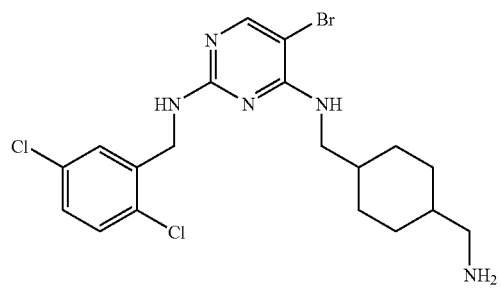
| | |
|---|---|
| N4-{[4-(aminomethyl)cyclohexyl]methyl}-5-bromo-N2-(2,4-dichlorobenzyl)pyrimidine-2,4-diamine | m/z 473.30 (M + H)+ |
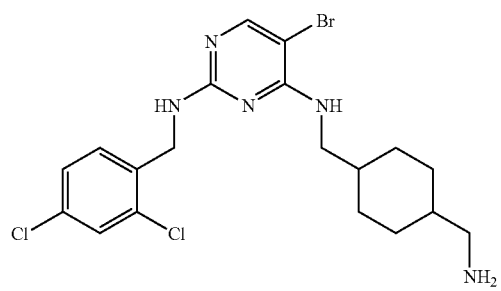
| | |
|---|---|
| N4-{[4-(aminomethyl)cyclohexyl]methyl}-5-bromo-N2-(2-bromobenzyl)pyrimidine-2,4-diamine | m/z 484.10 (M + H)+ |
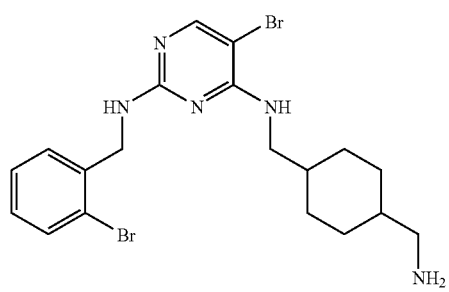

| | |
|---|---|
| $N^4$-{[4-(aminomethyl)cyclohexyl]methyl}-$N^2$-(cyclohexylmethyl)-5-nitropyrimidine-2,4-diamine | m/z 372 (M + H)$^+$ |

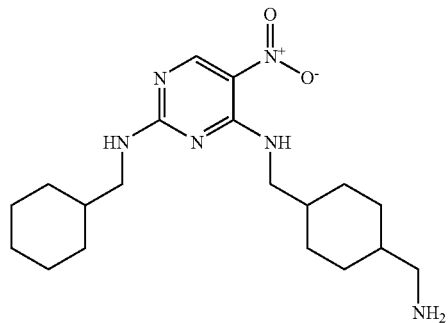

| | |
|---|---|
| $N^4$-{[4-(aminomethyl)cyclohexyl]methyl}-$N^2$-(2-naphthylmethyl)-5-nitropyrimidine-2,4-diamine | m/z 421.1 (M + H)$^+$ |

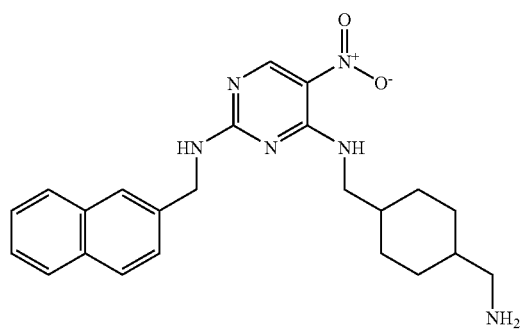

| | |
|---|---|
| $N^4$-{[4-(aminomethyl)cyclohexyl]methyl}-5-bromo-$N^2$-[2-(trifluoromethoxy)benzyl]pyrimidine-2,4-diamine | m/z 489.90 (M + H)$^+$ |

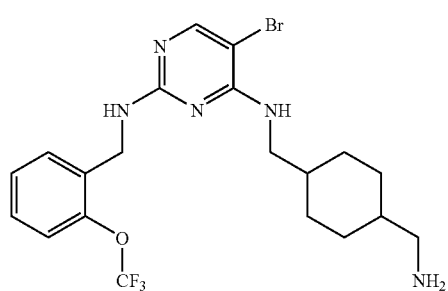

| | |
|---|---|
| $N^4$-{[4-(aminomethyl)cyclohexyl]methyl}-5-bromo-$N^2$-[2-(trifluoromethyl)benzyl]pyrimidine-2,4-diamine | m/z 473.20 (M + H)$^+$ |

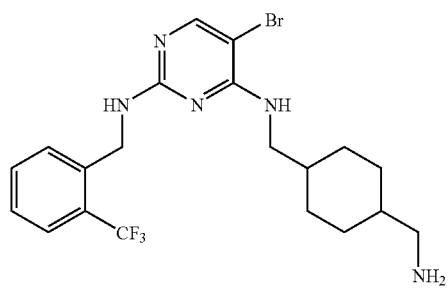

| | |
|---|---|
| $N^4$-{[4-(aminomethyl)cyclohexyl]methyl}-$N^2$-[2-(difluoromethoxy)benzyl]-5-nitropyrimidine-2,4-diamine | m/z 437 (M + H)$^+$ |
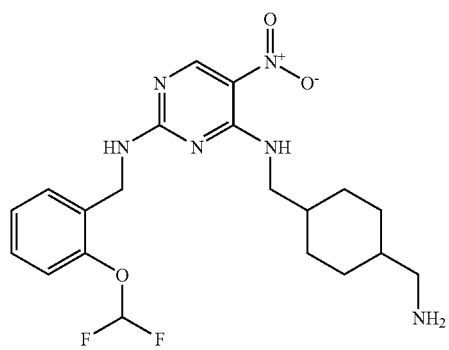
| | |
|---|---|
| $N^4$-{[4-(aminomethyl)cyclohexyl]methyl}-$N^2$-[3-(difluoromethoxy)benzyl]-5-nitropyrimidine-2,4-diamine | m/z 437.3 (M + H)$^+$ |
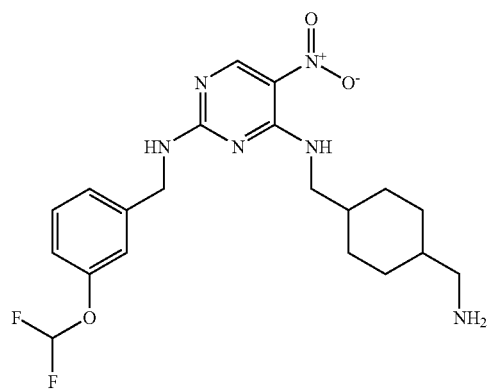
| | |
|---|---|
| $N^4$-{[4-(aminomethyl)cyclohexyl]methyl}-$N^2$-(2-chloro-4-fluorobenzyl)-5-nitropyrimidine-2,4-diamine | m/z 423.3 (M + H)$^+$ |
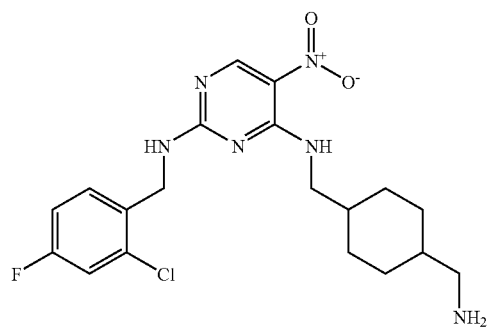

| | |
|---|---|
| $N^4$-{[4-(aminomethyl)cyclohexyl]methyl}-$N^2$-(2-chloro-3,6-difluorobenzyl)-5-nitropyrimidine-2,4-diamine | m/z 441.2 (M + H)$^+$ |

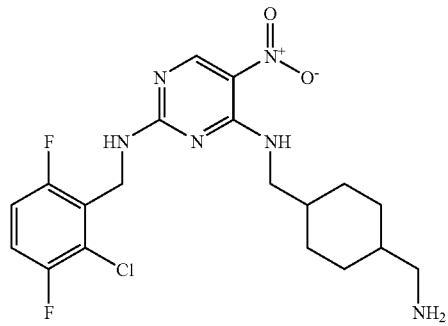

| | |
|---|---|
| $N^4$-{[4-(aminomethyl)cyclohexyl]methyl}-5-nitro-$N^2$-(2,3,5-trifluorobenzyl)pyrimidine-2,4-diamine | m/z 425.3 (M + H)$^+$ |

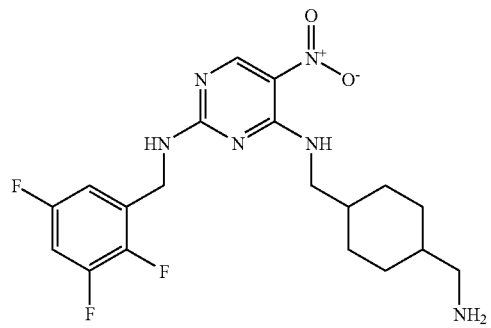

| | |
|---|---|
| $N^4$-{[4-(aminomethyl)cyclohexyl]methyl}-5-nitro-$N^2$-(2,3,4,5-tetrafluorobenzyl)pyrimidine-2,4-diamine | m/z 443.3 (M + H)$^+$ |

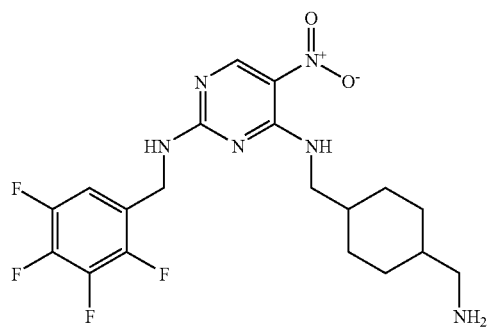

| | |
|---|---|
| $N^4$-{[4-(aminomethyl)cyclohexyl]methyl}-5-nitro-$N^2$-[(1R)-1-phenylethyl]pyrimidine-2,4-diamine | m/z 385.3 (M + H)$^+$ |

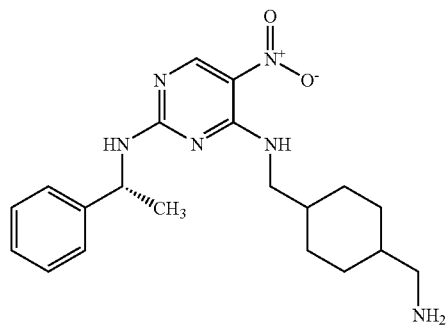

| | |
|---|---|
| $N^4$-{[4-(aminomethyl)cyclohexyl]methyl}-$N^2$-2,3-dihydro-1H-inden-2-yl-5-nitropyrimidine-2,4-diamine | m/z 397.3 (M + H)$^+$ |

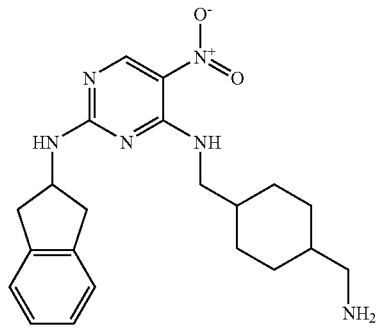

| | |
|---|---|
| $N^4$-{[4-(aminomethyl)cyclohexyl]methyl}-$N^2$-[(1S)-2,3-dihydro-1H-inden-1-yl]-5-nitropyrimidine-2,4-diamine | m/z 397.4 (M + H)$^+$ |

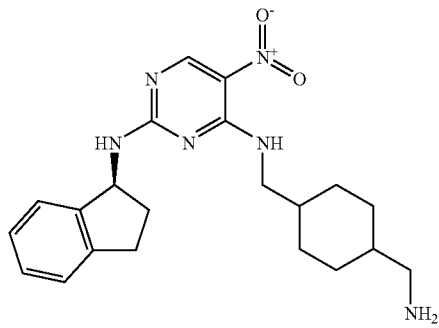

| | |
|---|---|
| $N^4$-{[4-(aminomethyl)cyclohexyl]methyl}-$N^2$-[(1R)-2,3-dihydro-1H-inden-1-yl]-5-nitropyrimidine-2,4-diamine | m/z 397.4 (M + H)$^+$ |

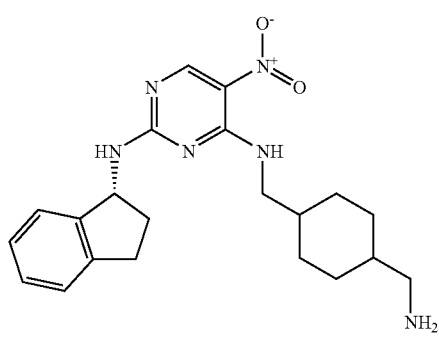

| | |
|---|---|
| $N^4$-{[4-(aminomethyl)cyclohexyl]methyl}-$N^2$-(4-chloro-1-naphthyl)-5-nitropyrimidine-2,4-diamine | m/z 441.3 (M + H)$^+$ |

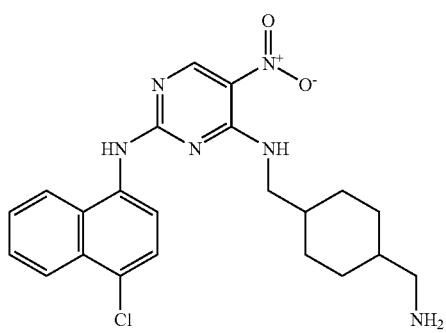

| | |
|---|---|
| -continued | |
| $N^4$-{[4-(aminomethyl)cyclohexyl]methyl}-$N^2$-(4-methoxy-2-naphthyl)-5-nitropyrimidine-2,4-diamine | m/z 437.3 (M + H)$^+$ |

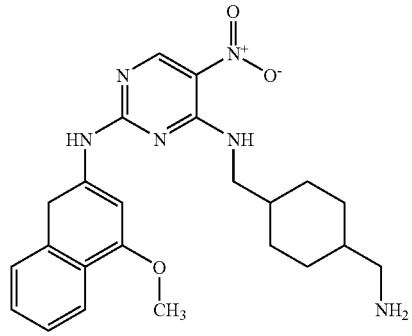

| | |
|---|---|
| $N^4$-{[4-(aminomethyl)cyclohexyl]methyl}-5-nitro-$N^2$-quinolin-6-ylpyrimidine-2,4-diamine | m/z 408.3 (M + H)$^+$ |

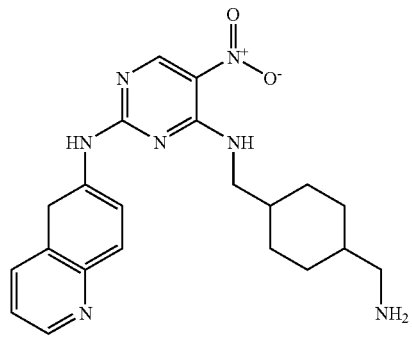

| | |
|---|---|
| $N^4$-{[4-trans-(aminomethyl)cyclohexyl]methyl}-$N^2$-(2,5-dichlorobenzyl)-5-nitropyrimidine-2,4-diamine | m/z 439.3 (M + H)$^+$ |

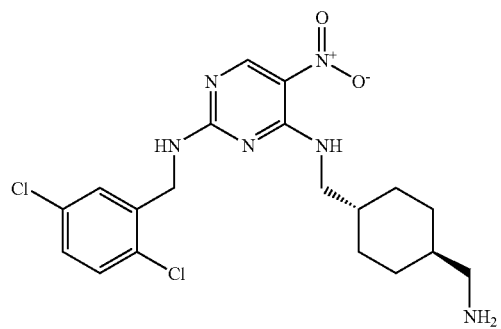

| | |
|---|---|
| $N^4$-{[4-trans-(aminomethyl)cyclohexyl]methyl}-$N^2$-(2,3-dichlorobenzyl)-5-nitropyrimidine-2,4-diamine | m/z 439.3 (M + H)$^+$ |

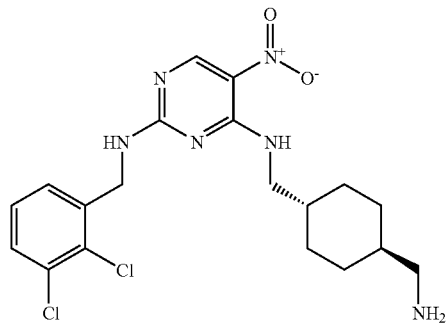

| | |
|---|---|
| $N^4$-{[4-(aminomethyl)cyclohexyl]methyl}-$N^2$-[2-(2-chlorophenyl)ethyl]-5-nitropyrimidine-2,4-diamine | m/z 419.4 (M +H) |
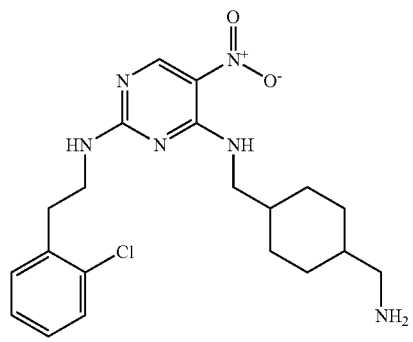
| | |
|---|---|
| $N^4$-{[4-(aminomethyl)cyclohexyl]methyl}-$N^2$-[2-(3-chlorophenyl)ethyl]-5-nitropyrimidine-2,4-diamine | m/z 419.4 (M + H)$^+$ |
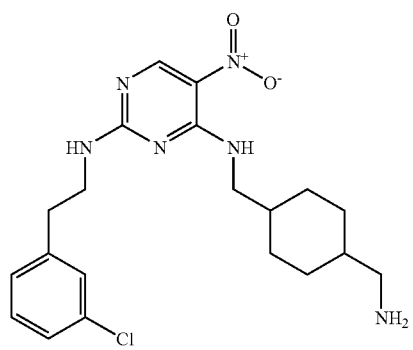
| | |
|---|---|
| $N^4$-{[4-(aminomethyl)cyclohexyl]methyl}-$N^2$-(2-chloro-6-phenoxybenzyl)-5-nitropyrimidine-2,4-diamine | m/z 497.4 (M + H)$^+$ |
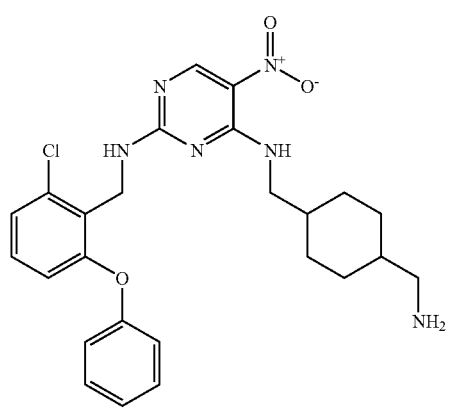

| | |
|---|---|
| $N^4$-{[4-(aminomethyl)cyclohexyl]methyl}-5-bromo-$N^2$-2-naphthylpyrimidine-2,4-diamine | m/z 441.10 (M + H)$^+$ |

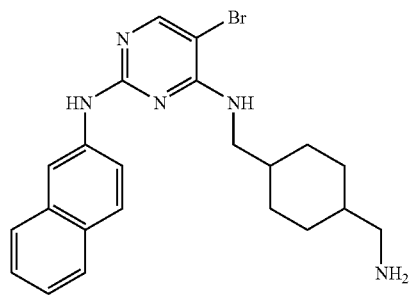

| | |
|---|---|
| $N^4$-{[4-(aminomethyl)cyclohexyl]methyl}-5-bromo-$N^2$-(1-naphthylmethyl)pyrimidine-2,4-diamine | m/z 455.20 (M + H)$^+$ |

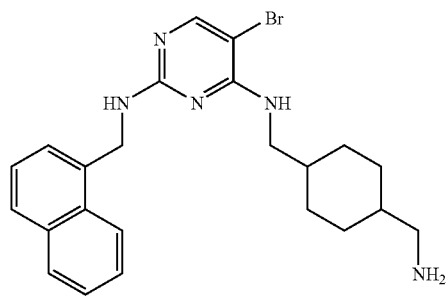

| | |
|---|---|
| $N^4$-{[4-(aminomethyl)cyclohexyl]methyl}-5-nitro-$N^2$-(pyridin-3-ylmethyl)pyrimidine-2,4-diamine | m/z 372.3 (M + H)$^+$ |

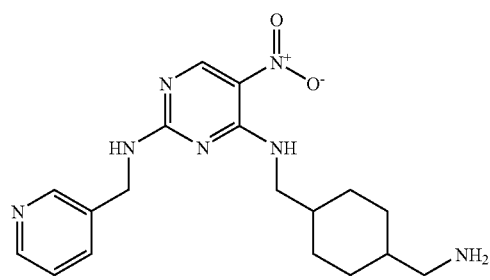

| | |
|---|---|
| 4-({[4-(aminomethyl)cyclohexyl]methyl}amino)-2-[(2-chlorobenzyl)amino]pyrimidine-5-carbonitrile | m/z 385.40 (M + H)$^+$ |

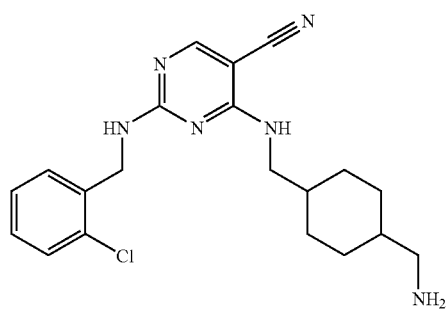

N⁴-{[4-(aminomethyl)cyclohexyl]methyl}-N²-[4-(dimethylamino)benzyl]-5-nitropyrimidine-2,4-diamine    m/z 414.4 (M + H)⁺
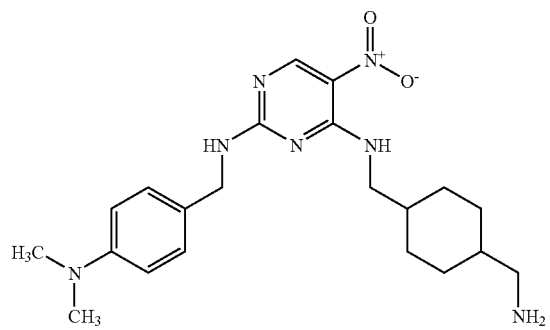
N⁴-{[4-trans-(aminomethyl)cyclohexyl]methyl}-N²-(2-bromobenzyl)-5-nitropyrimidine-2,4-diamine    m/z 451.2 (M + H)⁺
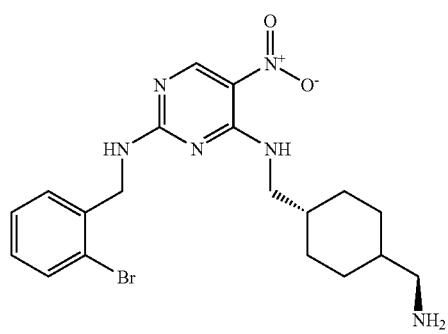
N⁴-(7-aminoheptyl)-N²-(2-bromobenzyl)-5-nitropyrimidine-2,4-diamine    m/z 437.3 (M + H)⁺
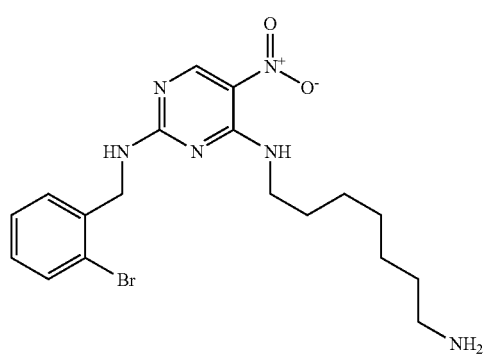
N⁴-(7-aminoheptyl)-N²-(2,5-dichlorobenzyl)-5-nitropyrimidine-2,4-diamine    m/z 427.3 (M + H)⁺
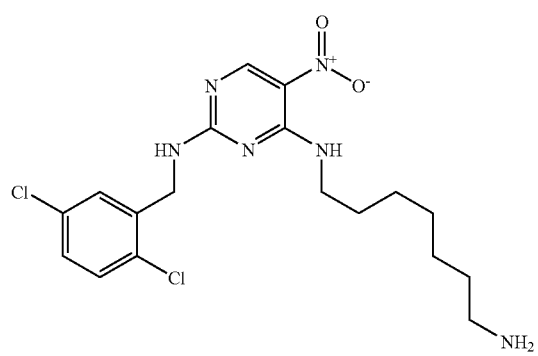

| | |
|---|---|
| N-({4-[({2-[(2-chlorobenzyl)amino]-5-nitropyrimidin-4-yl}amino)methyl]cyclohexyl}methyl)guanidine | m/z 446.9 (M + H)+ |
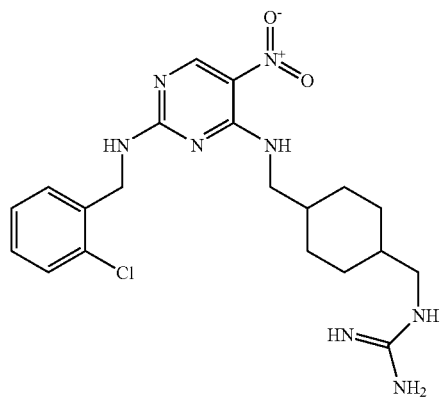
| | |
|---|---|
| N²-(3-aminobenzyl)-N⁴-{[4-(aminomethyl)cyclohexyl]methyl}-5-nitropyrimidine-2,4-diamine | m/z 386.4 (M+ H)+) |
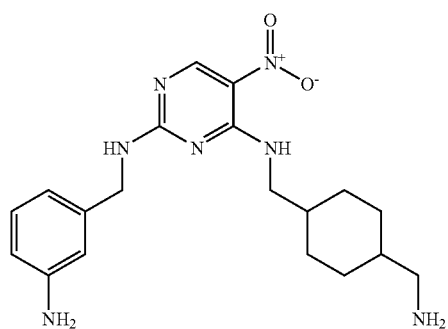
| | |
|---|---|
| N⁴-{[4-(aminomethyl)cyclohexyl]methyl}-5-nitro-N²-(2-nitrobenzyl)pyrimidine-2,4-diamine | m/z 416.5 (M + H)+ |
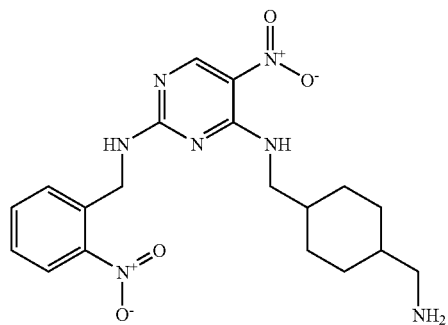

| | |
|---|---|
| N⁴-{[4-(aminomethyl)cyclohexyl]methyl}-N²-[2-(2-bromophenyl)ethyl]-5-nitropyrimidine-2,4-diamine | m/z 463.3 (M + H)⁺ |

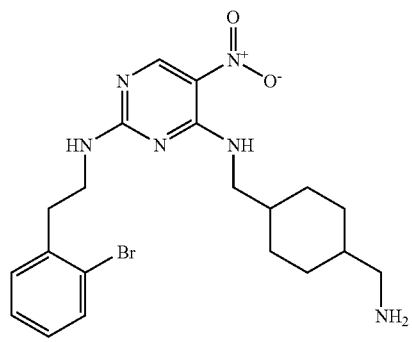

| | |
|---|---|
| N⁴-{[4-(aminomethyl)cyclohexyl]methyl}-N²-(2-bromobenzyl)-5-chloropyrimidine-2,4-diamine | m/z 439.0 (M + H)⁺ |

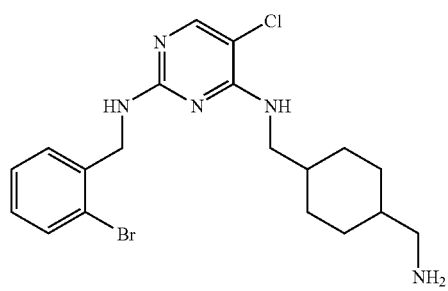

| | |
|---|---|
| (4-{[(2-{[2-(1H-indol-3-yl)ethyl]amino}-5-nitropyrimidin-4-yl)amino]methyl}cyclohexyl)methanaminium chloride | m/z 425.3 (M + H)⁺⁾ |

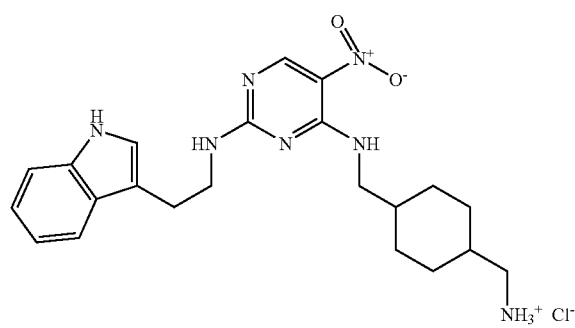

| | |
|---|---|
| N-({3-[({2-[(2-chlorobenzyl)amino]-5-nitropyrimidin-4-yl}amino)methyl]cyclohexyl}methyl)guanidine | m/z 447.4 (M + H)⁺ |

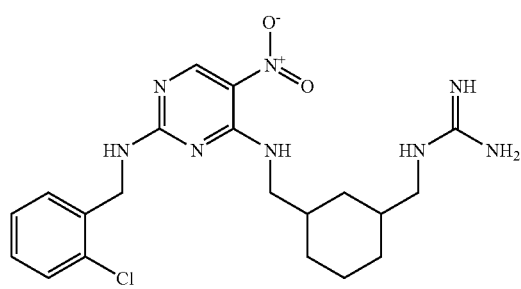

| | |
|---|---|
| 3-({[4-({[4-(aminomethyl)cyclohexyl]methyl}amino)-5-nitropyrimidin-2-yl]amino}methyl)phenol | m/z 387.4 (M + H)+ |

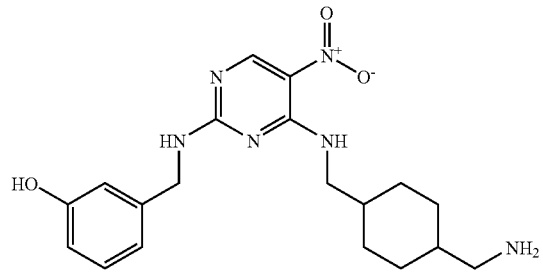

| | |
|---|---|
| (4-{[(2-{[2-(1H-imidazol-4-yl)ethyl]amino}-5-nitropyrimidin-4-yl)amino]methyl}cyclohexyl)methanaminium chloride | m/z 375 (M + H)+ |

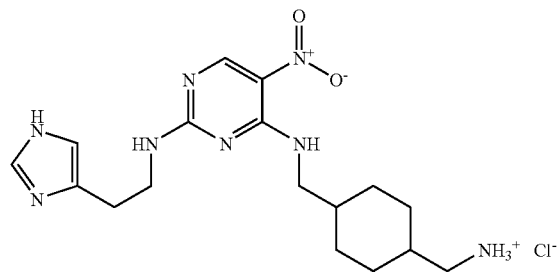

| | |
|---|---|
| $N^2$-(2-chlorobenzyl)-$N^4$-({4-cis-[(dimethylamino)methyl]cyclohexyl}methyl)-5-nitropyrimidine-2,4-diamine | m/z 433.2 (M + H)+ |

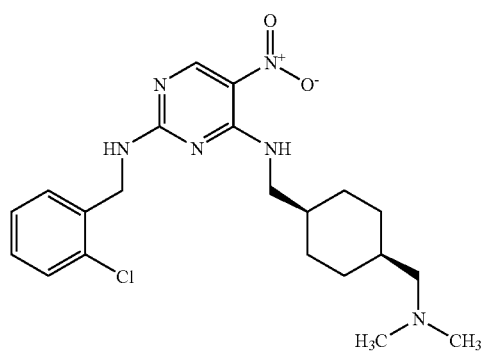

| | |
|---|---|
| $N^4$-{[4-(aminomethyl)cyclohexyl]methyl}-5-chloro-$N^2$-(2-chlorobenzyl)pyrimidine-2,4-diamine | m/z 395.10 (M + H)+ |

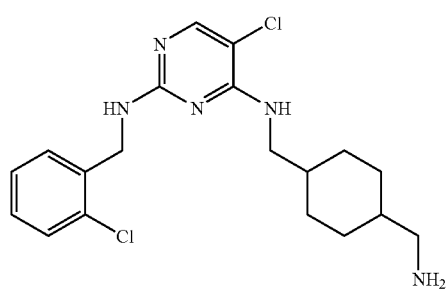

N²-(2-chlorobenzyl)-5-nitro-N⁴-(piperidin-4-ylmethyl)pyrimidine-2,4-diamine
m/z 377.5 (M + H)⁺
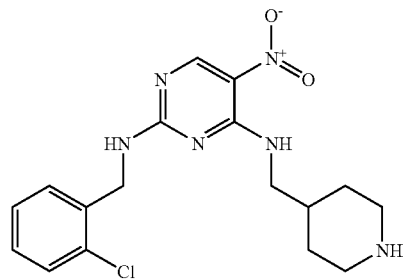
N⁴-{[4-(aminomethyl)cyclohexyl]methyl}-5-nitro-N²-(2-phenylethyl)pyrimidine-2,4-diamine
m/z 385.5 (M + H)⁺
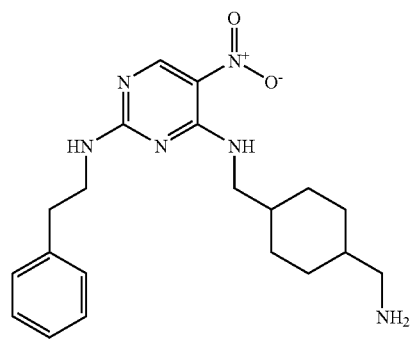
N⁴-{[4-(aminomethyl)cyclohexyl]methyl}-5-nitro-N²-(3-phenylpropyl)pyrimidine-2,4-diamine
m/z 399.4 (M + H)⁺
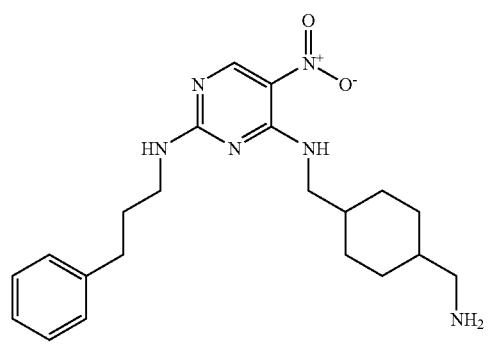

| | |
|---|---|
| $N^4$-{[4-(aminomethyl)cyclohexyl]methyl}-5-nitro-$N^2$-(4-phenylbutyl)pyrimidine-2,4-diamine | m/z 413.5 (M + H)⁺ |
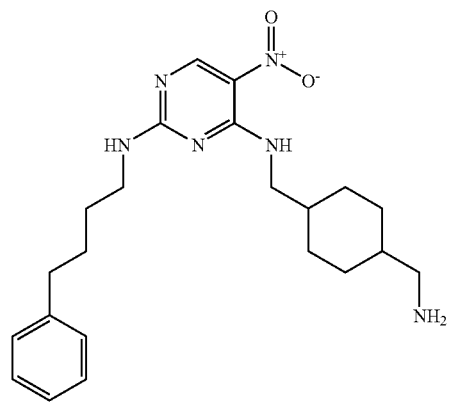
| | |
|---|---|
| $N^4$-{[4-(aminomethyl)cyclohexyl]methyl}-5-nitro-$N^2$-(2-phenylpropyl)pyrimidine-2,4-diamine | m/z 399.5 (M ' H)⁺ |
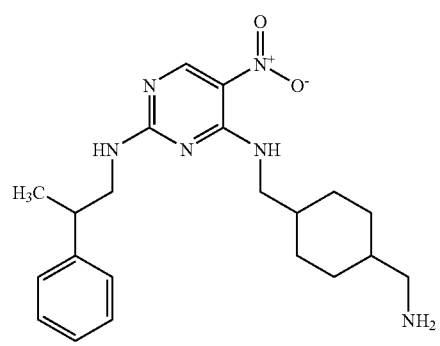
| | |
|---|---|
| $N^4$-{[4-(aminomethyl)cyclohexyl]methyl}-$N^2$-[2-(4-methoxyphenyl)ethyl]-5-nitropyrimidine-2,4-diamine | m/z 415.5 (M + H)⁺ |
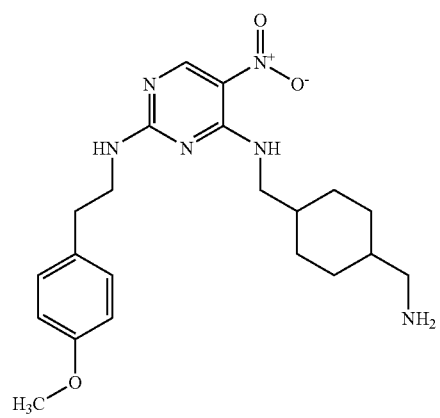

| | |
|---|---|
| $N^4$-{[4-(aminomethyl)cyclohexyl]methyl}-$N^2$-[2-(3-methoxyphenyl)ethyl]-5-nitropyrimidine-2,4-diamine | m/z 415.5 (M + H)$^+$ |
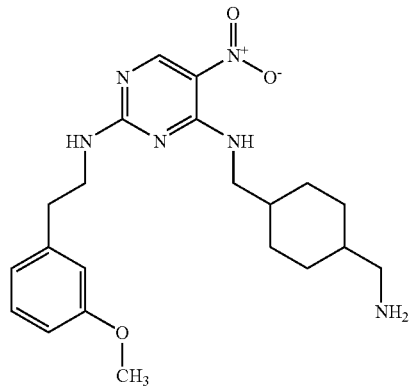
| | |
|---|---|
| $N^4$-{[4-(aminomethyl)cyclohexyl]methyl}-$N^2$-[2-(2-methoxyphenyl)ethyl]-5-nitropyrimidine-2,4-diamine | m/z 415.5 (M + H)$^+$ |
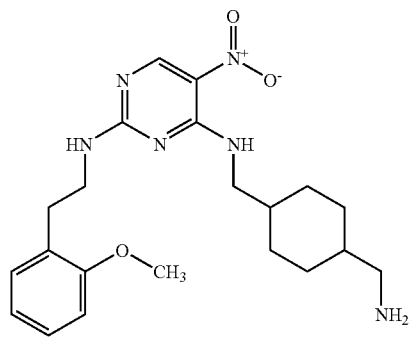
| | |
|---|---|
| 4-[({2-[(2-chlorobenzyl)amino]-5-nitropyrimidin-4-yl}amino)methyl]piperidine-1-carboximidamide | m/z 419.1 (M + H)$^+$ |
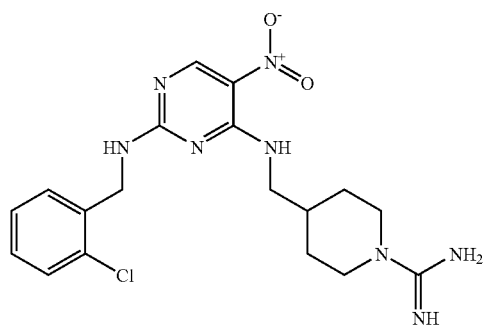

N4-{[4-(aminomethyl)cyclohexyl]methyl}-N2-(3,5-dichlorobenzyl)-5-nitropyrimidine-2,4-diamine
m/z 439.1 (M + H)+
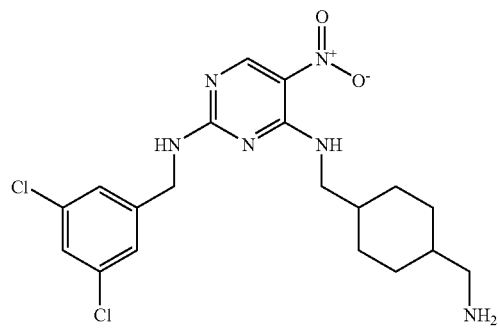
N4-(5-aminopentyl)-N2-(2-chlorobenzyl)-5-nitropyrimidine-2,4-diamine
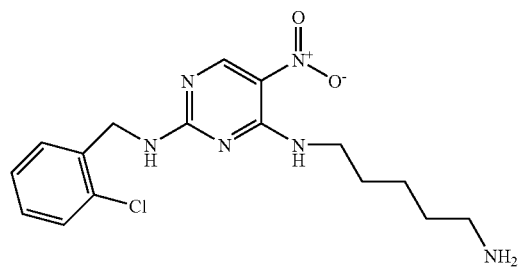
2-(benzylamino)-4-(1,4,6,7-tetrahydro-imidazo[4,5-c]pyridin-5-yl)-5-trifluoromethyl-pyrimidine
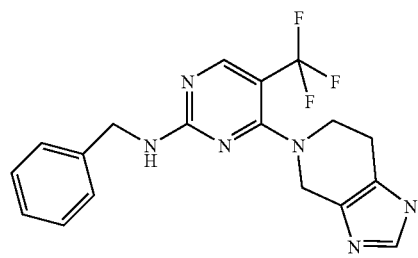
2-(4-chlorobenzylamino)-4-(1,4,6,7-tetrahydro-imidazo[4,5-c]pyridin-5-yl)-5-nitro-pyrimidine
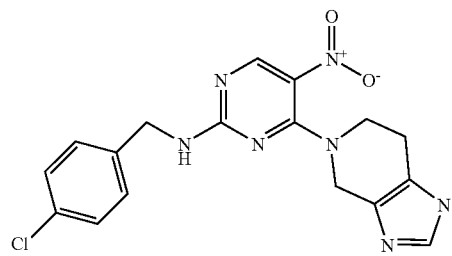

2-(2-chlorobenzylamino)-4-(1,4,6,7-tetrahydro-
imidazo[4,5-c]pyridin-5-yl)-5-nitro-pyrimidine

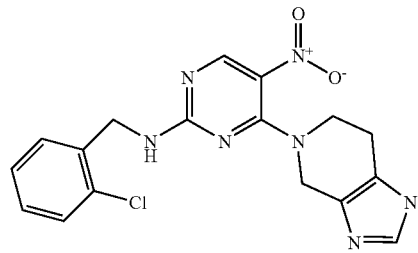

2-(benzylamino)-4-(1,4,6,7-tetrahydro-imidazo[4,5-
c]pyridin-5-yl)-5-nitro-pyrimidine

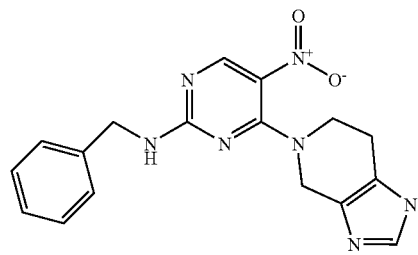

$N^4$-{[trans-4-(aminomethyl)cyclohexyl]methyl}-5-nitro-
$N^2$-[2-(trifluoromethoxy)benzyl]pyrimidine-2,4-diamine m/z 455.5 (M + H)$^+$

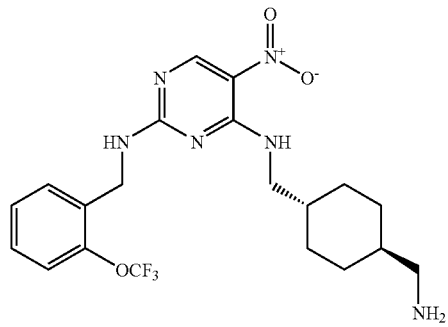

In another embodiment, there are provided compounds
selected from the group below:

$N^4$-{[4-(aminomethyl)cyclohexyl]methyl}-5-nitro-$N^2$-[(2R)-1,2,3,4-
tetrahydronaphthalen-2-yl]pyrimidine-2,4-diamine
$N^4$-{[4-(aminomethyl)cyclohexyl]methyl}-$N^2$-[2-(4-chlorophenyl)ethyl]-5-
nitropyrimidine-2,4-diamine
$N^4$-{[4-(aminomethyl)cyclohexyl]methyl}-$N^2$-[2-(3-methylphenyl)ethyl]-5-
nitropyrimidine-2,4-diamine
$N^4$-{[4-(aminomethyl)cyclohexyl]methyl}-$N^2$-[2-(4-methylphenyl)ethyl]-5-
nitropyrimidine-2,4-diamine
$N^4$-{[4-(aminomethyl)cyclohexyl]methyl}-$N^2$-[2-(3-fluorophenyl)ethyl]-5-
nitropyrimidine-2,4-diamine
$N^4$-{[4-(aminomethyl)cyclohexyl]methyl}-$N^2$-[2-(4-fluorophenyl)ethyl]-5-
nitropyrimidine-2,4-diamine
(1R,3R)-3-({[4-({[4-(aminomethyl)cyclohexyl]methyl}amino)-5-nitropyrimidin-2-
yl]amino}methyl)-4,4-dimethylcyclohexanol
$N^4$-({4-cis-[(dimethylamino)methyl]cyclohexyl}methyl)-$N^2$-(1-naphthylmethyl)-5-
nitropyrimidine-2,4-diamine -continued $N^2$-[2-(methylthio)benzyl]-5-nitro-$N^4$-(piperidin-4-ylmethyl)pyrimidine-2,4-diamine
5-nitro-$N^4$-(piperidin-4-ylmethyl)-$N^2$-{2-[(trifluoromethyl)thio] benzyl} pyrimidine-2,4-diamine
$N^2$-(1-naphthylmethyl)-5-nitro-$N^4$-(piperidin-4-ylmethyl)pyrimidine-2,4-diamine
$N^4$-({4-[(dimethylamino)methyl]cyclohexyl}methyl)-$N^2$-[2-(methylthio)benzyl]-5-nitropyrimidine-2,4-diamine
$N^4$-({4-[(dimethylamino)methyl]cyclohexyl}methyl)-5-nitro-$N^2$-{2-[(trifluoromethyl)thio]benzyl}pyrimidine-2,4-diamine
$N^4$-({4-[(dimethylamino)methyl]cyclohexyl}methyl)-$N^2$-(1-naphthylmethyl)-5-nitropyrimidine-2,4-diamine
$N^4$-{4-[(dimethylamino)methyl]benzyl}-$N^2$-[2-(methylthio)benzyl]-5-nitropyrimidine-2,4-diamine
$N^4$-{4-[(dimethylamino)methyl]benzyl}-5-nitro-$N^2$-{2-[(trifluoromethyl)thio]benzyl}pyrimidine-2,4-diamine
$N^4$-[(1-methylpiperidin-4-yl)methyl]-$N^2$-[2-(methylthio)benzyl]-5-nitropyrimidine-2,4-diamine
$N^4$-[(1-methylpiperidin-4-yl)methyl]-5-nitro-$N^2$-{2-[(trifluoromethyl)thio] benzyl}pyrimidine-2,4-diamine
$N^4$-{[4-(aminomethyl)cyclohexyl]methyl}-$N^2$-(2-methoxybenzyl)-5-nitropyrimidine-2,4-diamine
$N^4$-{[4-(aminomethyl)cyclohexyl]methyl}-5-nitro-$N^2$-[2-(trifluoromethyl)benzyl]pyrimidine-2,4-diamine
$N^4$-{[4-(aminomethyl)cyclohexyl]methyl}-$N^2$-(2,4-dichlorobenzyl)-5-nitropyrimidine-2,4-diamine
$N^4$-{[4-(aminomethyl)cyclohexyl]methyl}-$N^2$-[4-fluoro-2-(trifluoromethyl) benzyl]-5-nitropyrimidine-2,4-diamine
$N^4$-{[4-(aminomethyl)cyclohexyl]methyl}-$N^2$-(3-methylbenzyl)-5-nitropyrimidine-2,4-diamine
$N^4$-{[4-(aminomethyl)cyclohexyl]methyl}-$N^2$-(3-chlorobenzyl)-5-nitropyrimidine-2,4-diamine
$N^4$-{[4-(aminomethyl)cyclohexyl]methyl}-$N^2$-(4-bromobenzyl)-5-nitropyrimidine-2,4-diamine
$N^4$-{[4-(aminomethyl)cyclohexyl]methyl}-$N^2$-[2-chloro-5-(trifluoromethyl) benzyl]-5-nitropyrimidine-2,4-diamine
$N^4$-{[4-(aminomethyl)cyclohexyl]methyl}-$N^2$-(2,5-dichlorobenzyl)-5-nitropyrimidine-2,4-diamine
$N^4$-{[4-(aminomethyl)cyclohexyl]methyl}-5-nitro-$N^2$-[2-(trifluoromethoxy)benzyl]pyrimidine-2,4-diamine
$N^4$-{[4-(aminomethyl)cyclohexyl]methyl}-$N^2$-(2-chloro-6-methylbenzyl)-5-nitropyrimidine-2,4-diamine
$N^4$-{[4-(aminomethyl)cyclohexyl]methyl}-$N^2$-(2,3-dichlorobenzyl)-5-nitropyrimidine-2,4-diamine
$N^4$-{[3-(aminomethyl)cyclohexyl]methyl}-$N^2$-(2-chlorobenzyl)-5-nitropyrimidine-2,4-diamine
$N^2$-(2-chlorobenzyl)-$N^4$-({4-[(dimethylamino)methyl]cyclohexyl}methyl)-5-nitropyrimidine-2,4-diamine
$N^4$-{[4-(aminomethyl)cyclohexyl]methyl}-$N^2$-(2,5-difluorobenzyl)-5-nitropyrimidine-2,4-diamine
$N^4$-{[4-(aminomethyl)cyclohexyl]methyl}-$N^2$-(2-ethoxybenzyl)-5-nitropyrimidine-2,4-diamine
$N^4$-{[4-(aminomethyl)cyclohexyl]methyl}-$N^2$-(2-methylbenzyl)-5-nitropyrimidine-2,4-diamine
$N^4$-{[4-(aminomethyl)cyclohexyl]methyl}-$N^2$-(2-fluorobenzyl)-5-nitropyrimidine-2,4-diamine
$N^4$-{[4-(aminomethyl)cyclohexyl]methyl}-$N^2$-(3-chloro-2-fluorobenzyl)-5-nitropyrimidine-2,4-diamine
$N^4$-{[4-(aminomethyl)cyclohexyl]methyl}-$N^2$-(1,1'-biphenyl-2-ylmethyl)-5-nitropyrimidine-2,4-diamine
$N^4$-{[4-(aminomethyl)cyclohexyl]methyl}-$N^2$-(2,4-difluorobenzyl)-5-nitropyrimidine-2,4-diamine
$N^4$-{[4-(aminomethyl)cyclohexyl]methyl}-$N^2$-(2,3-difluorobenzyl)-5-nitropyrimidine-2,4-diamine
$N^4$-{[4-(aminomethyl)cyclohexyl]methyl}-$N^2$-(2,6-difluorobenzyl)-5-nitropyrimidine-2,4-diamine
$N^4$-{[4-(aminomethyl)cyclohexyl]methyl}-$N^2$-[2-fluoro-3-(trifluoromethyl) benzyl]-5-nitropyrimidine-2,4-diamine
$N^4$-{[4-(aminomethyl)cyclohexyl]methyl}-$N^2$-(4-chloro-2-fluorobenzyl)-5-nitropyrimidine-2,4-diamine
$N^4$-{[4-(aminomethyl)cyclohexyl]methyl}-$N^2$-(2-bromobenzyl)-5-nitropyrimidine-2,4-diamine
$N^4$-{[4-(aminomethyl)cyclohexyl]methyl}-$N^2$-(2,3-dimethylbenzyl)-5-nitropyrimidine-2,4-diamine
$N^4$-{[4-(aminomethyl)cyclohexyl]methyl}-$N^2$-[2-(methylthio)benzyl]-5-nitropyrimidine-2,4-diamine
$N^4$-{[4-(aminomethyl)cyclohexyl]methyl}-5-nitro-$N^2$-{2-[(trifluoromethyl)thio]benzyl}pyrimidine-2,4-diamine
$N^4$-{[4-(aminomethyl)cyclohexyl]methyl}-$N^2$-(3-fluorobenzyl)-5-nitropyrimidine-2,4-diamine -continued $N^4$-{[4-(aminomethyl)cyclohexyl]methyl}-$N^2$-(6-chloro-2-fluoro-3-methylbenzyl)-5-nitropyrimidine-2,4-diamine
$N^4$-{[4-(aminomethyl)cyclohexyl]methyl}-$N^2$-(2-chloro-6-fluoro-3-methylbenzyl)-5-nitropyrimidine-2,4-diamine
$N^4$-{[4-(aminomethyl)cyclohexyl]methyl}-$N^2$-2-naphthyl-5-nitropyrimidine-2,4-diamine
$N^4$-{[4-(aminomethyl)cyclohexyl]methyl}-$N^2$-(1-naphthylmethyl)-5-nitropyrimidine-2,4-diamine
$N^4$-{[4-(aminomethyl)cyclohexyl]methyl}-$N^2$-(4-chloro-2-methylbenzyl)-5-nitropyrimidine-2,4-diamine
$N^4$-{[4-(aminomethyl)cyclohexyl]methyl}-$N^2$-(5-chloro-2-methylbenzyl)-5-nitropyrimidine-2,4-diamine
$N^4$-{[4-(aminomethyl)cyclohexyl]methyl}-$N^2$-(3-chloro-2-methylbenzyl)-5-nitropyrimidine-2,4-diamine
$N^4$-{[4-(aminomethyl)cyclohexyl]methyl}-$N^2$-[5-fluoro-2-(trifluoromethyl)benzyl]-5-nitropyrimidine-2,4-diamine
$N^4$-{[4-(aminomethyl)cyclohexyl]methyl}-$N^2$-(5-chloro-2-fluorobenzyl)-5-nitropyrimidine-2,4-diamine
$N^4$-{[4-(aminomethyl)cyclohexyl]methyl}-$N^2$-(2,3-difluoro-4-methylbenzyl)-5-nitropyrimidine-2,4-diamine
$N^4$-{[4-(aminomethyl)cyclohexyl]methyl}-$N^2$-(5-fluoro-2-methylbenzyl)-5-nitropyrimidine-2,4-diamine
$N^4$-{[4-(aminomethyl)cyclohexyl]methyl}-5-bromo-$N^2$-(2,5-dichlorobenzyl)pyrimidine-2,4-diamine
$N^4$-{[4-(aminomethyl)cyclohexyl]methyl}-5-bromo-$N^2$-(2-bromobenzyl) pyrimidine-2,4-diamine
$N^4$-{[4-(aminomethyl)cyclohexyl]methyl}-$N^2$-(cyclohexylmethyl)-5-nitropyrimidine-2,4-diamine
$N^4$-{[4-(aminomethyl)cyclohexyl]methyl}-5-bromo-$N^2$-[2-(trifluoromethyl)benzyl]pyrimidine-2,4-diamine
$N^4$-{[4-(aminomethyl)cyclohexyl]methyl}-$N^2$-[2-(difluoromethoxy)benzyl]-5-nitropyrimidine-2,4-diamine
$N^4$-{[4-(aminomethyl)cyclohexyl]methyl}-$N^2$-(2-chloro-4-fluorobenzyl)-5-nitropyrimidine-2,4-diamine
$N^4$-{[4-(aminomethyl)cyclohexyl]methyl}-$N^2$-(2-chloro-3,6-difluorobenzyl)-5-nitropyrimidine-2,4-diamine
$N^4$-{[4-(aminomethyl)cyclohexyl]methyl}-5-nitro-$N^2$-(2,3,5-trifluorobenzyl)pyrimidine-2,4-diamine
$N^4$-{[4-(aminomethyl)cyclohexyl]methyl}-$N^2$-2,3-dihydro-1H-inden-2-yl-5-nitropyrimidine-2,4-diamine
$N^4$-{[4-(aminomethyl)cyclohexyl]methyl}-$N^2$-(4-chloro-1-naphthyl)-5-nitropyrimidine-2,4-diamine
$N^4$-{[4-(aminomethyl)cyclohexyl]methyl}-$N^2$-(4-methoxy-2-naphthyl)-5-nitropyrimidine-2,4-diamine
$N^4$-{[4-(aminomethyl)cyclohexyl]methyl}-5-nitro-$N^2$-quinolin-6-ylpyrimidine-2,4-diamine
$N^4$-{[4-trans-(aminomethyl)cyclohexyl]methyl}-$N^2$-(2,3-dichlorobenzyl)-5-nitropyrimidine-2,4-diamine
$N^4$-{[4-(aminomethyl)cyclohexyl]methyl}-$N^2$-[2-(2-chlorophenyl)ethyl]-5-nitropyrimidine-2,4-diamine
$N^4$-{[4-(aminomethyl)cyclohexyl]methyl}-$N^2$-[2-(3-chlorophenyl)ethyl]-5-nitropyrimidine-2,4-diamine
$N^4$-{[4-(aminomethyl)cyclohexyl]methyl}-5-bromo-$N^2$-2-naphthylpyrimidine-2,4-diamine
4-({[4-(aminomethyl)cyclohexyl]methyl}amino)-2-[(2-chlorobenzyl)amino]pyrimidine-5-carbonitrile
$N^4$-{[4--trans-(aminomethyl)cyclohexyl]methyl}-$N^2$-(2-bromobenzyl)-5-nitropyrimidine-2,4-diamine
$N^4$-(7-aminoheptyl)-$N^2$-(2-bromobenzyl)-5-nitropyrimidine-2,4-diamine
$N^4$-(7-aminoheptyl)-$N^2$-(2,5-dichlorobenzyl)-5-nitropyrimidine-2,4-diamine
N-({4-[({2-[(2-chlorobenzyl)amino]-5-nitropyrimidin-4-yl}amino)methyl]cyclohexyl}methyl)guanidine
$N^4$-{[4-(aminomethyl)cyclohexyl]methyl}-5-nitro-$N^2$-(2-nitrobenzyl)pyrimidine-2,4-diamine
$N^4$-{[4-(aminomethyl)cyclohexyl]methyl}-$N^2$-[2-(2-bromophenyl)ethyl]-5-nitropyrimidine-2,4-diamine
$N^4$-{[4-(aminomethyl)cyclohexyl]methyl}-$N^2$-(2-bromobenzyl)-5-chloropyrimidine-2,4-diamine
N-({3-[({2-[(2-chlorobenzyl)amino]-5-nitropyrimidin-4-yl}amino)methyl]cyclohexyl}methyl)guanidine
3-({[4-({[4-(aminomethyl)cyclohexyl]methyl}amino)-5-nitropyrimidin-2-yl]amino}methyl)phenol
$N^2$-(2-chlorobenzyl)-$N^4$-({4-cis-[(dimethylamino)methyl]cyclohexyl}methyl)-5-nitropyrimidine-2,4-diamine
$N^2$-(2-chlorobenzyl)-5-nitro-$N^4$-(piperidin-4-ylmethyl)pyrimidine-2,4-diamine
$N^4$-{[4-(aminomethyl)cyclohexyl]methyl}-5-nitro-$N^2$-(2-phenylethyl)pyrimidine-2,4-diamine -continued N⁴-{[4-(aminomethyl)cyclohexyl]methyl}-5-nitro-N²-(4-phenylbutyl)pyrimidine-2,4-diamine
N⁴-{[trans-4-(aminomethyl)cyclohexyl]methyl}-5-nitro-N²-[2-(trifluoromethoxy)-benzyl]pyrimidine-2,4-diamine In yet another embodiment, there are provided compounds selected from the group below:

N⁴-({4-[(dimethylamino)methyl]cyclohexyl}methyl)-N²-(1-naphthylmethyl)-5-nitropyrimidine-2,4-diamine
N²-[2-(methylthio)benzyl]-5-nitro-N⁴-(piperidin-4-ylmethyl)pyrimidine-2,4-diamine
5-nitro-N⁴-(piperidin-4-ylmethyl)-N²-{2-[(trifluoromethyl)thio] benzyl}pyrimidine-2,4-diamine
N²-(1-naphthylmethyl)-5-nitro-N⁴-(piperidin-4-ylmethyl)pyrimidine-2,4-diamine
N⁴-({4-[(dimethylamino)methyl]cyclohexyl}methyl)-N²-[2-(methylthio)benzyl]-5-nitropyrimidine-2,4-diamine
N⁴-({4-[(dimethylamino)methyl]cyclohexyl}methyl)-5-nitro-N²-{2-[(trifluoromethyl)thio]benzyl}pyrimidine-2,4-diamine
N⁴-({4-[(dimethylamino)methyl]cyclohexyl}methyl)-N²-(1-naphthylmethyl)-5-nitropyrimidine-2,4-diamine
N⁴-{4-[(dimethylamino)methyl]benzyl}-N²-[2-(methylthio)benzyl]-5-nitropyrimidine-2,4-diamine
N⁴-{4-[(dimethylamino)methyl]benzyl}-5-nitro-N²-{2-[(trifluoromethyl)thio] benzyl}pyrimidine-2,4-diamine
N⁴-[(1-methylpiperidin-4-yl)methyl]-N²-[2-(methylthio)benzyl]-5-nitropyrimidine-2,4-diamine
N⁴-[(1-methylpiperidin-4-yl)methyl]-5-nitro-N²-{2-[(trifluoromethyl)thio] benzyl}pyrimidine-2,4-diamine
N⁴-{[4-(aminomethyl)cyclohexyl]methyl}-N²-(2-methoxybenzyl)-5-nitropyrimidine-2,4-diamine
N⁴-{[4-(aminomethyl)cyclohexyl]methyl}-5-nitro-N²-[2-(trifluoromethoxy) benzyl]pyrimidine-2,4-diamine
N⁴-{[4-(aminomethyl)cyclohexyl]methyl}-N²-(2,3-dichlorobenzyl)-5-nitropyrimidine-2,4-diamine
N⁴-{[3-(aminomethyl)cyclohexyl]methyl}-N²-(2-chlorobenzyl)-5-nitropyrimidine-2,4-diamine
N²-(2-chlorobenzyl)-N⁴-({4-[(dimethylamino)methyl]cyclohexyl}methyl)-5-nitropyrimidine-2,4-diamine
N⁴-{[4-(aminomethyl)cyclohexyl]methyl}-N²-(2-bromobenzyl)-5-nitropyrimidine-2,4-diamine
N⁴-{[4-(aminomethyl)cyclohexyl]methyl}-N²-[2-(methylthio)benzyl]-5-nitropyrimidine-2,4-diamine
N⁴-{[4-(aminomethyl)cyclohexyl]methyl}-5-nitro-N²-{2-[(trifluoromethyl)thio]benzyl}pyrimidine-2,4-diamine
N⁴-{[4-(aminomethyl)cyclohexyl]methyl}-N²-(1-naphthylmethyl)-5-nitropyrimidine-2,4-diamine
N⁴-{[4-(aminomethyl)cyclohexyl]methyl}-N²-(2,3-dichlorobenzyl)-5-nitropyrimidine-2,4-diamine
N⁴-{[4-(aminomethyl)cyclohexyl]methyl}-N²-(2-bromobenzyl)-5-nitropyrimidine-2,4-diamine
N²-(2-chlorobenzyl)-5-nitro-N⁴-(piperidin-4-ylmethyl)pyrimidine-2,4-diamine
N⁴-{[trans-4-(aminomethyl)cyclohexyl]methyl}-5-nitro-N²-[2-(trifluoromethoxy)-benzyl]pyrimidine-2,4-diamine As discussed above, any compound of this invention may occur as individual geometric isomers, stereoisomers, enantiomers, diastereomers, racemates, racemic or non-racemic mixtures of stereoisomers, and mixtures of diastereomers, All such isomeric forms, and mixtures thereof, of these compounds are expressly included in the present invention. Each stereogenic carbon may be in the R or S configuration, or a combination of configurations.

Some of the compounds of the present invention can exist in more than one tautomeric form. The invention also includes all such tautomers.

General Synthetic Methods

The compounds of the invention may be prepared by the methods described below. In each of the schemes below, the groups $R_1$, $R_2$ and $R_3$ are as defined above for general formula I unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. Intermediates and products may be purified by chromatography on silica gel and/or recrystallization. Starting materials and reagents are either commercially available or may be prepared by one skilled in the art using methods described in the chemical literature.

Compounds of formula (I) may be prepared as illustrated in Scheme I and described below.

Scheme I

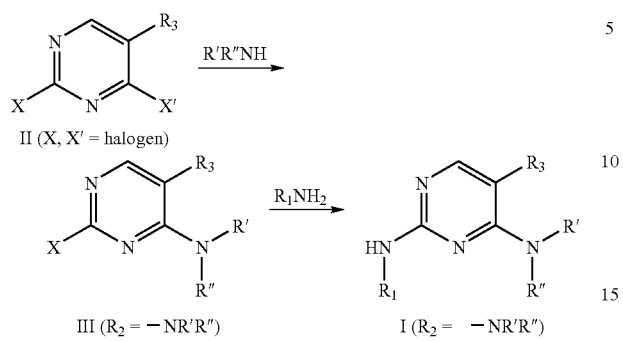

As illustrated above, a 2,4-dihalopyrimidine (II), preferably a 2,4-dichloropyrimidine, is reacted with about one equivalent of an amine (R'R"NH) in the presence of a base, such as triethylamine, in a suitable solvent, such as EtOH, to provide intermediate III. The reaction is carried out preferably at about 0° C. to about room temperature. Intermediate III is then reacted with a second amine $R_1NH_2$ in a suitable solvent, such as EtOH, to provide the desired I. The reaction is preferably heated to about the reflux temperature of the solvent. For intermediates III having $R_3$ groups that are less electron withdrawing than $NO_2$, such as $R_3$=F, Cl, CN or $CO_2Et$, the reaction is preferably carried out in a sealed vessel in a microwave reactor at about 140° C.

If $R_2$ contains a second amine group, (i.e., in the R' and/or R" groups in Scheme I above) the second amine is preferably protected with a suitable amino-protecting group, for example with a Boc-group, prior to reaction with intermediate II, and the amine is deprotected after reaction of the pyrimidine intermediate with $R_1NH_2$. For example, in the case of 1,4-cyclohexanebis(methylamine) as illustrated in Scheme II, the mono-Boc-protected diamine is reacted with II as described above. The resulting intermediate IV is then reacted with $R_1NH_2$ as described above, and the Boc-protected intermediate V is then deprotected by treatment with acid to provide the desired compound of formula (I).

Scheme II

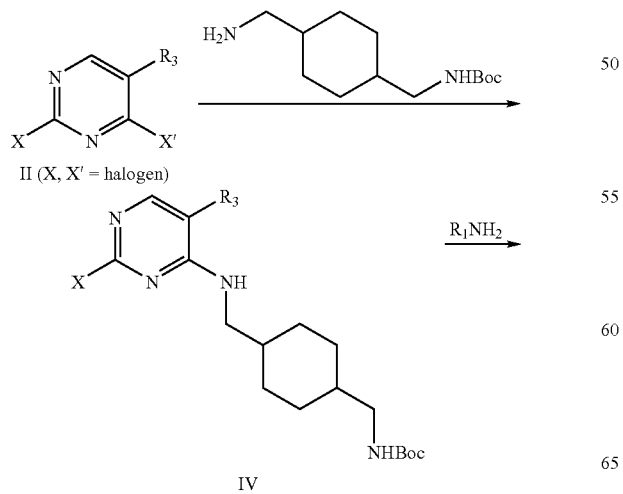

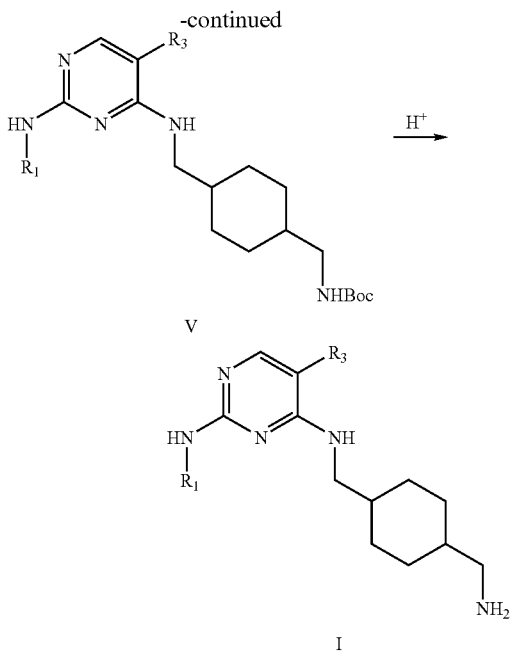

In a variation illustrated in Scheme III, if $R_3$ is $NO_2$, intermediate II may be reacted with a thiocyanate salt, such as potassium thiocyanate, in a suitable solvent, such as EtOH, to produce VI. Intermediate VI is reacted with $R_1NH_2$ in a suitable solvent, such as EtOH, and in the presence of a base, such as triethylamine, to provide VII. Intermediate VII may then be reacted with an amine R'R"NH in a suitable solvent, such as EtOH or methylene chloride, to provide the desired compound of formula I Scheme III

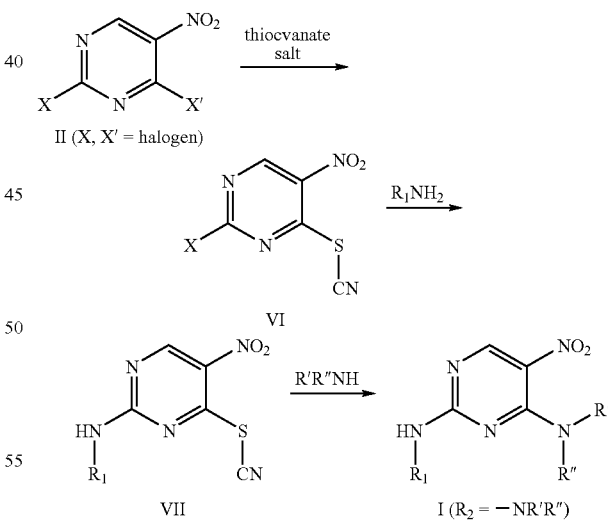

Substituents $R_1$, $R_2$ and $R_3$ may be further modified by methods known in the art to obtain additional compounds of formula (I). Some of these modifications are illustrated in the synthetic examples below.

In order that this invention be more fully understood, the following examples are set forth. These examples are for the purpose of illustrating embodiments of this invention, and are not to be construed as limiting the scope of the invention in any way. Starting materials used are either commercially available or easily prepared from commercially available materials by those skilled in the art.

SYNTHETIC EXAMPLES

Example 1

Synthesis of $N^4$-(4-aminomethyl-cyclohexylmethyl)-$N^2$-(2-chloro-benzyl)-5-fluoro-pyrimidine-2,4-diamine

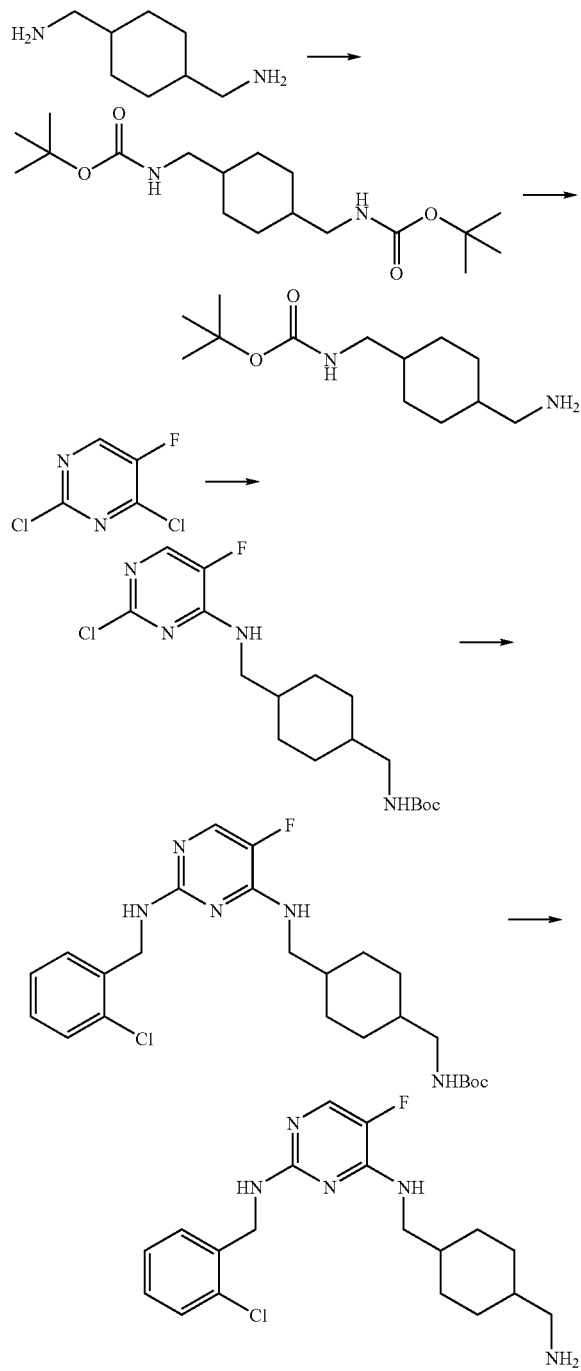

Di-tert-butyl dicarbonate (44.00 g, 201 mmol) was added to a solution of 1,4-cyclohexanebis(methylamine)cis+trans (14.35 g, 142 mmol) in $CH_2Cl_2$ at room temperature. After stirring at room temperature for 16 h, the reaction mixture was concentrated in vacuo to provide [4-(tert-butoxycarbonylamino-methyl)-cyclohexylmethyl]-carbamic acid tert-butyl ester as a white powder 34.32 g, 99%, m/z calculated for $C_{18}H_{34}N_2O_4$: 342.5, found: 343.3 $(M+H)^+$.

To a solution of [4-(tert-butoxycarbonylamino-methyl)-cyclohexylmethyl]-carbamic acid tert-butyl ester (11.00 g, 32 mmol) dissolved in 2:1 $CHCl_3$:EtOH at room temperature was added 4.0 M HCl/dioxane (16.1 mL). The mixture was stirred at room temperature for 4 h then concentrated in vacuo to provide a crude white solid. The crude material was purified by silica gel chromatography using a gradient elution of 10-50% (2% $NH_4OH$, 18% MeOH, 80% $CH_2Cl_2$)/$CH_2Cl_2$. The product-containing fractions were combined and concentrated in vacuo to provide (4-aminomethyl-cyclohexylmethyl)-carbamic acid tert-butyl ester as a white powder 3.62 g, 47%, m/z calculated for $C_{13}H_{26}N_2O_2$: 242.4, found: 243.3 $(M+H)^+$.

To a solution of (4-aminomethyl-cyclohexylmethyl)-carbamic acid tert-butyl ester (606 mg, 2.5 mmol) and triethylamine (0.7 mL, 5.0 mmol) dissolved in EtOH at 0° C., was added 2,4-dichloro-5-fluoropyrimidine (835 mg, 5.0 mmol). The reaction mixture was warmed to room temperature and stirred for 18 h. The mixture was then concentrated in vacuo and the crude product was purified by silica gel chromatography using 0-20% EtOAc/hexanes. The product-containing fractions were combined and concentrated in vacuo to provide {4-[(2-chloro-5-fluoro-pyrimidinyl-4-amino)-methyl]-cyclohexylmethyl}-carbamic acid tert-butyl ester as a white solid 495 mg, 53%, m/z calculated for $C_{17}H_{26}ClFN_4O_2$: 372.9, found: 373.4 $(M+H)^+$.

{4-[(2-chloro-5-fluoro-pyrimidinyl-4-amino)-methyl]-cyclohexylmethyl}-carbamic acid tert-butyl ester and 2-chlorobenzylamine were added to a microwave reaction tube and dissolved in absolute EtOH (2 mL). The reaction mixture was heated 140° C. in a microwave reactor for 5 h. and then cooled to room temperature. The reaction mixture was then concentrated in vacuo, dissolved in $CHCl_3$, and purified by silica gel chromatography using 10-20% EtOAc/hexanes. The product-containing fractions were combined and concentrated in vacuo to provide {4-[(2-(2-chlorobenzylamino)-5-fluoro-pyrimidinyl-4-amino)-methyl]-cyclohexylmethyl}-carbamic acid tert-butyl ester as a colorless foam 102 mg, 53%, m/z calculated for $C_{24}H_{33}ClFN_5O2$: 478.0, found: 479.8 $(M+H)^+$.

To a solution of {4-[(2-(2-chlorobenzylamino)-5-fluoro-pyrimidinyl-4-amino)-methyl]-cyclohexylmethyl}-carbamic acid tert-butyl ester (102 mg, 0.213 mmol) dissolved in 2:1 $CHCl_3$:EtOH at room temperature was added 4.0 M HCl/dioxane (5.0 mL). The mixture was stirred at room temperature for 2 h then concentrated in vacuo to provide a crude white powder. The crude material was purified by silica gel chromatography using a gradient elution of 10-50% (2% $NH_4OH$, 18% MeOH, 80% $CH_2Cl_2$)/$CH_2Cl_2$. The product-containing fractions were combined and concentrated in vacuo to provide the title compound as a colorless foam 76 mg, 94%, m/z calculated for $C_{19}H_{25}ClFN_5$: 377.9, found: 378.4 $(M+H)^+$.

Example 2

Synthesis of N⁴-(4-aminomethyl-cyclohexylmethyl)-5-chloro-N²-(2-chloro-benzyl)-pyrimidine-2,4-diamine

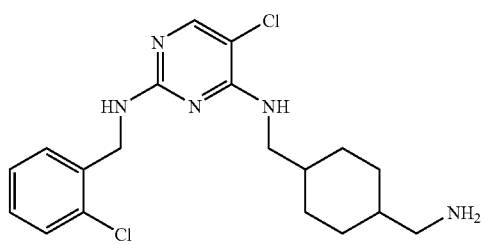

2

This compound was prepared from 2,4,5-trichloropyrimidine using the same procedures described in Example 1 to provide the title compound as a white solid 41 mg, 30%, m/z calculated for $C_{19}H_{25}Cl_2N_5$: 394.4, found: 395.3 (M+H)⁺.

Example 3

Synthesis of N⁴-(4-aminomethyl-cyclohexylmethyl)-5-bromo-N²-(2-chloro-benzyl)-pyrimidine-2,4-diamine

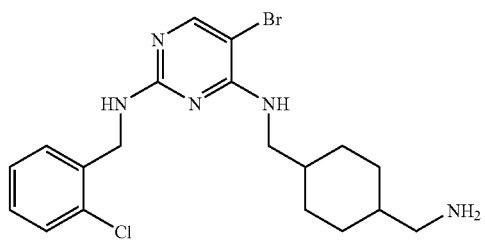

3

This compound was prepared from 5-bromo-2,4-dichloropyrimidine using the same procedures described in Example 1 to provide the title compound as a white solid 18 mg, 22%, m/z calculated for $C_{19}H_{25}BrClN_5$: 438.8, found: 439.9 (M+H)⁺.

Example 4

Synthesis of 4-[(4-aminomethyl-cyclohexylmethyl)-amino]-2-(2-chloro-benzylamino)-pyrimidine-5-carbonitrile

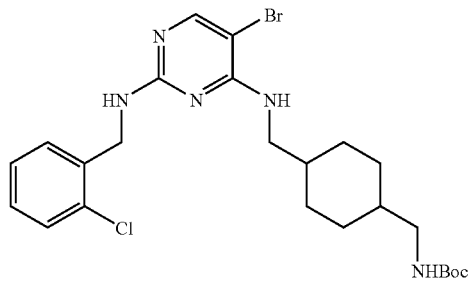

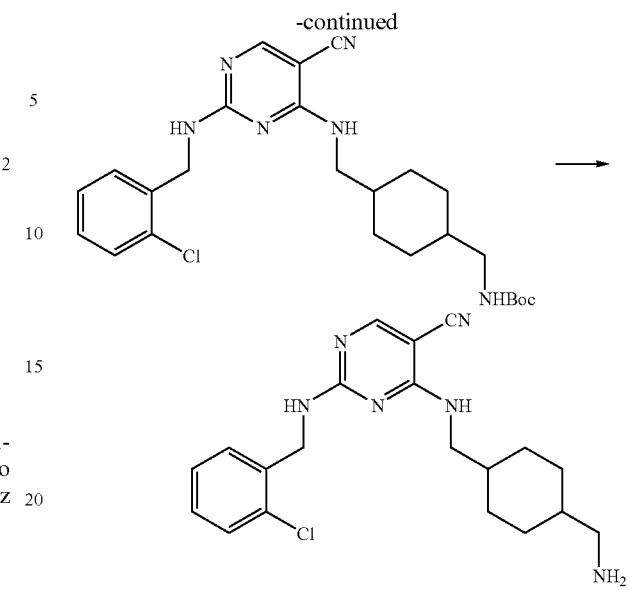

4

A mixture of tris(dibenzylidenacetone)-dipalladium(0) (26 mg, 0.028 mmol), zinc cyanide (20 mg, 169 mmol), 1,1'-bis(diphenylphosphino)-ferrocene (19 mg, 0.034 mmol) and {4-[(2-(2-chlorobenzylamino)-5-bromo-pyrimidinyl-4-amino)-methyl]-cyclohexylmethyl}-carbamic acid tert-butyl ester (155 mg, 0.288 mmol) in a pressure tube was evacuated and filled with $N_2$ several times. The mixture was then dissolved in degassed DMF (2 mL) and heated to 130° C. under an $N_2$ atmosphere for 18 h. The mixture was then concentrated in vacuo, dissolved in $CH_2Cl_2$, and filtered through a pad of diatomaceous earth. The filtrate was then concentrated in vacuo and purified by silica gel chromatography using 0-25% EtOAc/hexanes. The product-containing fractions were combined and concentrated in vacuo to provide the desired cyano intermediate as a pale yellow foam 65 mg, 47%, m/z calculated for $C_{25}H_{33}ClN_6O_2$: 485.034, found: 486.9 (M+H)⁺.

Compound 4 was prepared from the above cyano intermediate by treating with 4.0 M HCl/dioxane using the same deprotection procedure previously described for Example 1. The title compound was isolated as a pale yellow foam 27 mg, 59%, m/z calculated for $C_{20}H_{25}ClN_6$: 384.9, found: 385.4 (M+H)⁺.

Example 5

Synthesis of 4-[(4-aminomethyl-cyclohexylmethyl)-amino]-2-(2-chloro-benzylamino)-pyrimidine-5-carboxylic acid ethyl ester

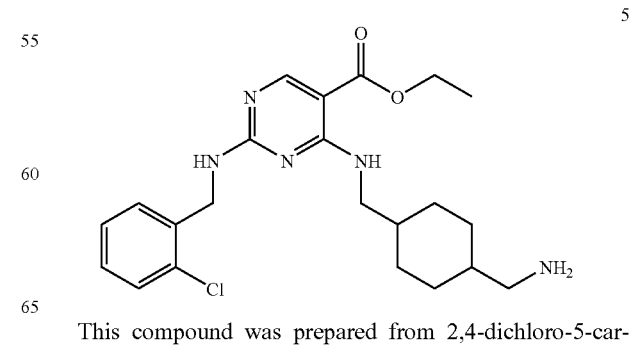

5

This compound was prepared from 2,4-dichloro-5-carboethoxypyrimidine using the same procedures described in Example 1. The title compound was isolated as a white powder, m/z calculated for $C_{22}H_{30}ClN_5O_2$: 431.9, found: 432.3 $(M+H)^+$.

Example 6

Synthesis of 4-[(4-aminomethyl-cyclohexylmethyl)-amino]-2-(2-chloro-benzylamino)-pyrimidine-5-carboxylic acid

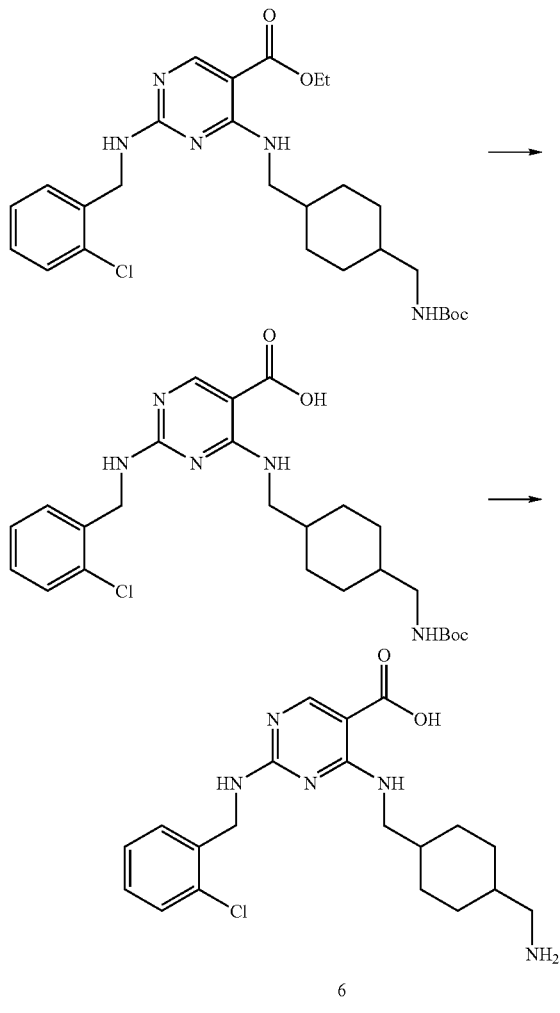

A solution of LiOH (240 mg, 10 mmol) in $H_2O$ (10 mL) was added to 4-{[(4-tert-butoxycarbonylamino-methyl)-cyclohexylmethyl]-amino}-2-(2-chloro-benzylamino)-pyrimidine-5-carboxylic acid ethyl ester dissolved in EtOH (15 mL) at room temperature. The mixture was heated to 80° C. for 6 h and then concentrated in vacuo until a crude white precipitate formed. The crude product was filtered, washed with EtOAc, and dried in vacuo to provide a white powder 563 mg, 99%, m/z calculated for $C_{25}H_{34}ClN_5O_4$: 504.0, found: 505.8 $(M+H)^+$.

To a solution of 4-{[4-(tert-butoxycarbonylamino-methyl)-cyclohexylmethyl]-amino}-2-(2-chloro-benzylamino)-pyrimidine-5-carboxylic acid (80 mg, 0.159 mmol) dissolved in 2:1 $CHCl_3$:EtOH at room temperature was added 4.0 M HCl/dioxane (5.0 mL). The mixture was stirred at room temperature for 2 h then concentrated in vacuo to provide a crude white powder. The crude material was purified by preparative scale reverse phase HPLC using a 0.1% TFA-$H_2O$/$CH_3CN$ mobile phase. The product-containing fractions were combined and concentrated in vacuo to provide 34 mg of the title compound as a white solid, 53%, m/z calculated for $C_{20}H_{26}ClN_5O_2$: 403.9, found: 404.4 $(M+H)^+$.

Example 7

Synthesis of 4-[(4-aminomethyl-cyclohexylmethyl)-amino]-2-(2-chloro-benzylamino)-pyrimidine-5-carboxylic acid methyl ester

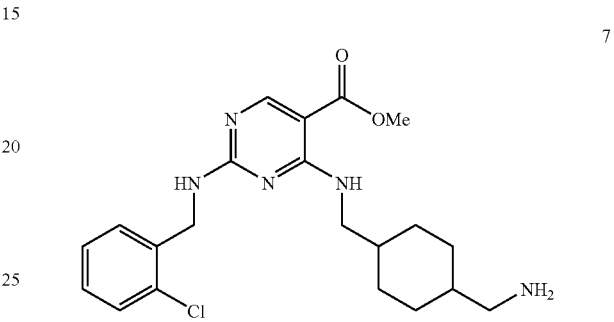

To a solution of 4-{[4-(tert-butoxycarbonylamino-methyl)-cyclohexylmethyl]-amino}-2-(2-chloro-benzylamino)-pyrimidine-5-carboxylic acid (120 mg, 0.238 mmol) in 1:1 MeOH:$CH_2Cl_2$ (5 mL) was added 2.0 M (trimethylsilyl)diazomethane in hexanes. The mixture was stirred at room temperature for 18 h and then concentrated in vacuo to provide a pale yellow solid which was purified by silica gel chromatography using 0-60% EtOAc/hexanes. The product-containing fractions were combined and concentrated in vacuo to provide a white solid 80 mg, 65%, m/z calculated for $C_{26}H_{36}ClN_5O_4$: 518.0, found: 519.7 $(M+H)^+$.

Treatment of the above tert-butoxycarbonyl protected amine with 4.0 M HCl/dioxane as described for Example 1 provided the title compound as a white powder 20 mg, 31%, m/z calculated for $C_{21}H_{28}ClN_5O_2$: 417.9, found: 418.4 $(M+H)^+$.

Example 8

Synthesis of 4-[(4-aminomethyl-cyclohexylmethyl)-amino]-2-(2-chloro-benzylamino)-pyrimidine-5-carboxylic acid amide

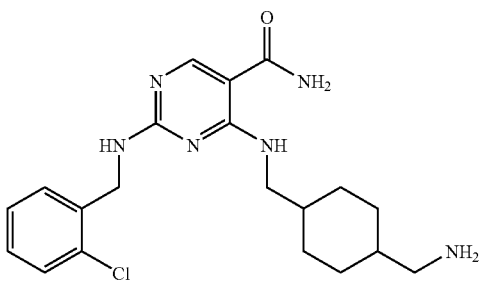

DMF (7 mL) was added to 4-{[4-(tert-butoxycarbonylamino-methyl)-cyclohexylmethyl]-amino}-2-(2-chloro-benzylamino)-pyrimidine-5-carboxylic acid (120 mg, 0.238 mmol) (see Example 6), 1-[3-(dimethylamino)propyl]-3-ethylcarbodiimide (50 mg, 0.262 mmol), and 1-hydroxybenzotriazole (35 mg, 0.262 mmol) at 0° C. After stirring for 0.5 h, ammonium hydroxide (0.170 mL, 1.190 mL) was added and the mixture was warmed to room temperature and stirred for 18 h. The mixture was then concentrated in vacuo and the residue dissolved in EtOAc (30 mL), and washed with 1 N HCl (3×50 mL) followed by saturated NaHCO$_3$ (3×50 mL). The product solution was dried over Na$_2$SO$_4$ and concentrated in vacuo to provide a white solid. The crude product was dissolved in 1:1 MeOH:CH$_2$Cl$_2$ and purified by preparative TLC using a 2% NH$_4$OH, 18% MeOH, 80% CH$_2$Cl$_2$ mobile phase. The product-containing band was removed from the plate and washed with the mobile phase solution. The mixture was filtered and the filtrate concentrated in vacuo to provide a white solid 65 mg, 54%, m/z calculated for C$_{25}$H$_{35}$ClN$_6$O$_3$: 503.0, found: 504.8 (M+H)$^+$.

Treatment of the above tert-butoxycarbonyl protected amine with 4.0 M HCl/dioxane as described for Example 1 provided the title compound as a white solid 31 mg, 60%, m/z calculated for C$_{20}$H$_{27}$ClN$_6$O: 402.9, found: 403.4 (M+H)$^+$.

Example 9

Synthesis of N-(4-{[2-(2-chloro-benzylamino)-5-nitro-pyrimidin-4-ylamino]-methyl}-cyclohexylmethyl)-guanidine

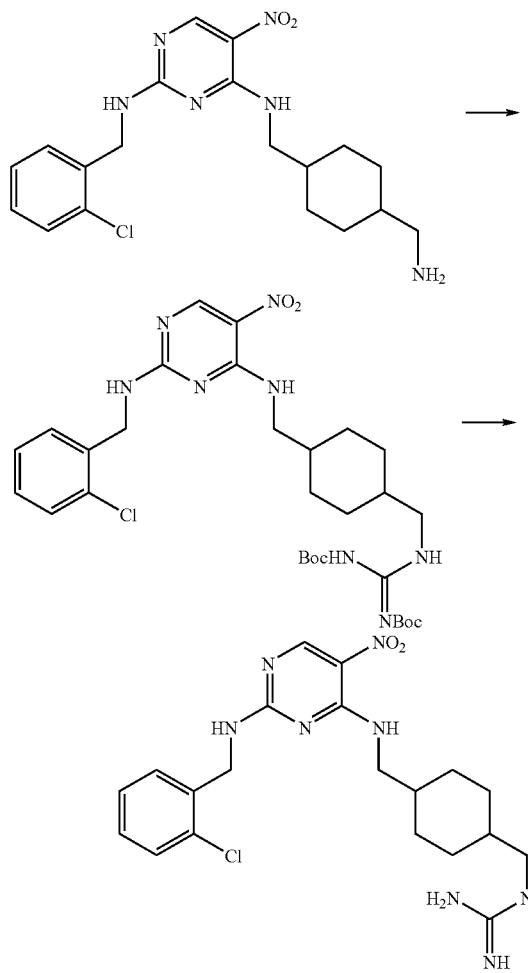

9

A mixture of N$^4$-(4-aminomethyl-cyclohexylmethyl)-5-nitro-N$^2$-(2-chloro-benzyl)-pyrmidine-2,4-diamine (110 mg, 270 mmol) and 1,3-bis(tert-butoxycarbonyl)-2-methyl thiopseudourea (95 mg, 330 mmol) in THF (5.0 mL) was stirred at room temperature for 3 days. The reaction mixture was then concentrated and purified by silica gel chromatography using a gradient of EtOAc in hexanes as the eluant to provide 52 mg (30% yield) of the bis(tert-butoxycarbonyl) protected guanidine a white solid, m/z calculated for C$_{30}$H$_{43}$ClN$_8$O$_6$: 647.2, found: 648.8 (M+H)$^+$.

The above bis(tert-butoxycarbonyl) protected guanidine was treated with 4N HCl/dioxane solution and stirred at room temperature for 14 h. The reaction mixture was concentrated and the resulting residue was purified by silica gel chromatography using a gradient of ammonium hydroxide and MeOH in dichloromethane as the eluant to provide 12 mg (37% yield) of the title compound as a light yellow solid, m/z calculated for C$_{20}$H$_{27}$ClN$_8$O$_2$: 446.0 found: 447.1 (M+H)$^+$.

Example 10

Synthesis of N-(3-{[2-(2-chloro-benzylamino)-5-nitro-pyrimidin-4-ylamino]-methyl}-cyclohexylmethyl)-guanidine

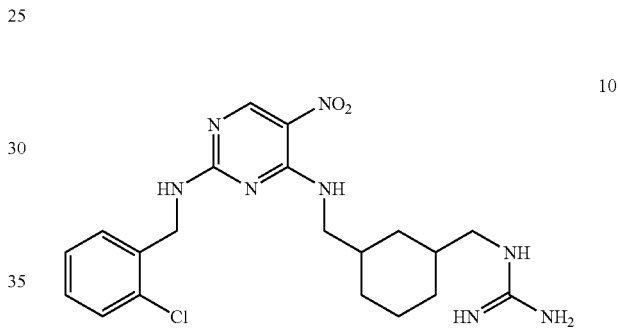

10

This compound was prepared in an analogous fashion to Example 9 using 1,3-cyclohexane bis (methylamine) as a starting material in place of 1,4-cyclohexane bis(methylamine), m/z calculated for C$_{20}$H$_{27}$ClN$_8$O$_2$: 446.0 found: 447.4 (M+H)$^+$.

Example 11

Synthesis of N$^2$-(2-chloro-benzyl)-5-nitro-N$^4$piperidin-4-ylmethyl-pyrimidine2,4-diamine

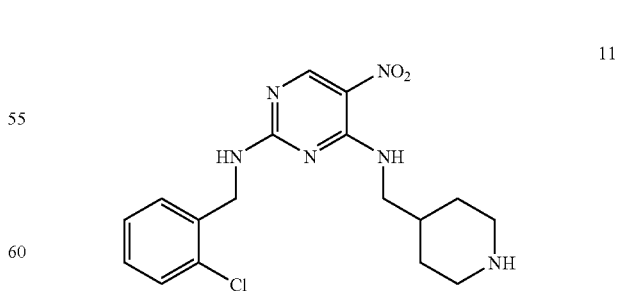

11

This compound was prepared by the procedure described in Example 1 using 2,5-dichloro-5-nitropyrimidine and 4-aminomethyl-1-N-Boc piperidine as starting materials. Subsequent treatment of the tert-butoxycarbonyl intermedi-

Example 12

Synthesis of 4-{[2-(2-chloro-benzylamino)-5-nitro-pyrimidin-4-ylamino]-methyl}-piperidine-1-carboxamidine

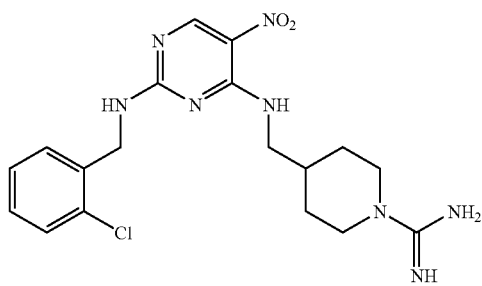

12

This compound was prepared in an analogous fashion to Example 9 using $N^2$-(2-Chloro-benzyl)-5-nitro-$N^4$piperidin-4-ylmethyl-pyrimidine2,4-diamine (Example 11) as a starting material in place of $N^4$-(4-Aminomethyl-cyclohexylmethyl)-5-nitro-$N^2$-(2-chloro-benzyl)-pyrmidine-2,4-diamine, m/z calculated for $C_{18}H_{23}ClN_8O_2$: 418.0 found: 419.1 (M+H)$^+$.

Example 13

Synthesis of 3-({4-[(4-aminomethyl-cyclohexylmethyl)-amino]-5-nitro-pyrimidin-2-ylamino}-methyl)-N-(2-o-tolyl-ethyl)-benzamide

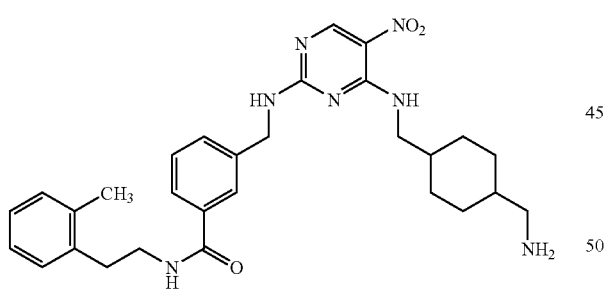

13

This compound was prepared in an analogous fashion to $N^4$-(4-aminomethyl-cyclohexylmethyl)-5-nitro-$N^2$-(2-chloro-benzyl)-pyrmidine-2,4-diamine using 3-aminomethyl-N-(2-o-tolyl-ethyl)-benzamide as a starting material in place of 2-chloro benzylamine, m/z calculated for $C_{29}H_{37}N_7O_3$: 531.0 found: 532.4 (M+H)$^+$.

3-Aminomethyl-N-(2-o-tolyl-ethyl)-benzamide was prepared as follows:

A solution of N-Boc-3-aminomethyl benzoic acid (1.00 g, 3.98 mmol), HOBT (600 mg, 4.44 mmol), and EDC (805 mg, 4.20 mmol) in DMF (10 mL) was stirred at room temperature for 30 min. 2-Methyl phenethylamine (575 uL, 4.08 mmol) was then added dropwise and the reaction mixture was stirred overnight at room temperature. The reaction mixture was concentrated and the resulting residue was taken up in EtOAc (50 mL) and washed successively with NaHCO$_3$ satd (2×50 mL) and 1N HCl (2×50 mL). The organic phase was dried (MgSO$_4$) and concentrated to provide 1.37 g (93% yield) of the tert-butoxycarbonyl protected intermediate as a white solid, m/z calculated for $C_{22}H_{28}N_2O_3$: 368.0 found: 369.4 (M+H)$^+$.

The above tert-butoxycarbonyl protected intermediate was treated with 4N HCl/dioxane to provide the desired starting material,

Example 14

Synthesis of 4-{4-[(4-aminomethyl-cyclohexylmethyl)-amino]-5-nitro-pyrimidin-2-ylamino}-N-(2-o-tolyl-ethyl)-butyramide

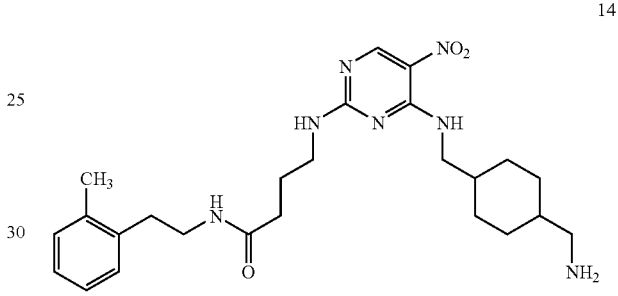

14

This compound was prepared in an analogous fashion to Example 13 using 4-tert-butoxycarbonyl aminobutyric acid as a starting material in place of N-Boc-3-aminomethyl benzoic acid, m/z calculated for $C_{25}H_{37}N_7O_3$: 483.0 found: 484.5 (M+H)$^+$.

Example 15

Synthesis of 5-{4-[(4-aminomethyl-cyclohexylmethyl)-amino]-5-nitro-pyrimidin-2-ylamino}-pentanoic acid (2-o-tolyl-ethyl)-butyramide

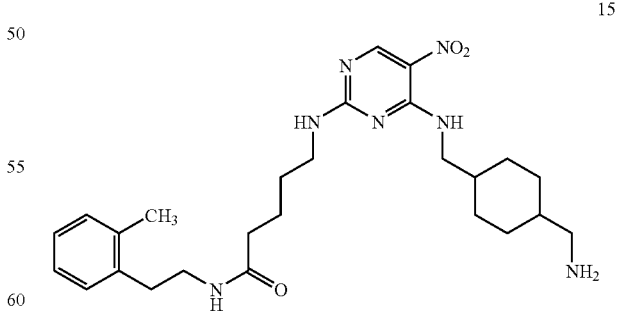

15

This compound was prepared in an analogous fashion to Example 13 using 5-tert-butoxycarbonyl aminovaleric acid as a starting material in place of N-Boc-3-aminomethyl benzoic acid, m/z calculated for $C_{26}H_{39}N_7O_3$: 497.0 found: 498.4 (M+H)$^+$.

Example 16

Synthesis of 6-{4-[(4-aminomethyl-cyclohexylmethyl)-amino]-5-nitro-pyrimidin-2-ylamino}-hexanoic acid (2-o-tolyl-ethyl)-butyramide

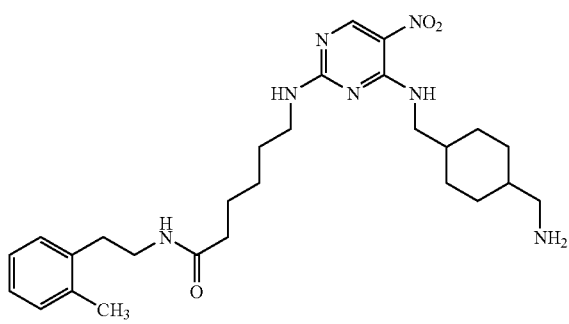

16

This compound was prepared in an analogous fashion to Example 13 using 6-tert-butoxycarbonylamino hexanoic acid as a starting material in place of N-Boc-3-aminomethyl benzoic acid, m/z calculated for $C_{27}H_{41}N_7O_3$: 511.0 found: 512.5 $(M+H)^+$.

Example 17

Synthesis of $N^4$-{[4-(aminomethyl)cyclohexyl]methyl}-N-2-(2-bromobenzyl)-5-nitropyrimidine-2,4-diamine

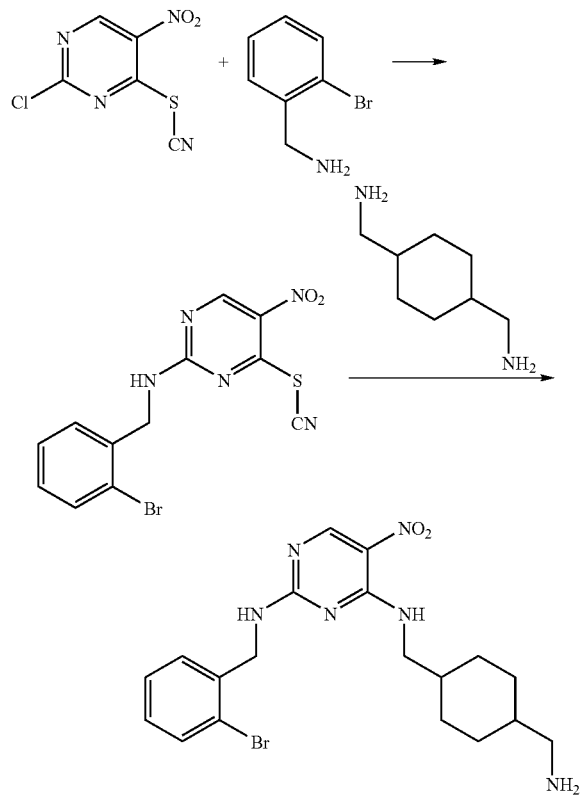

17

2-Chloro-5-nitro-4-thiocyanatopyrimidine (100 mg, 0.46 mmol) was suspended in 1 mL absolute EtOH. o-Bromobenzylamine hydrochloride (103 mg, 0.46 mmol) was dissolved in 1 mL absolute EtOH and added to the reaction quickly at ambient temperature. Then triethylamine (129 µL, 0.92 mmol) was added dropwise via syringe. The reaction was stirred 16 h at ambient temperature. The resulting precipitate was filtered providing 136 mg of the desired (2-bromo-benzyl)-(5-nitro-4-thiocyanato-pyrimidin-2-yl)-amine as a white solid.

1,4-Cyclohexanebis(methylamine) (65 mg, 0.46 mmol) was dissolved in 1 mL dichloromethane and added to a suspension of (2-bromo-benzyl)-(5-nitro-4-thiocyanato-pyrimidin-2-yl)-amine (40 mg, 0.11 mmol) in 1 mL dichloromethane. The reaction was shaken 16 h at ambient temperature. The reaction mixture was then loaded directly onto a 4.5 g pre-packed disposable flash cartridge and eluted with a gradient (solvent system: A=dichloromethane and B=10% ammonium hydroxide in MeOH). The title compound (43 mg, 89%) was isolated as a yellow solid.

Example 18

Synthesis of $N^4$-(4-aminomethyl-cyclohexylmethyl)-5-nitro-$N^2$-(1-phenyl-cyclopropyl)-pyrimidine-2,4-diamine

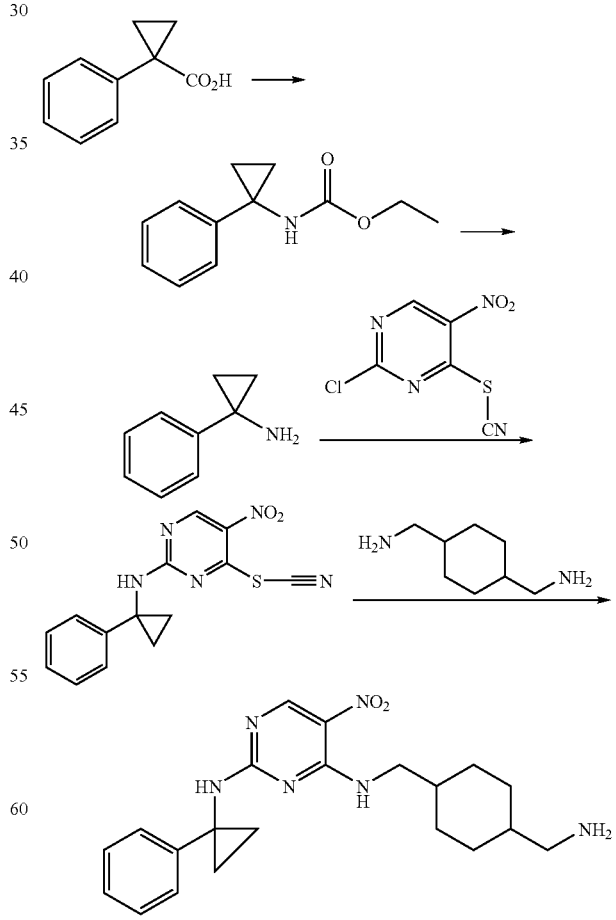

18

To a solution of 1.0 g (6.2 mmol) of 1-phenyl-1-cyclopropane carboxylic acid in CH$_2$Cl$_2$ (30 mL) at room temperature was added 2.0 mL (9.0 mmol) of diphenylphosphoryl azide (DPPA) and 1.3 mL (9.3 mmol) of triethylamine. The reaction mixture was stirred at room temperature for 3 h then poured into ice water and acidified to pH 2 with 6N HCl. The phases were separated and the aqueous phase washed with CH$_2$Cl$_2$. The combined organics were washed with H$_2$O followed by brine then dried over anhydrous Na$_2$SO$_4$ and concentrated under reduced pressure. The residue was taken up in EtOH (30 mL) and heated at reflux for 8 h. The reaction was cooled to room temperature and concentrated under reduced pressure. The residue was diluted with EtOAc and washed with H$_2$O followed by brine then dried over anhydrous Na$_2$SO$_4$ and concentrated under reduced pressure to provide a white oil. The product was purified by flash silica gel chromatography using a 0-10% graident of EtOAc:hexanes to provide (1-phenyl-cyclopropyl)-carbamic acid ethyl ester 0.85 g (69%) as a white solid. m/z cacld. C$_9$H$_{12}$N [M-ethylcarbamate+H]$^+$ 134.20. Found: 133.90.

To a suspension of 0.84 g (4.1 mmol) of the above carbamate in a 1:2 mixture of H$_2$O:ethylene glycol (4.5 mL) was added 1.0 g (25 mmol) of sodium hydroxide as a solid in one portion. The slurry was heated to 110° C. for 15 h during which time a solid precipitated out of solution. The mixture was cooled to room temperature and poured into a solution of 2N HCl (30 mL). The mixture was washed with Et$_2$O and the aqueous layer made basic to pH 12 by addition of 6N NaOH. The aqueous phase was washed with CH$_2$Cl$_2$ and the combined organic phase was dried over anhydrous Na$_2$SO$_4$ and concentrated under reduced pressure to provide 0.046 g (8%) of 1-phenyl-cyclopropylamine as a clear oil. m/z cacld. C$_9$H$_{12}$N [M+H]$^+$: 134.20. Found: 133.90.

(5-Nitro-4-thiocyanato-pyrimidin-2-yl)-(1-phenyl-cyclopropyl)-amine was prepared by addition of the above amine to 2-chloro-5-nitro-4-thiocyanato-pyrimidine using the procedure described in Example 17. m/z calcd. C$_{14}$H$_{10}$N$_5$O$_2$S [M−H]$^−$: 312.33. Found: 312.10.

The title compound was prepared from the above intermediate by addition of 1,4-cyclohexanebis(methylamine) using the procedure described in Example 17. m/z calcd. C$_{21}$H$_{29}$N$_6$O$_2$ [M+H]$^+$: 397.50. Found: 397.04.

Example 19

Synthesis of N$^4$-(4-aminomethyl-cyclohexylmethyl)-N$^2$-[1-(2-chloro-phenyl)-1-methyl-ethyl]-5-nitro-pyrimidine-2,4-diamine

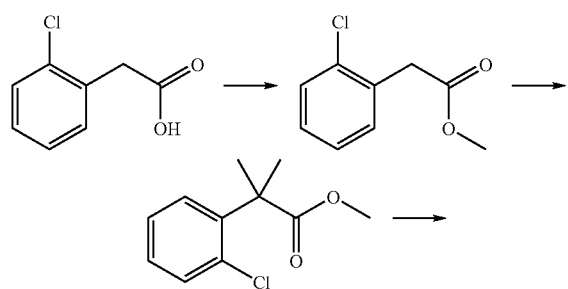

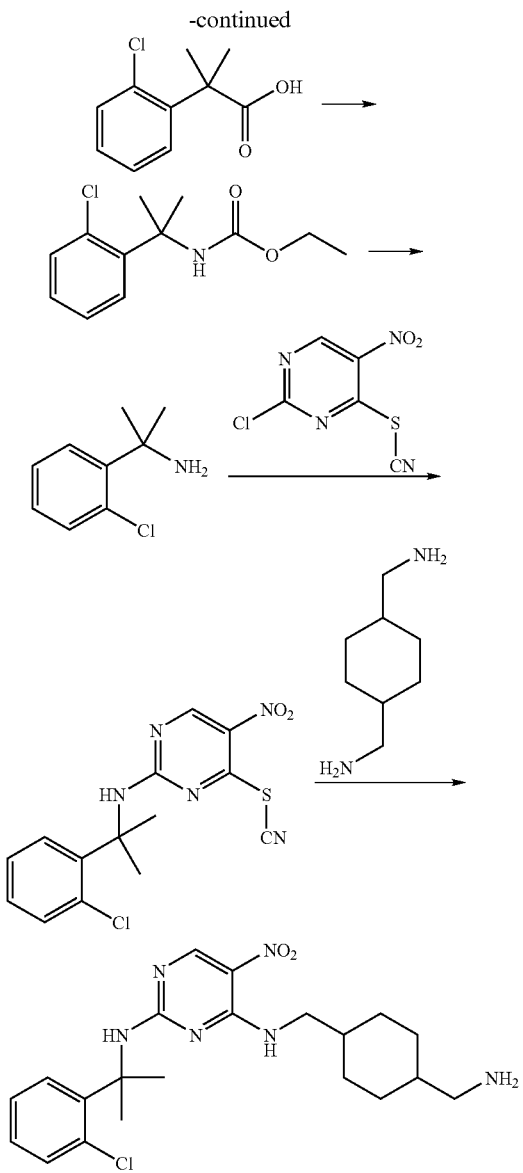

To a solution of 10.0 g (59 mmol) (2-chlorophenyl)acetic acid in MeOH (10 mL) was added 9.6 mL (88 mmol) of trimethyl orthoformate and 0.32 mL (6.0 mmol) of H$_2$SO$_4$. The reaction was stirred at room temperature for 4 h then diluted with EtOAc and washed with H$_2$O followed by a saturated aqueous solution of NaHCO$_3$. The organic phase was dried over anhydrous Na$_2$SO$_4$ and concentrated under reduced pressure to provide 10.6 g (97%) of (2-chlorophenyl)-acetic acid methyl ester as a clear oil. The crude reaction product was not purified but used immediately.

To a mixture of 2.0 g (11 mmol) of the above ester and 1.4 mL (11 mmol) of iodo methane in THF (50 mL) cooled to 0° C. was added dropwise a solution of sodium bis(trimethylsilyl)amide (22 mL of a 1.0 M solution in THF). The reaction was allowed to slowly warm up to room temperature and stirred for 14 h. The reaction was cooled to 0° C. and an additional 1.4 mL (11 mmol) of iodo methane was added. To this mixture was added dropwise a solution of sodium bis (trimethylsilyl)amide (22 mL of a 1.0 M solution in THF). The reaction was allowed to slowly warm to room temperature and stirred for 8 h. The mixture was cooled to 0° C. and the reaction was quenched by addition of a saturated aqueous solution of $NH_4Cl$. The mixture was diluted with $H_2O$ and extracted with EtOAc. The combined organic phase was washed with brine, dried over anhydrous $Na_2SO_4$, and concentrated under reduced pressure to provide 2.2 g (95%) of 2-(2-chlorophenyl)-2-methyl-propionic acid methyl ester as a brown oil.

To a solution of 2.2 g (10 mmol) of the above ester in MeOH (60 mL) was added an aqueous solution of KOH (60 mL of a 1.0 M solution). The reaction mixture was heated to reflux for 15 h. The mixture was cooled to room temperature and washed with $Et_2O$ then acidified to pH 2 with a solution of 2N HCl. The aqueous layer was extracted with $CH_2Cl_2$, dried over anhydrous $Na_2SO_4$ and concentrated under reduced pressure to provide 0.55 g (27%) of 2-(2-chlorophenyl)-2-methyl-propionic acid as a light brown solid. The crude reaction product was not purified but used immediately.

To a solution of 0.55 g (2.8 mmol) of the above acid in $CH_2Cl_2$ (15 mL) at room temperature was added 0.90 mL (4.2 mmol) of DPPA and 0.58 mL (4.1 mmol) of triethyl amine. The reaction mixture was stirred at room temperature for 3 h then poured into ice water and acidified to pH 2 with 6N HCl. The phases were separated and the aqueous phase washed with $CH_2Cl_2$.

The combined organics were washed with $H_2O$ followed by brine then dried over anhydrous $Na_2SO_4$ and concentrated under reduced pressure. The residue was taken up in EtOH (15 mL) and heated at reflux for 15 h. The reaction was cooled to room temperature and concentrated under reduced pressure. The crude residue was purified by flash silica gel chromatography using a 0-10% gradient of EtOAc:hexanes to provide 0.31 g (46%) of [1-(2-chlorophenyl)-1-methyl-ethyl]-carbamic acid ethyl ester a clear oil. m/z calcd. $C_{12}H_{17}ClNO_2$ [M+H]$^+$: 242.73. Found: 241.97.

To a suspension of 0.31 g (1.3 mmol) in a 1:2 mixture of $H_2O$:ethylene glycol (4.5 mL) was added 0.30 g (7.5 mmol) of sodium hydroxide as a solid in one portion. The slurry was heated to 110° C. for 15 h during which time a solid precipitated out of solution. The reaction was cooled to room temperature and poured into a solution of 2N HCl (30 mL) the reaction was washed with $Et_2O$ and the aqueous layer made basic to pH 12 by addition of 6N NaOH. The aqueous phase was washed with $CH_2Cl_2$ and the combined organic phase was dried over anhydrous $Na_2SO_4$ and concentrated under reduced pressure to provide 0.078 g (36%) of 1-(2-chlorophenyl)-1-methyl-ethylamine a clear oil. m/z calcd. $C_9H_{13}ClN$ [M+H]$^+$: 170.66. Found: 169.91.

[1-(2-Chlorophenyl)-1-methyl-ethyl]-(5-nitro-4-thiocyanato-pyrimidin-2-yl)-amine was prepared by addition of the above amine to 2-chloro-5-nitro-4-thiocyanato-pyrimidine using the procedure described in Example 17. m/z calcd. $C_{14}H_{11}N_5O_2S$ [M−H]$^−$: 348.79. Found: 348.05.

The title compound was prepared from the above intermediate by addition of 1,4-cyclohexanebis(methylamine) using the procedure described in Example 17. m/z calcd. $C_{21}H_{30}ClN_6O_2$ [M+H]$^+$: 433.97. Found: 433.04.

Example 20

Synthesis of $N^4$-(4-dimethylaminomethyl-cyclohexylmethyl)-$N^2$-(2-methylsulfanyl-benzyl)-5-nitropyrimidine-2,4-diamine

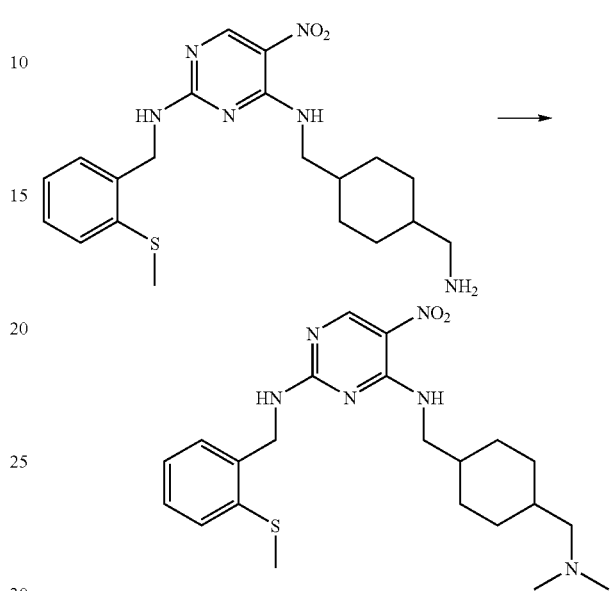

To a solution of 0.035 g (0.08 mmol) of $N^4$-(4-aminomethyl-cyclohexylmethyl)-$N^2$-(2-methylsulfanyl-benzyl)-5-nitro-pyrimidine-2,4-diamine (prepared by the procedure described in Example 17, using 2-methylsulfanyl-benzylamine) in MeOH (1 mL) containing 1% v/v AcOH and cooled to 0° C. was added 0.03 mL (0.4 mmol) of a 37% aqueous formaldehyde solution. To this mixture was added 0.010 g (0.16 mmol) of sodium cyanoborohydride as a solid in one portion. The reaction mixture was allowed to slowly warm to room temperature and stirred for 2 h. The reaction was diluted with a saturated aqueous solution of $NaHCO_3$ and washed with $CH_2Cl_2$. The combined organic phase was dried over anhydrous $Na_2SO_4$ and concentrated under reduced pressure. The residue was purified by flash silica gel chromatography using a 0-40% gradient of A (18% MeOH, 2% $NH_4OH$, 80% $CH_2Cl_2$) to B ($CH_2Cl_2$) to provide 0.0083 g (22%) of a white powder. m/z calcd. $C_{22}H_{32}N_6O_2S$ [M+H]$^+$: 445.6. Found: 445.5.

The other specific compounds listed in the Table set forth previously were prepared by methods analogous to those set forth in the General Synthetic Methods section and the Synthetic Examples above.

Assessment of Biological Activity

PKC-Theta Inhibition Assay

The ability of compounds to inhibit the kinase activity of PKC-theta was measured using a competitive Fluorescent Polarization Assay (PanVera R2748). Human recombinant PKC-theta (PanVera R2996), was used at a final concentration of 50 nM in a kinase assay buffer (20 mM HEPES, pH 7.6, 10 mM $MgCl_2$, 0.1 mM $CaCl_2$, 0.01% CHAPS, 100 microM OrthoVanadate (Sigma), Protease Inhibitor Cocktail (Roche), 200 microM TCEP). PKC-theta was incubated with test compound for 10 minutes at room temperature. PKC-alpha pseudosubstrate (RFARKGSLRQKNV; PanVera R2760) at a final concentration of 1 microM and ATP (Amersham 27-2056-01) at a final concentration of 10 microM were added and incubated 60 minutes at room temperature. The kinase reaction was stopped by adding an anti-phosphoserine containing peptide antibody and fluorescein-labeled phosphopeptide tracer ("F-phosphopeptide") diluted in a quench buffer containing EDTA. The FP reaction was incubated for 90 minutes at room temperature. Phosphopeptide, generated by the kinase activity of PKC-theta, competes with the F-phosphopeptide for the anti-phosphopeptide antibody. Inhibition of kinase activity will result in the binding of the antibody to the F-phosphopeptide, yielding an increase in the fluorescence polarization. Change in polarization was measured on an LJL Criterion Analyst with 485 nm excitation filter, 530 nm emission filter, and 505 nm dichroic mirror.

All compounds in the synthetic examples and Tables above were evaluated in the PKC-theta assay above and were found to have $IC_{50}$'s less than 10 microM. Preferred compounds had $IC_{50}$'s equal to or less than 0.3 microM.

Many of the compounds in the synthetic examples and Tables above were also tested against Syk, Lyn, Veg-f and insulin receptor kinase to evaluate selectivity for PKC-theta inhibition. Some compounds were also tested against other kinases including CDK-5, CDK-1 and PLK. Many of the compounds demonstrated selectivity for the inhibition of PKC-theta as compared to one or more of the other kinases tested.

Assay conditions for testing against other kinases are generally known in the art. Examples of suitable assays that can be used are described below:

SYK Kinase Assay

SYK is purified as a GST-fusion protein. The kinase activity is measured using DELFIA (Dissociation Enhanced Lanthanide Fluoroimmunoassay) which utilizes europium chelate-labeled anti-phosphotyrosine antibodies to detect phosphate transfer to a random polymer, poly $Glu_4$: $Tyr_1$ (PGTYR).

The kinase assay is performed in kinase assay buffer (50 mM HEPES, pH 7.0, 25 mM $MgCl_2$, 5 mM $MnCl_2$, 50 mM KCl, 100 μM $Na_3VO_4$, 0.2% BSA, 0.01% CHAPS). Test samples initially dissolved in DMSO at 1 mg/mL, may be pre-diluted for dose response (11 doses with starting final concentration of 30 μg/mL, 1 to 3.5 serial dilutions) with the assay buffer in 96-well polypropylene microtiter plates. A 25 μL aliquot of this diluted sample is added to neutravidin coated 96-well white plate (PIERCE). A 25 μL volume of diluted enzyme (0.6 ng/mL final conc.) and a 50 μL volume of a mixture of substrates containing 200 nM ATP and 3.6 ng/μL PGTYR-biotin (CIS Biointernational) in kinase buffer is sequentially added to the assay plates. Background wells are incubated with buffer, rather than 25 μL enzyme. The assay plates are incubated for 30 minutes at room temperature. Following incubation, the assay plates are washed three times with 300 μL wash buffer (50 mM Tris-HCL, pH 7.4, 150 mM NaCl, 0.05% Tween 20, 0.2% BSA). A 100 μL aliquot of europium-labeled anti-phosphotyrosine ($Eu^{3+}$-PT66, Wallac CR04-100) diluted in 50 mM Tris-HCl, pH 7.8, 150 mM NaCl, 10 μM DTPA, 0.05% Tween 40, 0.2% BSA, 0.05% BGG (1 nM final conc.) is added to each well and incubated for 30 minutes at room temperature. Upon completion of the incubation, the plate is washed four times with 300 μL of wash buffer and 100 μL of DELFIA Enhancement Solution (Wallac) is added to each well. After 10 minutes or longer, time-resolved fluorescence is measured on the LJL's Analyst (excitation at 360 nm, emission at 620 nm, EU 400 Dichroic Mirror) after a delay time of 250 μs.

CDK Kinase Assay

1. Preparation of Recombinant Cyclin-CDK Enzymes

The corresponding cDNAs for human cyclin B1 (cyclin E, or. cyclin D1) and human CDK1 (CDK2, or. CDK4) are cloned by standard methods using RT-PCR, and cloned into a transfer vector (cyclin in pAcG2T made by Pharmingen, CDKs in p2Bac made by Invitrogen) for the baculovirus system. Recombinant cyclin B1-CDK1 (or cyclin E-CDK2, cyclin D1-CDK4) is expressed in High Five insect cells (*Trichoplusia ni*) by coinfection with both recombinant baculoviruses (after the 4th round of amplification, $>1\times10^8$ viruses/ml). 72 h after the infection the High Five cells are harvested, and deep-frozen in liquid nitrogen. After thawing the cells are resuspended in lysing buffer (50 mM HEPES pH 7.5, 10 mM $MgCl_2$, 1 mM DTT, 5 μg/ml leupeptin, 5 μg/ml aprotinin, 100 μM NaF, 100 μM PMSF, 10 mM β-glycerolphosphate, 100 μM $Na_3VO_4$, 30 mM nitrophenylphosphate, 17.5 ml of lysing buffer per $10^8$ cells) and incubated on ice for 30 min. The cell lysate is freed from the cell debris by centrifugation and the quantity of recombinant cyclin B1-CDK1 enzyme (or cyclin E-CDK2, cyclin D1-CDK4) in the total lysate (about 1-5 mg/ml) is determined by SDS-polyacrylamide gel electrophoresis. Cyclin D1-CDK4 is purified by means of a GST-tag on cyclin D1 and then using glutathione beads (total protein about 0.2 mg/ml).

2. Cyclin B1-CDK1 Kinase Inhibition Test

All the kinase tests may be carried out in 96-well microtitre plates (Greiner PS) in a final volume of 60 μl. The kinase test contain 1% DMSO (v/v), 5 μg of histone H1 (calf thymus, Roche Molecular Biochemicals), 1 to 5 μg of a cell lysate with recombinant cyclin B1/CDK1, the test substance (in a final concentration of 1 nM to 10 μM) and kinase buffer (15 mM MgCl2, 25 mM MOPS, pH 7.0, 0.1 mM DTT). As a negative control the kinase reaction is carried out in the absence of the substrate histone H1. As a positive control the kinase reaction is carried out in the absence of a test substance. As an internal control 30 μM and 300 μM (final concentration) of the kinase inhibitor olomoucin (Alexis) are used.

The PS microtitre plates are placed on ice, and 10 μl of the test substance, in different concentrations (in each case in 6% DMSO), 20 μl of the histone H1 (250 μg/ml in kinase buffer) and 20 μl of cyclin B1/CDK1 (1 to 5 μg of the recombinant cell lysate in 20 μl of kinase buffer) are pipetted in and mixed together. The kinase reaction is started by the addition of 10 μL of ATP mix (0.045 mM ATP, 0.5 μCi [γ-$^{33}$P]ATP in kinase buffer) and incubated for 30 min at 30° C. and 600 rpm in a shaking incubator. After incubation the plates are placed on ice and the proteins are precipitated by the addition of 125 μl of ice-cold 5% trichloroacetic acid. After 15 min on ice the precipitates are transferred onto Packard Unifilter 96 GF/B plates with the Packard Harvester System, and collected by vacuum filtration. The precipitates are washed 4 times with dist. $H_2O$ at ambient temperature. The filter plates are then dried at 60° C. and 50 μl of scintillation liquid are added to each well (Ultima Gold, Packard). The plate is sealed up with Sealing Tape and after 1 h measured in a scintillation measuring apparatus (Micro Beta made by Wallac). The inhibition of the substances is calculated as a percentage of the control (cyclin B1-CDK1 without inhibitor) and the active substance concentration which inhibits the enzyme activity by 50% (IC50) is derived.

3. Cyclin E-CDK2 Kinase Inhibition Test

The inhibition test with cyclin E-CDK2 is carried out using the same method as for cyclin B1-CDK1, except that recombinant cyclin E-CDK2 is used as the enzyme.

4. Cyclin D1-CDK4 Kinase Inhibition Test

For the inhibition test with cyclin D1-CDK4, recombinant Retinoblastoma Protein (pRB) from aa379-928, which contains a GST-tag at the N-terminus, is used as the substrate. GST-pRB is expressed in bacteria and then purified using glutathione beads (about 0.2 mg/ml). The kinase test contains 1% DMSO (v/v), 10 µg pRB, 0.4 µg of a cell lysate with recombinant cyclin D1-CDK4, the test substance (final concentration from 1 nM to 10 µM) and kinase buffer (15 mM MgCl2, 25 mM MOPS, pH 7.0, 0.1 mM DTT). As a negative control the kinase reaction is carried out in the absence of the substrate pRB. As a positive control the kinase reaction is carried out in the absence of a test substance. As an internal control 30 µM and 300 µM (final concentration) of the kinase inhibitor olomoucin (Alexis) are used.

The PS microtitre plates are placed on ice, and 10 µl of the test substance, in different concentrations (in each case in 6% DMSO), 20 µl of pRB (10 µg in kinase buffer) and 20 µl of cyclin D1-CDK4 (0.4 µg of the recombinant cell lysate in 20 µL of kinase buffer) are pipetted in and mixed together. The kinase reaction is started by the addition of 10 µl of ATP mix (0.045 mM ATP, 1 µCi [$\gamma$-$^{33}$P]ATP in kinase buffer) and incubated for 45 min at 32° C. and 600 rpm in a vibrating incubator. After incubation, 50 µl of the reaction mixture are pipetted onto P81 filters (Whatmann). After 20 sec reaction time the filters are washed 4 times with 1.5% phosphoric acid (about 5 min per washing step) while shaking them gently. After washing the filters are dried at 85° C., scintillation liquid is added and the scintillation is measured in a scintillation counter (Micro Beta made by Wallac).

Methods of Therapeutic Use

The compounds of the invention are effective inhibitors of PKC-theta activity, and therefore are useful to inhibit PKC-theta activity in a patient and treat a variety of diseases and disorders that are mediated or sustained through the activity of PKC-theta.

Without wishing to be bound by theory, the compounds of this invention would be expected to inhibit T cell activation via effective inhibition of PKC-theta, and are therefore useful to treat diseases and disorders associated with T cell activation. For example, the inhibition of T cell activation is therapeutically useful for selectively suppressing the immune function. Thus, the inhibition of PKC-theta with the compounds of this invention is an attractive means for treating a variety of immunological disorders, including inflammatory diseases, autoimmune diseases, organ and bone marrow transplant rejection and other disorders associated with T cell mediated immune response. In particular, the compounds of the invention may be used to treat acute or chronic inflammation, allergies, contact dermatitis, psoriasis, rheumatoid arthritis, multiple sclerosis, type I diabetes, inflammatory bowel disease, Guillain-Barre syndrome, Crohn's disease, ulcerative colitis, graft versus host disease (and other forms of organ or bone marrow transplant rejection) and lupus erythematosus. Other disorders associated with T cell-mediated immune responses will be evident to those of ordinary skill in the art and can also be treated with the compounds and compositions of this invention.

In addition, PKC theta activation has been shown to be associated with insulin resistance in skeletal muscle. Therefore, the inhibition of PKC-theta with the compounds of this invention is also an attractive means for treating type II diabetes.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

We claim:

1. A compound of the following formula (I):

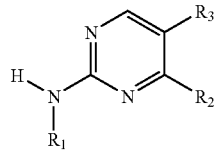

wherein:
R$_1$ is C$_{1-8}$alkyl, C$_{3-7}$cycloalkyl, C$_{3-7}$cycloalkyl-C$_{1-8}$alkyl, naphthyl, quinolinyl, aryl-C$_{1-8}$alkyl, or heteroaryl-C$_{1-8}$alkyl, wherein in each of the C$_{1-8}$alkyl groups a methylene group may optionally be replaced by —NHC(O)— or —C(O)NH—, and wherein each of the C$_{1-8}$alkyl groups is optionally substituted by an oxo group or one or more C$_{1-3}$alkyl groups wherein two alkyl substituents on the same carbon atom of a C$_{1-8}$alkyl group may optionally be combined to form a C$_{2-5}$ alkylene bridge, and wherein the aryl group is optionally substituted on adjacent carbon atoms by a C$_{3-6}$alkylene bridge group wherein a methylene group is optionally replaced by an oxygen, —S—, —S(O)—, —SO$_2$— or —N(R$_6$)—;

or R$_1$ has the following structure:

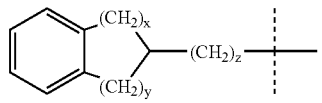

wherein x and y are independently 0, 1, 2, 3 or 4, provided that x+y is 2 to 4, z is 0, 1 or 2, and one or two CH$_2$ groups in the ring may optionally be replaced by —O—, —S—, —S(O)—, —SO$_2$— or —N(R$_6$);

wherein each R$_1$ group is optionally substituted by one or more of the following groups: C$_{1-6}$alkyl, C$_{3-6}$cycloalkyl, halogen, nitro, hydroxy, C$_{1-6}$alkyloxy, C$_{1-6}$alkylthio, aryl, arylC$_{1-6}$alkyl, aryloxy, arylthio, aminosulfonyl, or amino optionally substituted by one or two C$_{1-6}$alkyl groups, wherein each aryl group is optionally substituted by one or more C$_{1-6}$alkyl, halogen, nitro, hydroxy or amino optionally substituted by one or two C$_{1-6}$alkyl groups, and wherein in each of the C$_{1-6}$alkyl groups a methylene group may optionally be replaced by —NHC(O)— or —C(O)NH—, and wherein each of the C$_{1-6}$alkyl groups is optionally substituted by one or more halogens;

R$_2$ is selected from the following groups:

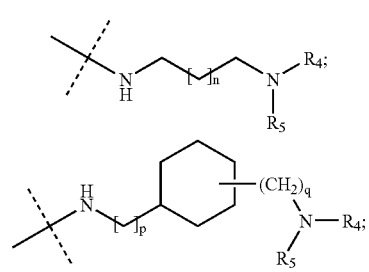

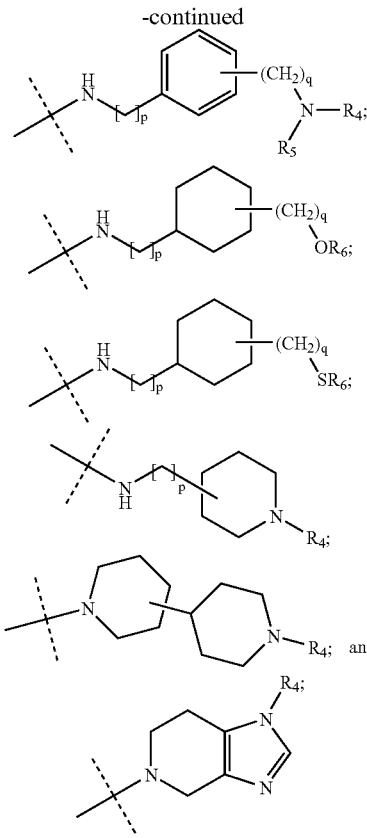

wherein:
n is an integer from 3 to 8;
p is an integer from 1 to 3;
q is an integer from 0 to 3;
R$_4$ and R$_5$ are each independently selected from hydrogen, C$_{1-6}$alkyl, arylC$_{1-6}$alkyl, or amidino, wherein each aryl group is optionally substituted by one or more C$_{1-6}$alkyl, halogen, nitro, hydroxy or amino optionally substituted by one or two C$_{1-6}$alkyl groups, and wherein each of the C$_{1-6}$alkyl groups is optionally substituted by one or more halogens, and wherein the amidino is optionally substituted by one to three C$_{1-6}$alkyl;
R$_6$ is hydrogen or C$_{1-6}$alkyl;
wherein each R$_2$ group is optionally substituted by one or more C$_{1-6}$alkyl, C$_{1-6}$alkoxy, CN, —OH, —NH$_2$ or halogen;
R$_3$ is halogen, cyano, nitro, C$_{1-6}$alkyl, C$_{1-6}$alkyloxycarbonyl or aminocarbonyl;
or a tautomer, or pharmaceutically acceptable salt thereof, or a corresponding compound having at least one amine group protected by an amino-protecting group;
with the proviso that the following trisubstituted pyrimidine compounds are excluded:
2-(benzylamino)-4-(4-aminomethyl-cyclohexylmethylamino)-5-nitro-pyrimidine; and
2-(2-chlorobenzylamino)-4-(4-aminomethyl-cyclohexylmethylamino)-5-nitro-pyrimidine.

2. A compound of formula (I) according to claim 1, wherein:
R$_1$ is aryl-C$_{1-4}$alkyl or heteroaryl-C$_{1-4}$alkyl, wherein in each of the C$_{1-4}$alkyl groups a methylene group may optionally be replaced by —NHC(O)— or —C(O)NH—, and wherein each of the C$_{1-4}$alkyl groups is optionally substituted by an oxo group or one or more $C_{1-3}$alkyl groups wherein two alkyl substituents on the same carbon atom of a $C_{1-4}$alkyl group may optionally be combined to form a $C_{2-5}$ alkylene bridge, and wherein the aryl group is optionally substituted on adjacent carbon atoms by a $C_{3-6}$alkylene bridge group wherein a methylene group is optionally replaced by an oxygen, sulfur or —N($R_6$)—;

or $R_1$ has the following structure:

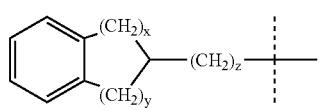

wherein x and y are independently 0, 1, 2 or 3, provided that x+y is 2 to 3, and z is 0 or 1;

wherein "heteroaryl" is defined as pyridyl, furyl, thienyl, pyrrolyl, imidazolyl, or indolyl;

wherein each $R_1$ group is optionally substituted by one or more of the following groups: $C_{1-6}$alkyl, Cl, Br, F, nitro, hydroxy, $CF_3$, —$OCF_3$, —$OCF_2H$, —$SCF_3$, $C_{1-4}$alkyloxy, $C_{1-4}$alkylthio, phenyl, benzyl, phenyloxy, phenylthio, aminosulfonyl, or amino optionally substituted by one or two $C_{1-3}$alkyl groups;

$R_2$ is selected from the following groups:

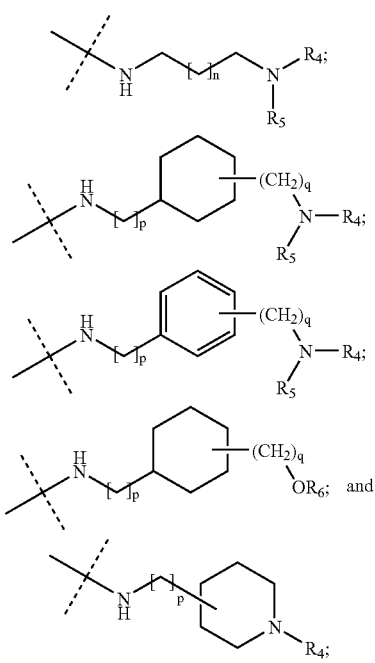

wherein:
n is an integer from 5 to 7;
p is an integer from 1 to 2;
q is an integer from 1 to 2;
$R_4$ and $R_5$ are each independently selected from hydrogen, $C_{1-6}$alkyl, aryl$C_{1-6}$alkyl, or amidino;
$R_6$ is hydrogen;
$R_3$ is Br, Cl, F, cyano or nitro;
or a tautomer, or pharmaceutically acceptable salt thereof; or a corresponding compound having at least one amine group protected by an amino-protecting group.

3. A compound of formula (I) according to claim 1, wherein:
$R_1$ is phenyl-$C_{1-4}$alkyl or naphthyl$C_{1-2}$alkyl,
wherein each $R_1$ group is optionally substituted by one or more of the following groups: methyl, Cl, Br, F, nitro, hydroxy, $CF_3$, —$OCF_3$, —$SCF_3$, $C_{1-4}$alkyloxy or $C_{1-4}$alkylthio;
$R_2$ is selected from the following groups:

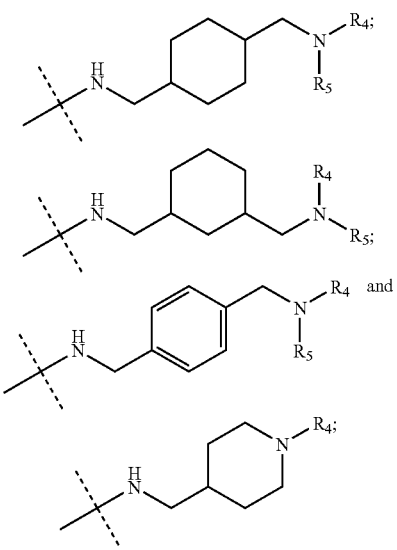

wherein:
$R_4$ and $R_5$ are each independently selected from hydrogen, $C_{1-3}$ alkyl, or amidino;
$R_3$ is Br, Cl, cyano or nitro;
or a tautomer, or pharmaceutically acceptable salt thereof; or a corresponding compound having at least one amine group protected by an amino-protecting group.

4. A compound of formula (I) according to claim 1, wherein:
$R_1$ is phenyl$CH_2$—
wherein the phenyl group is optionally substituted by one or more of the following groups: methyl, Cl, Br, F, nitro, hydroxy, $CF_3$, —$OCF_3$, —$SCF_3$, $C_{1-4}$alkyloxy or $C_{1-4}$alkylthio;
$R_2$ is selected from the following groups:

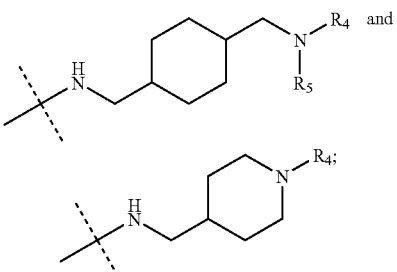

$R_3$ is nitro;
$R_4$ and $R_5$ are each independently selected from hydrogen, methyl, or amidino;
or a tautomer, or pharmaceutically acceptable salt thereof; or a corresponding compound having at least one amine group protected by an amino-protecting group.

5. A compound according to claim 1 selected from:

ethyl 4-({[4-(aminomethyl)cyclohexyl]methyl}amino)-2-[(2-chlorobenzyl)amino]pyrimidine-5-carboxylate $N^4$-{[4-(aminomethyl)cyclohexyl]methyl}-5-nitro-N-2-[(2R)-1,2,3,4-tetrahydronaphthalen-2-yl]pyrimidine-2,4-diamine $N^4$-{[4-(aminomethyl)cyclohexyl]methyl}-5-nitro-$N^2$-[(2S)-1,2,3,4-tetrahydronaphthalen-2-yl]pyrimidine-2,4-diamine $N^4$-{[4-(aminomethyl)cyclohexyl]methyl}-5-nitro-$N^2$-[(1R)-1,2,3,4-tetrahydronaphthalen-1-yl]pyrimidine-2,4-diamine $N^4$-{[4-(aminomethyl)cyclohexyl]methyl}-5-nitro-$N^2$-[(1S)-1,2,3,4-tetrahydronaphthalen-1-yl]pyrimidine-2,4-diamine $N^4$-{[4-(aminomethyl)cyclohexyl]methyl}-$N^2$-[2-(4-chlorophenyl)ethyl]-5-nitropyrimidine-2,4-diamine $N^4$-{[4-(aminomethyl)cyclohexyl]methyl}-$N^2$-[2-(2-methylphenyl)ethyl]-5-nitropyrimidine-2,4-diamine $N^4$-{[4-(aminomethyl)cyclohexyl]methyl}-$N^2$-[2-(3-methylphenyl)ethyl]-5-nitropyrimidine-2,4-diamine $N^4$-{[4-(aminomethyl)cyclohexyl]methyl}-$N^2$-[2-(4-methylphenyl)ethyl]-5-nitropyrimidine-2,4-diamine $N^4$-{[4-(aminomethyl)cyclohexyl]methyl}-$N^2$-[2-(2-fluorophenyl)ethyl]-5-nitropyrimidine-2,4-diamine $N^4$-{[4-(aminomethyl)cyclohexyl]methyl}-$N^2$-[2-(3-fluorophenyl)ethyl]-5-nitropyrimidine-2,4-diamine $N^4$-{[4-(aminomethyl)cyclohexyl]methyl}-$N^2$-[2-(4-fluorophenyl)ethyl]-5-nitropyrimidine-2,4-diamine $N^2$-(2-aminobenzyl)-$N^4$-{[4-(aminomethyl)cyclohexyl]methyl}-5-nitropyrimidine-2,4-diamine $N^4$-{[4-(aminomethyl)cyclohexyl]methyl}-$N^2$-(3,5-dimethoxybenzyl)-5-nitropyrimidine-2,4-diamine $N^4$-{[4-(aminomethyl)cyclohexyl]methyl}-$N^2$-[3,5-bis(trifluoromethyl)benzyl]-5-nitropyrimidine-2,4-diamine {3-[({2-[(2-chlorobenzyl)amino]-5-nitropyrimidin-4-yl}amino)methyl]phenyl}methane amine 2-({[4-({[4-(aminomethyl)cyclohexyl]methyl}amino)-5-nitropyrimidin-2-yl]amino}methyl)phenol $N^2$-(5-amino-2-chlorobenzyl)-$N^4$-{[4-(aminomethyl)cyclohexyl]methyl}-5-nitropyrimidine-2,4-diamine 4-({[4-(aminomethyl)cyclohexyl]methyl}amino)-2-[(2-chlorobenzyl)amino]pyrimidine-5-carboxamide $N^4$-{[4-(aminomethyl)cyclohexyl]methyl}-$N^2$-(2-chlorobenzyl)-5-fluoropyrimidine-2,4-diamine 3-({[4-({[4-(aminomethyl)cyclohexyl]methyl}amino)-5-nitropyrimidin-2-yl]amino}methyl)-N-[2-(2-methylphenyl)ethyl]benzamide (1S,2R)-2-({[4-({[4-(aminomethyl)cyclohexyl]methyl}amino)-5-nitropyrimidin-2-yl]amino}methyl)cyclohexanol (1R,2R)-2-({[4-({[4-(aminomethyl)cyclohexyl]methyl}amino)-5-nitropyrimidin-2-yl]amino}methyl)cyclohexanol methyl 4-({[4-(aminomethyl)cyclohexyl]methyl}amino)-2-[(2-chlorobenzyl)amino]pyrimidine-5-carboxylate 4-{[4-({[4-(aminomethyl)cyclohexyl]methyl}amino)-5-nitropyrimidin-2-yl]amino}-N-[2-(2-methylphenyl)ethyl]butanamide 5-{[4-({[4-(aminomethyl)cyclohexyl]methyl}amino)-5-nitropyrimidin-2-yl]amino}-N-[2-(2-methylphenyl)ethyl]pentanamide 6-{[4-({[4-(aminomethyl)cyclohexyl]methyl}amino)-5-nitropyrimidin-2-yl]amino}-N-[2-(2-methylphenyl)ethyl]hexanamide (1R,3R)-3-({[4-({[4-(aminomethyl)cyclohexyl]methyl}amino)-5-nitropyrimidin-2-yl]amino}methyl)-4,4-dimethylcyclohexanol $N^4$-({4-cis-[(dimethylamino)methyl]cyclohexyl}methyl)-$N^2$-(1-naphthylmethyl)-5-nitropyrimidine-2,4-diamine $N^2$-[2-(methylthio)benzyl]-5-nitro-N-4-(piperidin-4-ylmethyl)pyrimidine-2,4-diamine 5-nitro-$N^4$-(piperidin-4-ylmethyl)-$N^2$-{2-[(trifluoromethyl)thio]benzyl}pyrimidine-2,4-diamine $N^2$-(1-naphthylmethyl)-5-nitro-$N^4$-(piperidin-4-ylmethyl)pyrimidine-2,4-diamine $N^4$-({4-[(dimethylamino)methyl]cyclohexyl}methyl)-$N^2$-[2-(methylthio)benzyl]-5-nitropyrimidine-2,4-diamine $N^4$-({4-[(dimethylamino)methyl]cyclohexyl}methyl)-5-nitro-$N^2$-{2-[(trifluoromethyl)thio]benzyl}pyrimidine-2,4-diamine $N^4$-({4-[(dimethylamino)methyl]cyclohexyl}methyl)-$N^2$-(1-naphthylmethyl)-5-nitropyrimidine-2,4-diamine $N^4$-{4-[(dimethylamino)methyl]benzyl}-$N^2$-[2-(methylthio)benzyl]-5-nitropyrimidine-2,4-diamine $N^4$-{4-[(dimethylamino)methyl]benzyl}-5-nitro-$N^2$-{2-[(trifluoromethyl)thio]benzyl}pyrimidine-2,4-diamine $N^4$-{4-[(dimethylamino)methyl]benzyl}-$N^{-2}$-(1-naphthylmethyl)-5-nitropyrimidine-2,4-diamine $N^4$-[(1-methylpiperidin-4-yl)methyl]-$N^2$-[2-(methylthio)benzyl]-5-nitropyrimidine-2,4-diamine $N^4$-[(1-methylpiperidin-4-yl)methyl]-5-nitro-$N^2$-{2-[(trifluoromethyl)thio]benzyl}pyrimidine-2,4-diamine $N^4$-[(1-methylpiperidin-4-yl)methyl]-$N^2$-(1-naphthylmethyl)-5-nitropyrimidine-2,4-diamine $N^2$-(2-chlorobenzyl)-$N^4$-[(1-methylpiperidin-4-yl)methyl]-5-nitropyrimidine-2,4-diamine $N^2$-(2-methoxybenzyl)-$N^4$-[(1-methylpiperidin-4-yl)methyl]-5-nitropyrimidine-2,4-diamine $N^4$-{[4-(aminomethyl)cyclohexyl]methyl}-$N^2$-(2-methoxybenzyl)-5-nitropyrimidine-2,4-diamine $N^4$-{[4-(aminomethyl)cyclohexyl]methyl}-5-nitro-$N^2$-[2-(trifluoromethyl)benzyl]pyrimidine-2,4-diamine $N^4$-{[4-(aminomethyl)cyclohexyl]methyl}-$N^2$-(2,4-dichlorobenzyl)-5-nitropyrimidine-2,4-diamine $N^4$-{[4-(aminomethyl)cyclohexyl]methyl}-$N^2$-(3-methoxybenzyl)-5-nitropyrimidine-2,4-diamine $N^4$-{[4-(aminomethyl)cyclohexyl]methyl}-$N^2$-[4-fluoro-2-(trifluoromethyl)benzyl]-5-nitropyrimidine-2,4-diamine $N^4$-{[4-(aminomethyl)cyclohexyl]methyl}-$N^2$-(3-methylbenzyl)-5-nitropyrimidine-2,4-diamine $N^4$-{[4-(aminomethyl)cyclohexyl]methyl}-5-nitro-$N^2$-(pyridin-2-ylmethyl)pyrimidine-2,4-diamine $N^4$-{[4-(aminomethyl)cyclohexyl]methyl}-$N^2$-(3-chlorobenzyl)-5-nitropyrimidine-2,4-diamine $N^4$-{[4-(aminomethyl)cyclohexyl]methyl}-$N^2$-(4-chlorobenzyl)-5-nitropyrimidine-2,4-diamine $N^4$-{[4-(aminomethyl)cyclohexyl]methyl}-$N^2$-(4-bromobenzyl)-5-nitropyrimidine-2,4-diamine $N^4$-{[4-(aminomethyl)cyclohexyl]methyl}-$N^2$-(2,4-dimethoxybenzyl)-5-nitropyrimidine-2,4-diamine $N^4$-{[4-(aminomethyl)cyclohexyl]methyl}-$N^2$-[2-chloro-5-(trifluoromethyl)benzyl]-5-nitropyrimidine-2,4-diamine $N^4$-{[4-(aminomethyl)cyclohexyl]methyl}-$N^2$-(2,5-dichlorobenzyl)-5-nitropyrimidine-2,4-diamine $N^4$-{[4-(aminomethyl)cyclohexyl]methyl}-5-nitro-$N^2$-[2-(trifluoromethoxy)benzyl]pyrimidine-2,4-diamine $N^4$-{[4-(aminomethyl)cyclohexyl]methyl}-N-2-(2-chloro-6-methylbenzyl)-5-nitropyrimidine-2,4-diamine $N^4$-{[4-(aminomethyl)cyclohexyl]methyl}-$N^2$-(2,3-dichlorobenzyl)-5-nitropyrimidine-2,4-diamine
$N^4$-{[4-(aminomethyl)cyclohexyl]methyl}-$N^2$-(2-furylmethyl)-5-nitropyrimidine-2,4-diamine
$N^4$-{[4-(aminomethyl)cyclohexyl]methyl}-5-nitro-$N^2$-(thien-2-ylmethyl)pyrimidine-2,4-diamine
$N^4$-{[4-(aminomethyl)cyclohexyl]methyl}-$N^2$-(2-chlorobenzyl)-5-methylpyrimidine-2,4-diamine
$N^4$-(6-aminohexyl)-$N^2$-(2-chlorobenzyl)-5-nitropyrimidine-2,4-diamine
$N^4$-[4-(aminomethyl)benzyl]-$N^2$-(2-chlorobenzyl)-5-nitropyrimidine-2,4-diamine
$N^4$-(7-aminoheptyl)-$N^2$-(2-chlorobenzyl)-5-nitropyrimidine-2,4-diamine
$N^4$-{[3-(aminomethyl)cyclohexyl]methyl}-$N^2$-(2-chlorobenzyl)-5-nitropyrimidine-2,4-diamine
$N^4$-{[4-(aminomethyl)cyclohexyl]methyl}-$N$-$^2$-(1-methyl-1-phenylethyl)-5-nitropyrimidine-2,4-diamine
4-(4,4'-bipiperidin-1-yl)-$N$-(2-chlorobenzyl)-5-nitropyrimidin-2-amine
$N^2$-(2-chlorobenzyl)-$N$-$^4$-({4-[(dimethylamino)methyl]cyclohexyl}methyl)-5-nitropyrimidine-2,4-diamine
$N^4$-{[4-(aminomethyl)cyclohexyl]methyl}-$N^2$-(2,5-difluorobenzyl)-5-nitropyrimidine-2,4-diamine
$N^4$-{[4-(aminomethyl)cyclohexyl]methyl}-$N^2$-[4-(difluoromethoxy)benzyl]-5-nitropyrimidine-2,4-diamine
$N^4$-{[4-(aminomethyl)cyclohexyl]methyl}-$N^2$-(2-ethoxybenzyl)-5-nitropyrimidine-2,4-diamine
$N^4$-{[4-(aminomethyl)cyclohexyl]methyl}-5-nitro-$N$-2-[(1S)-1-phenylethyl]pyrimidine-2,4-diamine
$N^4$-{[4-(aminomethyl)cyclohexyl]methyl}-$N^2$-(2-methylbenzyl)-5-nitropyrimidine-2,4-diamine
$N^4$-{[4-(aminomethyl)cyclohexyl]methyl}-$N^2$-(2-fluorobenzyl)-5-nitropyrimidine-2,4-diamine
$N^4$-{[4-(aminomethyl)cyclohexyl]methyl}-$N^2$-(3-chloro-2-fluorobenzyl)-5-nitropyrimidine-2,4-diamine
$N^4$-{[4-(aminomethyl)cyclohexyl]methyl}-5-nitro-$N^2$-(4-pentylbenzyl)pyrimidine-2,4-diamine
$N^4$-{[4-(aminomethyl)cyclohexyl]methyl}-$N^2$-(4-butoxybenzyl)-5-nitropyrimidine-2,4-diamine
$N^4$-{[4-(aminomethyl)cyclohexyl]methyl}-$N^2$-(2,3-dimethoxybenzyl)-5-nitropyrimidine-2,4-diamine
$N^4$-{[4-(aminomethyl)cyclohexyl]methyl}-$N^2$-(2,5-dimethoxybenzyl)-5-nitropyrimidine-2,4-diamine
$N^2$-(2-chlorobenzyl)-$N$-$^4$-[7-(dimethylamino)heptyl]-5-nitropyrimidine-2,4-diamine
$N^4$-{[4-(aminomethyl)cyclohexyl]methyl}-$N^2$-(1,1'-biphenyl-2-ylmethyl)-5-nitropyrimidine-2,4-diamine
$N^4$-{[4-(aminomethyl)cyclohexyl]methyl}-$N^2$-(4-fluorobenzyl)-5-nitropyrimidine-2,4-diamine
$N^4$-{[4-(aminomethyl)cyclohexyl]methyl}-$N^2$-(2,4-difluorobenzyl)-5-nitropyrimidine-2,4-diamine
$N^4$-{[4-(aminomethyl)cyclohexyl]methyl}-$N^2$-(3-fluoro-4-methylbenzyl)-5-nitropyrimidine-2,4-diamine
$N^4$-{[4-(aminomethyl)cyclohexyl]methyl}-$N^2$-(2,3-difluorobenzyl)-5-nitropyrimidine-2,4-diamine
$N^4$-{[4-(aminomethyl)cyclohexyl]methyl}-5-bromo-$N^2$-(2-chlorobenzyl)pyrimidine-2,4-diamine
$N^4$-{[4-(aminomethyl)cyclohexyl]methyl}-$N^2$-(2,6-dimethoxybenzyl)-5-nitropyrimidine-2,4-diamine
$N^4$-{[4-(aminomethyl)cyclohexyl]methyl}-$N^2$-(2,6-difluorobenzyl)-5-nitropyrimidine-2,4-diamine
$N^4$-{[4-(aminomethyl)cyclohexyl]methyl}-$N^2$-[2-fluoro-3-(trifluoromethyl)benzyl]-5-nitropyrimidine-2,4-diamine
$N^4$-{[4-(aminomethyl)cyclohexyl]methyl}-$N^2$-(4-chloro-2-fluorobenzyl)-5-nitropyrimidine-2,4-diamine
$N^4$-{[4-(aminomethyl)cyclohexyl]methyl}-5-nitro-$N^2$-(1-phenylcyclopropyl)pyrimidine-2,4-diamine
$N^4$-{[4-(aminomethyl)cyclohexyl]methyl}-$N^2$-[1-(2-chlorophenyl)-1-methylethyl]-5-nitropyrimidine-2,4-diamine
$N^4$-{[4-(aminomethyl)cyclohexyl]methyl}-$N^2$-(2,3-dihydro-1-benzofuran-5-ylmethyl)-5-nitropyrimidine-2,4-diamine
$N^4$-{[4-(aminomethyl)cyclohexyl]methyl}-$N^2$-[(1,5-dimethyl-1H-pyrrol-2-yl)methyl]-5-nitropyrimidine-2,4-diamine
$N^4$-{[4-(aminomethyl)cyclohexyl]methyl}-$N^2$-(2-bromobenzyl)-5-nitropyrimidine-2,4-diamine
$N^4$-{[4-(aminomethyl)cyclohexyl]methyl}-$N^2$-(2,3-dimethylbenzyl)-5-nitropyrimidine-2,4-diamine
$N^4$-{[4-(aminomethyl)cyclohexyl]methyl}-$N^2$-(2,4-dimethylbenzyl)-5-nitropyrimidine-2,4-diamine
$N^4$-{[4-(aminomethyl)cyclohexyl]methyl}-$N^2$-(2,5-dimethylbenzyl)-5-nitropyrimidine-2,4-diamine
$N^4$-{[4-(aminomethyl)cyclohexyl]methyl}-$N^2$-[2-fluoro-5-(trifluoromethyl)benzyl]-5-nitropyrimidine-2,4-diamine
$N^4$-{[4-(aminomethyl)cyclohexyl]methyl}-$N^2$-[2-(methylthio)benzyl]-5-nitropyrimidine-2,4-diamine
$N^4$-{[4-(aminomethyl)cyclohexyl]methyl}-5-nitro-$N^2$-{2-[(trifluoromethyl)thio]benzyl}pyrimidine-2,4-diamine
$^4$-{[4-(aminomethyl)cyclohexyl]methyl}-$N^2$-(3-fluorobenzyl)-5-nitropyrimidine-2,4-diamine
$N^4$-{[4-(aminomethyl)cyclohexyl]methyl}-$N^2$-(6-chloro-2-fluoro-3-methylbenzyl)-5-nitropyrimidine-2,4-diamine
$N^4$-{[4-(aminomethyl)cyclohexyl]methyl}-$N^2$-(2-chloro-6-fluoro-3-methylbenzyl)-5-nitropyrimidine-2,4-diamine
$N^4$-{[4-(aminomethyl)cyclohexyl]methyl}-$N$-2-2-naphthyl-5-nitropyrimidine-2,4-diamine
$N^4$-{[4-(aminomethyl)cyclohexyl]methyl}-$N$-2-(2-naphthylmethyl)-5-nitropyrimidine-2,4-diamine
$N^4$-{[4-(aminomethyl)cyclohexyl]methyl}-$N^2$-[2-fluoro-4-(trifluoromethyl)benzyl]-5-nitropyrimidine-2,4-diamine
$N^4$-{[4-(aminomethyl)cyclohexyl]methyl}-$N^2$-(4-chloro-2-methylbenzyl)-5-nitropyrimidine-2,4-diamine
$N^4$-{[4-(aminomethyl)cyclohexyl]methyl}-$N^2$-(5-chloro-2-methylbenzyl)-5-nitropyrimidine-2,4-diamine
$N^4$-{[4-(aminomethyl)cyclohexyl]methyl}-$N^2$-(3-chloro-2-methylbenzyl)-5-nitropyrimidine-2,4-diamine
$N^4$-{[4-(aminomethyl)cyclohexyl]methyl}-$N^2$-[5-fluoro-2-(trifluoromethyl)benzyl]-5-nitropyrimidine-2,4-diamine
$N^4$-{[4-(aminomethyl)cyclohexyl]methyl}-$N^2$-(5-chloro-2-fluorobenzyl)-5-nitropyrimidine-2,4-diamine
$N^4$-{[4-(aminomethyl)cyclohexyl]methyl}-$N^2$-(2,3-difluoro-4-methylbenzyl)-5-nitropyrimidine-2,4-diamine
$N^4$-{[4-(aminomethyl)cyclohexyl]methyl}-$N^2$-(5-fluoro-2-methylbenzyl)-5-nitropyrimidine-2,4-diamine
$N^4$-{[4-(aminomethyl)cyclohexyl]methyl}-$N^2$-1-naphthyl-5-nitropyrimidine-2,4-diamine
{4-trans-[({2-[(2-chlorobenzyl)amino]-5-nitropyrimidin-4-yl}amino)methyl]cyclohexyl}methanol
$N^4$-{[4-(aminomethyl)cyclohexyl]methyl}-5-bromo-$N^2$-(2,5-dichlorobenzyl)pyrimidine-2,4-diamine
$N^4$-{[4-(aminomethyl)cyclohexyl]methyl}-5-bromo-$N^2$-(2,4-dichlorobenzyl)pyrimidine-2,4-diamine
$N^4$-{[4-(aminomethyl)cyclohexyl]methyl}-5-bromo-$N$-2-(2-bromobenzyl)pyrimidine-2,4-diamine N⁴-{[4-(aminomethyl)cyclohexyl]methyl}-N²-(cyclohexylmethyl)-5-nitropyrimidine-2,4-diamine
N⁴-{[4-(aminomethyl)cyclohexyl]methyl}-N²-(2-naphthylmethyl)-5-nitropyrimidine-2,4-diamine
N⁴-{[4-(aminomethyl)cyclohexyl]methyl}-5-bromo-N²-[2-(trifluoromethoxy)benzyl]pyrimidine-2,4-diamine
N⁴-{[4-(aminomethyl)cyclohexyl]methyl}-5-bromo-N²-[2-(trifluoromethyl)benzyl]pyrimidine-2,4-diamine
N⁴-{[4-(aminomethyl)cyclohexyl]methyl}-N²-[2-(difluoromethoxy)benzyl]-5-nitropyrimidine-2,4-diamine
N⁴-{[4-(aminomethyl)cyclohexyl]methyl}-N²-[3-(difluoromethoxy)benzyl]-5-nitropyrimidine-2,4-diamine
N⁴-{[4-(aminomethyl)cyclohexyl]methyl}-N²-(2-chloro-4-fluorobenzyl)-5-nitropyrimidine-2,4-diamine
N⁴-{[4-(aminomethyl)cyclohexyl]methyl}-N²-(2-chloro-3,6-difluorobenzyl)-5-nitropyrimidine-2,4-diamine
N⁴-{[4-(aminomethyl)cyclohexyl]methyl}-5-nitro-N-2-(2,3,5-trifluorobenzyl)pyrimidine-2,4-diamine
N⁴-{[4-(aminomethyl)cyclohexyl]methyl}-5-nitro-N²-(2,3,4,5-tetrafluorobenzyl)pyrimidine-2,4-diamine
N⁴-{[4-(aminomethyl)cyclohexyl]methyl}-5-nitro-N²-[(1R)-1-phenylethyl]pyrimidine-2,4-diamine
N⁴-{[4-(aminomethyl)cyclohexyl]methyl}-N²-2,3-dihydro-1H-inden-2-yl-5-nitropyrimidine-2,4-diamine
N⁴-{[4-(aminomethyl)cyclohexyl]methyl}-N²-[(1S)-2,3-dihydro-1H-inden-1-yl]-5-nitropyrimidine-2,4-diamine
N⁴-{[4-(aminomethyl)cyclohexyl]methyl}-N²-[(1R)-2,3-dihydro-1H-inden-1-yl]-5-nitropyrimidine-2,4-diamine
N⁴-{[4-(aminomethyl)cyclohexyl]methyl}-N²-(4-chloro-1-naphthyl)-5-nitropyrimidine-2,4-diamine
N⁴-{[4-(aminomethyl)cyclohexyl]methyl}-N²-(4-methoxy-2-naphthyl)-5-nitropyrimidine-2,4-diamine
N⁴-{[4-(aminomethyl)cyclohexyl]methyl}-5-nitro-N²-quinolin-6-ylpyrimidine-2,4-diamine
N⁴-{[4-trans-(aminomethyl)cyclohexyl]methyl}-N²-(2,5-dichlorobenzyl)-5-nitropyrimidine-2,4-diamine
N⁴-{[4-trans-(aminomethyl)cyclohexyl]methyl}-N²-(2,3-dichlorobenzyl)-5-nitropyrimidine-2,4-diamine
N⁴-{[4-(aminomethyl)cyclohexyl]methyl}-N²-[2-(2-chlorophenyl)ethyl]-5-nitropyrimidine-2,4-diamine
N⁴-{[4-(aminomethyl)cyclohexyl]methyl}-N²-[2-(3-chlorophenyl)ethyl]-5-nitropyrimidine-2,4-diamine
N⁴-{[4-(aminomethyl)cyclohexyl]methyl}-N²-(2-chloro-6-phenoxybenzyl)-5-nitropyrimidine-2,4-diamine
N⁴-{[4-(aminomethyl)cyclohexyl]methyl}-5-bromo-N-²-2-naphthylpyrimidine-2,4-diamine
N⁴-{[4-(aminomethyl)cyclohexyl]methyl}-5-bromo-N-²-(1-naphthylmethyl)pyrimidine-2,4-diamine
N⁴-{[4-(aminomethyl)cyclohexyl]methyl}-5-nitro-N²-(pyridin-3-ylmethyl)pyrimidine-2,4-diamine
4-({[4-(aminomethyl)cyclohexyl]methyl}amino)-2-[(2-chlorobenzyl)amino]pyrimidine-5-carbonitrile
N⁴-{[4-(aminomethyl)cyclohexyl]methyl}-N²-[4-(dimethylamino)benzyl]-5-nitropyrimidine-2,4-diamine
N⁴-{[4-trans-(aminomethyl)cyclohexyl]methyl}-N-²-(2-bromobenzyl)-5-nitropyrimidine-2,4-diamine
N⁴-(7-aminoheptyl)-N²-(2-bromobenzyl)-5-nitropyrimidine-2,4-diamine
N⁴-(7-aminoheptyl)-N²-(2,5-dichlorobenzyl)-5-nitropyrimidine-2,4-diamine
N-({4-[({2-[(2-chlorobenzyl)amino]-5-nitropyrimidin-4-yl}amino)methyl]cyclohexyl}methyl)guanidine
N²-(3-aminobenzyl)-N-⁴-{[4-(aminomethyl)cyclohexyl]methyl}-5-nitropyrimidine-2,4-diamine
N⁴-{[4-(aminomethyl)cyclohexyl]methyl}-5-nitro-N²-(2-nitrobenzyl)pyrimidine-2,4-diamine
N⁴-{[4-(aminomethyl)cyclohexyl]methyl}-N²-[2-(2-bromophenyl)ethyl]-5-nitropyrimidine-2,4-diamine
N⁴-{[4-(aminomethyl)cyclohexyl]methyl}-N²-(2-bromobenzyl)-5-chloropyrimidine-2,4-diamine
(4-{[(2-{[2-(1H-indol-3-yl)ethyl]amino}-5-nitropyrimidin-4-yl)amino]methyl}cyclohexyl) methanaminium chloride
N-({3-[({2-[(2-chlorobenzyl)amino]-5-nitropyrimidin-4-yl}amino)methyl]cyclohexyl}methyl)guanidine
3-({[4-({[4-(aminomethyl)cyclohexyl]methyl}amino)-5-nitropyrimidin-2-yl]amino}methyl)phenyl
(4-{[(2-{[2-(1H-imidazol-4-yl)ethyl]amino}-5-nitropyrimidin-4-yl)amino]methyl}cyclohexyl) methanaminium chloride
N²-(2-chlorobenzyl)-N⁴-({4-cis-[(dimethylamino)methyl]cyclohexyl}methyl)-5-nitropyrimidine-2,4-diamine
N⁴-{[4-(aminomethyl)cyclohexyl]methyl}-5-chloro-N-²-(2-chlorobenzyl)pyrimidine-2,4-diamine
N²-(2-chlorobenzyl)-5-nitro-N⁴-(piperidin-4-ylmethyl)pyrimidine-2,4-diamine
N⁴-{[4-(aminomethyl)cyclohexyl]methyl}-5-nitro-N²-(2-phenylethyl)pyrimidine-2,4-diamine
N⁴-{[4-(aminomethyl)cyclohexyl]methyl}-5-nitro-N²-(3-phenylpropyl)pyrimidine-2,4-diamine
N⁴-{[4-(aminomethyl)cyclohexyl]methyl}-5-nitro-N²-(4-phenylbutyl)pyrimidine-2,4-diamine
N⁴-{[4-(aminomethyl)cyclohexyl]methyl}-5-nitro-N²-(2-phenylpropyl)pyrimidine-2,4-diamine
N⁴-{[4-(aminomethyl)cyclohexyl]methyl}-N²-[2-(4-methoxyphenyl)ethyl]-5-nitropyrimidine-2,4-diamine
N⁴-{[4-(aminomethyl)cyclohexyl]methyl}-N²-[2-(3-methoxyphenyl)ethyl]-5-nitropyrimidine-2,4-diamine
N⁴-{[4-(aminomethyl)cyclohexyl]methyl}-N²-[2-(2-methoxyphenyl)ethyl]-5-nitropyrimidine-2,4-diamine
4-[({2-[(2-chlorobenzyl)amino]-5-nitropyrimidin-4-yl}amino)methyl]piperidine-1-carboximidamide
N⁴-{[4-(aminomethyl)cyclohexyl]methyl}-N²-(3,5-dichlorobenzyl)-5-nitropyrimidine-2,4-diamine
N4-(5-aminopentyl)-N-2-(2-chlorobenzyl)-5-nitropyrimidine-2,4-diamine
2-(4-chlorobenzylamino)-4-(1,4,6,7-tetrahydro-imidazo[4,5-c]pyridin-5-yl)-5-nitro-pyrimidine
2-(2-chlorobenzylamino)-4-(1,4,6,7-tetrahydro-imidazo[4,5-c]pyridin-5-yl)-5-nitro-pyrimidine
2-(benzylamino)-4-(1,4,6,7-tetrahydro-imidazo[4,5-c]pyridin-5-yl)-5-nitro-pyrimidine or a tautomer, or pharmaceutically acceptable salt thereof; or a corresponding compound having at least one amine group protected by an amino-protecting group.

6. A compound according to claim 1, selected from:
N⁴-{[4-(aminomethyl)cyclohexyl]methyl}-5-nitro-N²-[(2R)-1,2,3,4-tetrahydronaphthalen-2-yl]pyrimidine-2,4-diamine
N⁴-{[4-(aminomethyl)cyclohexyl]methyl}-N²-[2-(4-chlorophenyl)ethyl]-5-nitropyrimidine-2,4-diamine
N⁴-{[4-(aminomethyl)cyclohexyl]methyl}-N²-[2-(3-methylphenyl)ethyl]-5-nitropyrimidine-2,4-diamine
N⁴-{[4-(aminomethyl)cyclohexyl]methyl}-N²-[2-(4-methylphenyl)ethyl]-5-nitropyrimidine-2,4-diamine
N⁴-{[4-(aminomethyl)cyclohexyl]methyl}-N²-[2-(3-fluorophenyl)ethyl]-5-nitropyrimidine-2,4-diamine
N⁴-{[4-(aminomethyl)cyclohexyl]methyl}-N²-[2-(4-fluorophenyl)ethyl]-5-nitropyrimidine-2,4-diamine (1R,3R)-3-({[4-({[4-(aminomethyl)cyclohexyl]methyl}amino)-5-nitropyrimidin-2-yl]amino}methyl)-4,4-dimethylcyclohexanol $N^4$-({4-cis-[(dimethylamino)methyl]cyclohexyl}methyl)-$N^2$-(1-naphthylmethyl)-5-nitropyrimidine-2,4-diamine $N^2$-[2-(methylthio)benzyl]-5-nitro-$N^4$-(piperidin-4-ylmethyl)pyrimidine-2,4-diamine 5-nitro-$N^4$-(piperidin-4-ylmethyl)-$N^2$-{2-[(trifluoromethyl)thio]benzyl}pyrimidine-2,4-diamine $N^2$-(1-naphthylmethyl)-5-nitro-$N^4$-(piperidin-4-ylmethyl)pyrimidine-2,4-diamine $N^4$-({4-[(dimethylamino)methyl]cyclohexyl}methyl)-$N^2$-[2-(methylthio)benzyl]-5-nitropyrimidine-2,4-diamine $N^4$-({4-[(dimethylamino)methyl]cyclohexyl}methyl)-5-nitro-$N^2$-{2-[(trifluoromethyl)thio]benzyl}pyrimidine-2,4-diamine $N^4$-({4-[(dimethylamino)methyl]cyclohexyl}methyl)-$N^2$-(1-naphthylmethyl)-5-nitropyrimidine-2,4-diamine $N^4$-{4-[(dimethylamino)methyl]benzyl}-$N^2$-[2-(methylthio)benzyl]-5-nitropyrimidine-2,4-diamine $N^4$-{4-[(dimethylamino)methyl]benzyl}-5-nitro-$N^2$-{2-[(trifluoromethyl)thio]benzyl}pyrimidine-2,4-diamine $N^4$-[(1-methylpiperidin-4-yl)methyl]-$N^2$-[2-(methylthio)benzyl]-5-nitropyrimidine-2,4-diamine $N^4$-[(1-methylpiperidin-4-yl)methyl]-5-nitro-$N^2$-{2-[(trifluoromethyl)thio]benzyl}pyrimidine-2,4-diamine $N^4$-{[4-(aminomethyl)cyclohexyl]methyl}-$N^2$-(2-methoxybenzyl)-5-nitropyrimidine-2,4-diamine $N^4$-{[4-(aminomethyl)cyclohexyl]methyl}-5-nitro-$N^2$-[2-(trifluoromethyl)benzyl]pyrimidine-2,4-diamine $N^4$-{[4-(aminomethyl)cyclohexyl]methyl}-$N^2$-(2,4-dichlorobenzyl)-5-nitropyrimidine-2,4-diamine $N^4$-{[4-(aminomethyl)cyclohexyl]methyl}-$N^2$-[4-fluoro-2-(trifluoromethyl)benzyl]-5-nitropyrimidine-2,4-diamine $N^4$-{[4-(aminomethyl)cyclohexyl]methyl}-$N^2$-(3-methylbenzyl)-5-nitropyrimidine-2,4-diamine $N^4$-{[4-(aminomethyl)cyclohexyl]methyl}-$N^2$-(3-chlorobenzyl)-5-nitropyrimidine-2,4-diamine $N^4$-{[4-(aminomethyl)cyclohexyl]methyl}-$N^2$-(4-bromobenzyl)-5-nitropyrimidine-2,4-diamine $N^4$-{[4-(aminomethyl)cyclohexyl]methyl}-$N^2$-[2-chloro-5-(trifluoromethyl)benzyl]-5-nitropyrimidine-2,4-diamine $N^4$-{[4-(aminomethyl)cyclohexyl]methyl}-$N^2$-(2,5-dichlorobenzyl)-5-nitropyrimidine-2,4-diamine $N^4$-{[4-(aminomethyl)cyclohexyl]methyl}-5-nitro-$N^2$-[2-(trifluoromethoxy)benzyl]pyrimidine-2,4-diamine $N^4$-{[4-(aminomethyl)cyclohexyl]methyl}-$N^2$-(2-chloro-6-methylbenzyl)-5-nitropyrimidine-2,4-diamine $N^4$-{[4-(aminomethyl)cyclohexyl]methyl}-$N^2$-(2,3-dichlorobenzyl)-5-nitropyrimidine-2,4-diamine $N^4$-{[3-(aminomethyl)cyclohexyl]methyl}-$N^2$-(2-chlorobenzyl)-5-nitropyrimidine-2,4-diamine $N^2$-(2-chlorobenzyl)-$N^4$-({4-[(dimethylamino)methyl]cyclohexyl}methyl)-5-nitropyrimidine-2,4-diamine $N^4$-{[4-(aminomethyl)cyclohexyl]methyl}-$N$-$^2$-(2,5-difluorobenzyl)-5-nitropyrimidine-2,4-diamine $N^4$-{[4-(aminomethyl)cyclohexyl]methyl}-$N^2$-(2-ethoxybenzyl)-5-nitropyrimidine-2,4-diamine $N^4$-{[4-(aminomethyl)cyclohexyl]methyl}-$N^2$-(2-methylbenzyl)-5-nitropyrimidine-2,4-diamine $N^4$-{[4-(aminomethyl)cyclohexyl]methyl}-$N^2$-(2-fluorobenzyl)-5-nitropyrimidine-2,4-diamine $N^4$-{[4-(aminomethyl)cyclohexyl]methyl}-$N^2$-(3-chloro-2-fluorobenzyl)-5-nitropyrimidine-2,4-diamine $N^4$-{[4-(aminomethyl)cyclohexyl]methyl}-$N^2$-(1,1'-biphenyl-2-ylmethyl)-5-nitropyrimidine-2,4-diamine $N^4$-{[4-(aminomethyl)cyclohexyl]methyl}-$N^2$-(2,4-difluorobenzyl)-5-nitropyrimidine-2,4-diamine $N^4$-{[4-(aminomethyl)cyclohexyl]methyl}-$N^2$-(2,3-difluorobenzyl)-5-nitropyrimidine-2,4-diamine $N^4$-{[4-(aminomethyl)cyclohexyl]methyl}-$N^2$-(2,6-difluorobenzyl)-5-nitropyrimidine-2,4-diamine $N^4$-{[4-(aminomethyl)cyclohexyl]methyl}-$N^2$-[2-fluoro-3-(trifluoromethyl)benzyl]-5-nitropyrimidine-2,4-diamine $N^4$-{[4-(aminomethyl)cyclohexyl]methyl}-$N^2$-(4-chloro-2-fluorobenzyl)-5-nitropyrimidine-2,4-diamine $N^4$-{[4-(aminomethyl)cyclohexyl]methyl}-$N^2$-(2-bromobenzyl)-5-nitropyrimidine-2,4-diamine $N^4$-{[4-(aminomethyl)cyclohexyl]methyl}-$N^2$-(2,3-dimethylbenzyl)-5-nitropyrimidine-2,4-diamine $N^4$-{[4-(aminomethyl)cyclohexyl]methyl}-$N^2$-[2-(methylthio)benzyl]-5-nitropyrimidine-2,4-diamine $N^4$-{[4-(aminomethyl)cyclohexyl]methyl}-5-nitro-$N^2$-{2-[(trifluoromethyl)thio]benzyl}pyrimidine-2,4-diamine $N^4$-{[4-(aminomethyl)cyclohexyl]methyl}-$N^2$-(3-fluorobenzyl)-5-nitropyrimidine-2,4-diamine $N^4$-{[4-(aminomethyl)cyclohexyl]methyl}-$N^2$-(6-chloro-2-fluoro-3-methylbenzyl)-5-nitropyrimidine-2,4-diamine $N^4$-{[4-(aminomethyl)cyclohexyl]methyl}-$N^2$-(2-chloro-6-fluoro-3-methylbenzyl)-5-nitropyrimidine-2,4-diamine $N^4$-{[4-(aminomethyl)cyclohexyl]methyl}-$N^2$-2-naphthyl-5-nitropyrimidine-2,4-diamine $N^4$-{[4-(aminomethyl)cyclohexyl]methyl}-$N^2$-(1-naphthylmethyl)-5-nitropyrimidine-2,4-diamine $N^4$-{[4-(aminomethyl)cyclohexyl]methyl}-$N^2$-(4-chloro-2-methylbenzyl)-5-nitropyrimidine-2,4-diamine $N^4$-{[4-(aminomethyl)cyclohexyl]methyl}-$N^2$-(5-chloro-2-methylbenzyl)-5-nitropyrimidine-2,4-diamine $N^4$-{[4-(aminomethyl)cyclohexyl]methyl}-$N^2$-(3-chloro-2-methylbenzyl)-5-nitropyrimidine-2,4-diamine $N^4$-{[4-(aminomethyl)cyclohexyl]methyl}-$N^2$-[5-fluoro-2-(trifluoromethyl)benzyl]-5-nitropyrimidine-2,4-diamine $N^4$-{[4-(aminomethyl)cyclohexyl]methyl}-$N^2$-(5-chloro-2-fluorobenzyl)-5-nitropyrimidine-2,4-diamine $N^4$-{[4-(aminomethyl)cyclohexyl]methyl}-$N^2$-(2,3-difluoro-4-methylbenzyl)-5-nitropyrimidine-2,4-diamine $N^4$-{[4-(aminomethyl)cyclohexyl]methyl}-$N^2$-(5-fluoro-2-methylbenzyl)-5-nitropyrimidine-2,4-diamine $N^4$-{[4-(aminomethyl)cyclohexyl]methyl}-5-bromo-$N^2$-(2,5-dichlorobenzyl)pyrimidine-2,4-diamine $N^4$-{[4-(aminomethyl)cyclohexyl]methyl}-5-bromo-$N^2$-(2-bromobenzyl) pyrimidine-2,4-diamine $N^4$-{[4-(aminomethyl)cyclohexyl]methyl}-$N^2$-(cyclohexylmethyl)-5-nitropyrimidine-2,4-diamine $N^4$-{[4-(aminomethyl)cyclohexyl]methyl}-5-bromo-$N^2$-[2-(trifluoromethyl)benzyl]pyrimidine-2,4-diamine $N^4$-{[4-(aminomethyl)cyclohexyl]methyl}-$N^2$-[(difluoromethoxy)benzyl]-5-nitropyrimidine-2,4-diamine $N^4$-{[4-(aminomethyl)cyclohexyl]methyl}-$N^2$-(2-chloro-4-fluorobenzyl)-5-nitropyrimidine-2,4-diamine $N^4$-{[4-(aminomethyl)cyclohexyl]methyl}-$N^2$-(2-chloro-3,6-difluorobenzyl)-5-nitropyrimidine-2,4-diamine $N^4$-{[4-(aminomethyl)cyclohexyl]methyl}-5-nitro-$N^2$-(2,3,5-trifluorobenzyl)pyrimidine-2,4-diamine $N^4$-{[4-(aminomethyl)cyclohexyl]methyl}-$N^2$-2,3-dihydro-1H-inden-2-yl-5-nitropyrimidine-2,4-diamine $N^4$-{[4-(aminomethyl)cyclohexyl]methyl}-$N^2$-(4-chloro-1-naphthyl)-5-nitropyrimidine-2,4-diamine
$N^4$-{[4-(aminomethyl)cyclohexyl]methyl}-$N^2$-(4-methoxy-2-naphthyl)-5-nitropyrimidine-2,4-diamine
$N^4$-{[4-(aminomethyl)cyclohexyl]methyl}-5-nitro-$N^2$-quinolin-6-ylpyrimidine-2,4-diamine
$N^4$-{[4-trans-(aminomethyl)cyclohexyl]methyl}-$N^2$-(2,3-dichlorobenzyl)-5-nitropyrimidine-2,4-diamine
$N^4$-{[4-(aminomethyl)cyclohexyl]methyl}-$N^2$-[2-(2-chlorophenyl)ethyl]-5-nitropyrimidine-2,4-diamine
$N^4$-{[4-(aminomethyl)cyclohexyl]methyl}-$N^2$-[2-(3-chlorophenyl)ethyl]-5-nitropyrimidine-2,4-diamine
$N^4$-{[4-(aminomethyl)cyclohexyl]methyl}-5-bromo-$N^2$-2-naphthylpyrimidine-2,4-diamine
4-({[4-(aminomethyl)cyclohexyl]methyl}amino)-2-[(2-chlorobenzyl)amino]pyrimidine-5-carbonitrile
N{4-{[4-trans-(aminomethyl)cyclohexyl]methyl}-$N^2$-(2-bromobenzyl)-5-nitropyrimidine-2,4-diamine
$N^4$-(7-aminoheptyl)-$N^2$-(2-bromobenzyl)-5-nitropyrimidine-2,4-diamine
$N^4$-(7-aminoheptyl)-$N^2$-(2,5-dichlorobenzyl)-5-nitropyrimidine-2,4-diamine
$N^4$-({4-[({2-[(2-chlorobenzyl)amino]-5-nitropyrimidin-4-yl}amino)methyl]cyclohexyl}methyl)guanidine
$N^4$-{[4-(aminomethyl)cyclohexyl]methyl}-5-nitro-$N^2$-(2-nitrobenzyl)pyrimidine-2,4-diamine
$N^4$-{[4-(aminomethyl)cyclohexyl]methyl}-$N^2$-[2-(2-bromophenyl)ethyl]-5-nitropyrimidine-2,4-diamine
$N^4$-{[4-(aminomethyl)cyclohexyl]methyl}-$N^2$-(2-bromobenzyl)-5-chloropyrimidine-2,4-diamine
N-({3-[({2-[(2-chlorobenzyl)amino]-5-nitropyrimidin-4-yl}amino)methyl]cyclohexyl}methyl)guanidine
3-({[4-({[4-(aminomethyl)cyclohexyl]methyl}amino)-5-nitropyrimidin-2-yl]amino}methyl)phenol
$N^2$-(2-chlorobenzyl)-$N^4$-({4-cis-[(dimethylamino)methyl]cyclohexyl}methyl)-5-nitropyrimidine-2,4-diamine
$N^2$-(2-chlorobenzyl)-5-nitro-$N^4$-(piperidin-4-ylmethyl)pyrimidine-2,4-diamine
$N^4$-{[4-(aminomethyl)cyclohexyl]methyl}-5-nitro-$N^2$-(2-phenylethyl)pyrimidine-2,4-diamine
$N^4$-{[4-(aminomethyl)cyclohexyl]methyl}-5-nitro-$N^2$-(4-phenylbutyl)pyrimidine-2,4-diamine or a tautomer, or pharmaceutically acceptable salt thereof; or a corresponding compound having at least one amine group protected by an amino-protecting group.

7. A compound according to claim 1, selected from:
$N^4$-({4-[(dimethylamino)methyl]cyclohexyl}methyl)-$N^2$-(1-naphthylmethyl)-5-nitropyrimidine-2,4-diamine
$N^2$-[2-(methylthio)benzyl]-5-nitro-$N^4$-(piperidin-4-ylmethyl)pyrimidine-2,4-diamine
5-nitro-$N^4$-(piperidin-4-ylmethyl)-$N^2$-{2-[(trifluoromethyl)thio]benzyl}pyrimidine-2,4-diamine
$N^2$-(1-naphthylmethyl)-5-nitro-$N^4$-(piperidin-4-ylmethyl)pyrimidine-2,4-diamine
$N^4$-({4-[(dimethylamino)methyl]cyclohexyl}methyl)-$N^2$-[2-(methylthio)benzyl]-5-nitropyrimidine-2,4-diamine
$N^4$-({4-[(dimethylamino)methyl]cyclohexyl}methyl)-5-nitro-$N^2$-{2-[(trifluoromethyl)thio]benzyl}pyrimidine-2,4-diamine
$N^4$-({4-[(dimethylamino)methyl]cyclohexyl}methyl)-$N^2$-(1-naphthylmethyl)-5-nitropyrimidine-2,4-diamine
$N^4$-{4-[(dimethylamino)methyl]benzyl}-$N^2$-[2-(methylthio)benzyl]-5-nitropyrimidine-2,4-diamine
$N^4$-{4-[(dimethylamino)methyl]benzyl}-5-nitro-$N^2$-{2-[(trifluoromethyl)thio]benzyl}pyrimidine-2,4-diamine
$N^4$-[(1-methylpiperidin-4-yl)methyl]-$N^2$-[2-(methylthio)benzyl]-5-nitropyrimidine-2,4-diamine
$N^4$-[(1-methylpiperidin-4-yl)methyl]-5-nitro-$N^2$-{2-[(trifluoromethyl)thio]benzyl}pyrimidine-2,4-diamine
$N^4$-{[4-(aminomethyl)cyclohexyl]methyl}-$N^2$-(2-methoxybenzyl)-5-nitropyrimidine-2,4-diamine
$N^4$-{[4-(aminomethyl)cyclohexyl]methyl}-5-nitro-$N^2$-[2-(trifluoromethoxy)benzyl]pyrimidine-2,4-diamine
$N^4$-{[4-(aminomethyl)cyclohexyl]methyl}-$N^2$-(2,3-dichlorobenzyl)-5-nitropyrimidine-2,4-diamine
$N^4$-{[3-(aminomethyl)cyclohexyl]methyl}-$N^2$-(2-chlorobenzyl)-5-nitropyrimidine-2,4-diamine
$N^2$-(2-chlorobenzyl)-$N^4$-({4-[(dimethylamino)methyl]cyclohexyl}methyl)-5-nitropyrimidine-2,4-diamine
$N^4$-{[4-(aminomethyl)cyclohexyl]methyl}-$N^2$-(2-bromobenzyl)-5-nitropyrimidine-2,4-diamine
$N^4$-{[4-(aminomethyl)cyclohexyl]methyl}-$N^2$-[2-(methylthio)benzyl]-5-nitropyrimidine-2,4-diamine
$N^4$-{[4-(aminomethyl)cyclohexyl]methyl}-5-nitro-$N^2$-{2-[(trifluoromethyl)thio]benzyl}pyrimidine-2,4-diamine
$N^4$-{[4-(aminomethyl)cyclohexyl]methyl}-$N^2$-(1-naphthylmethyl)-5-nitropyrimidine-2,4-diamine
$N^4$-{[4-(aminomethyl)cyclohexyl]methyl}-$N^2$-(2,3-dichlorobenzyl)-5-nitropyrimidine-2,4-diamine
$N^4$-{[4-(aminomethyl)cyclohexyl]methyl}-$N^2$-(2-bromobenzyl)-5-nitropyrimidine-2,4-diamine
$N^2$-(2-chlorobenzyl)-5-nitro-$N^4$-(piperidin-4-ylmethyl)pyrimidine-2,4-diamine
$N^4$-{[trans-4-(aminomethyl)cyclohexyl]methyl}-5-nitro-$N^2$-[2-(trifluoromethoxy)benzyl]-pyrimidine-2,4-diamine or a tautomer, or pharmaceutically acceptable salt thereof; or a corresponding compound having at least one amine group protected by an amino-protecting group.

8. A compound according to claim 1, selected from:
$N^4$-({4-[(dimethylamino)methyl]cyclohexyl}methyl)-$N^2$-(1-naphthylmethyl)-5-nitropyrimidine-2,4-diamine
$N^2$-[2-(methylthio)benzyl]-5-nitro-$N^4$-(piperidin-4-ylmethyl)pyrimidine-2,4-diamine
5-nitro-$N^4$-(piperidin-4-ylmethyl)-$N^2$-{2-[(trifluoromethyl)thio]benzyl}pyrimidine-2,4-diamine
$N^2$-(1-naphthylmethyl)-5-nitro-$N^4$-(piperidin-4-ylmethyl)pyrimidine-2,4-diamine
$N^4$-({4-[(dimethylamino)methyl]cyclohexyl}methyl)-$N^2$-[2-(methylthio)benzyl]-5-nitropyrimidine-2,4-diamine
$N^4$-({4-[(dimethylamino)methyl]cyclohexyl}methyl)-5-nitro-$N^2$-{2-[(trifluoromethyl)thio]benzyl}pyrimidine-2,4-diamine
$N^4$-({4-[(dimethylamino)methyl]cyclohexyl}methyl)-$N^2$-(1-naphthylmethyl)-5-nitropyrimidine-2,4-diamine
$N^4$-{4-[(dimethylamino)methyl]benzyl}-N-[2-(methylthio)benzyl]-5-nitropyrimidine-2,4-diamine
$N^4$-{4-[(dimethylamino)methyl]benzyl}-5-nitro-$N^2$-{2-[(trifluoromethyl)thio]benzyl}pyrimidine-2,4-diamine
$N^4$-[(1-methylpiperidin-4-yl)methyl]-$N^2$-[2-(methylthio)benzyl]-5-nitropyrimidine-2,4-diamine
$N^4$-[(1-methylpiperidin-4-yl)methyl]-5-nitro-$N^2$-{2-[(trifluoromethyl)thio]benzyl}pyrimidine-2,4-diamine
$N^4$-{[4-(aminomethyl)cyclohexyl]methyl}-$N^2$-(2-methoxybenzyl)-5-nitropyrimidine-2,4-diamine
$N^4$-{[4-(aminomethyl)cyclohexyl]methyl}-5-nitro-$N^2$-[2-(trifluoromethoxy)benzyl]pyrimidine-2,4-diamine
$N^4$-{[4-(aminomethyl)cyclohexyl]methyl}-$N^2$-(2,3-dichlorobenzyl)-5-nitropyrimidine-2,4-diamine
$^4$-{[3-(aminomethyl)cyclohexyl]methyl}-$N^2$-(2-chlorobenzyl)-5-nitropyrimidine-2,4-diamine
$N^2$-(2-chlorobenzyl)-$N^4$-({4-[(dimethylamino)methyl]cyclohexyl}methyl)-5-nitropyrimidine-2,4-diamine
$N^4$-{[4-(aminomethyl)cyclohexyl]methyl}-$N^2$-(2-bromobenzyl)-5-nitropyrimidine-2,4-diamine
$N^4$-{[4-(aminomethyl)cyclohexyl]methyl}-$N^2$-[2-(methylthio)benzyl]-5-nitropyrimidine-2,4-diamine N$^4$-{[4-(aminomethyl)cyclohexyl]methyl}-5-nitro-N$^2$-{2-[(trifluoromethyl)thio]benzyl}pyrimidine-2,4-diamine N$^4$-{[4-(aminomethyl)cyclohexyl]methyl}-N$^2$-(1-naphthylmethyl)-5-nitropyrimidine-2,4-diamine N$^4$-{[4-(aminomethyl)cyclohexyl]methyl}-N$^2$-(2,3-dichlorobenzyl)-5-nitropyrimidine-2,4-diamine N$^4$-{[4-(aminomethyl)cyclohexyl]methyl}-N$^2$-(2-bromobenzyl)-5-nitropyrimidine-2,4-diamine N$^2$-(2-chlorobenzyl)-5-nitro-N$^4$-(piperidin-4-ylmethyl)pyrimidine-2,4-diamine or a tautomer, or pharmaceutically acceptable salt thereof; or a corresponding compound having at least one amine group protected by an amino-protecting group.

9. A pharmaceutical composition comprising a compound according to claim 1, and at least one pharmaceutically acceptable carrier or adjuvant.

10. A method of treating type I diabetes in a patient comprising administering to said patient a therapeutically effective amount of a compound according to claim 1.

11. A method of treating type II diabetes in a patient comprising administering to said patient a therapeutically effective amount of a compound according to claim 1.

12. A method of making a compound of the formula (I) below:

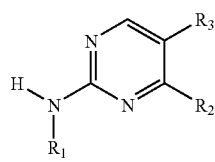

(I)

wherein R$_1$, R$_2$ and R$_3$ are as defined in claim 1, said method comprising:
(a) reacting the compound of formula (II), wherein X and X' are halogens, with an amine R'R"NH, wherein —NR'R" is as defined for R$_2$ in the presence of a base to form a compound of formula (III):

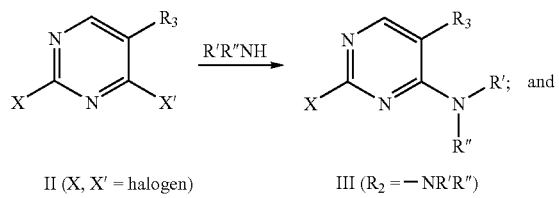

(b) reacting the compound of formula (III) with an amine R$_1$NH$_2$ to form the compound of formula (I):

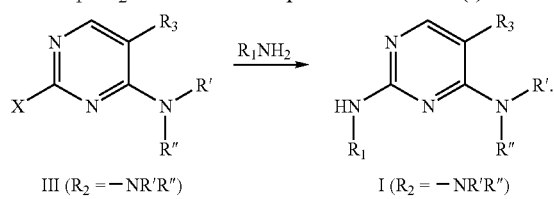

13. A method of making a compound of the formula (I) below:

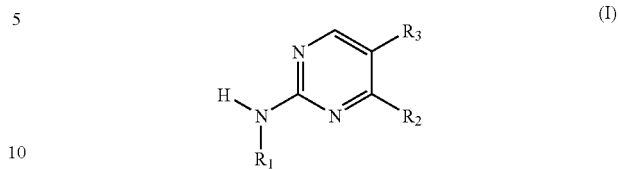

(I)

wherein R$_1$ and R$_2$ are as defined in claim 1 and R$_3$ is NO$_2$, said method comprising:
(a) reacting the compound of formula (II), wherein X and X' are halogens, with a thiocyanate salt to produce a compound of formula (VI):

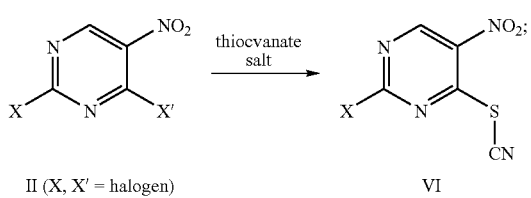

(b) reacting the compound of formula (VI) with R$_1$NH$_2$ in the presence of a base to provide the compound of formula (VII):

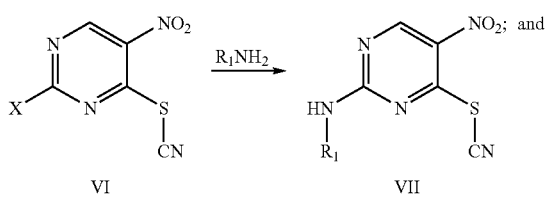

(c) reacting the compound of formula (VII) with an amine R'R"NH, wherein —NR'R" is as defined for R$_2$, to provide the compound of formula (I):

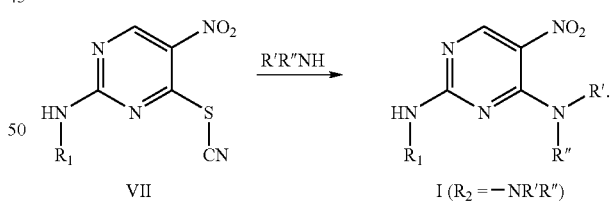

* * * * *